United States Patent [19]
Bach et al.

[11] Patent Number: 5,578,634
[45] Date of Patent: Nov. 26, 1996

[54] 1H-INDOLE-3-ACETIC ACID HYDRAZIDE SPLA₂ INHIBITORS

[75] Inventors: Nicholas J. Bach, Indianapolis; Robert D. Dillard, Zionsville; Susan E. Draheim, Indianapolis; Robert B. Hermann, Indianapolis; Richard W. Schevitz, Indianapolis, all of Ind.

[73] Assignee: Eli Lilly and Company, Indianapolis, Ind.

[21] Appl. No.: 440,154

[22] Filed: May 12, 1995

Related U.S. Application Data

[62] Division of Ser. No. 48,608, Apr. 16, 1993.

[51] Int. Cl.⁶ .................. C07D 209/18; C07D 403/06; A61K 31/405; A61K 31/41
[52] U.S. Cl. .................. 514/419; 548/494; 548/135; 548/253; 548/414; 514/92; 514/381; 514/362
[58] Field of Search .................. 548/494, 135, 548/253, 414; 514/419, 92, 381, 362

[56] References Cited

U.S. PATENT DOCUMENTS

| | | | |
|---|---|---|---|
| 2,825,734 | 3/1958 | Speeter, M. | 260/319 |
| 2,890,223 | 6/1959 | Woolley | 260/319 |
| 3,196,162 | 7/1965 | Sarett | 260/319 |
| 3,242,162 | 3/1966 | Sarett | 260/211 |
| 3,242,163 | 3/1966 | Sarett | 260/211 |
| 3,242,193 | 3/1966 | Sarett | 260/319 |
| 3,271,416 | 9/1966 | Shen | 260/326 |

OTHER PUBLICATIONS

Seilhamer, Jeffrey, et al., "Cloning and Recombinant Expression of Phospholipase A₂ present in Rheumatoid Arthritic Synovial Fluid"; *The Journal of Biolgical Chemistry*, 254:10, Apr. 5, 1989, pp. 5335–5338.

Kramer, Ruth, et al., "Structure and Properties of a Human Non–Pancreatic Phospholipase A₂", *The Journal of Biological Chemistry*, 264.10, Apr. 5, 1989, pp. 5768–5775.

Shaw, Elliott, "The Synthesis of Tryptamines Related to Serotonin", *Journal American Chemical Soc.*, vol. 77, Aug. 20, 1955, pp. 4319–4324.

Julia, Marc, et al., "No. 193—Recherches en serie indolique". Memoire No. V: *Bull. Soc. Chim.*, 1962, 1042.

Walton, Edward, et al., "Some Analogs of 1–p–Chlorobenzyl–5–methylindole–3–acetic Acid", *J. Med. Chem.*, vol. 11, 1968, pp. 1252–1255.

Romeo, E., "2–Aryl–3–Indoleglyoxylamides (FGIN–1): A New Class of Potent and Specific Ligands for the Mitochondrial DBI Receptor (MDR)", *The Journal of Pharmacology and Experimental Therapeutics*, vol. 262, No. 3, pp. 971–978 (1992).

Carlin, Robert B., et al., "Studies on the Fischer Indole Synthesis I", *Journal American Chemical Society*, vol. 70, Oct. 1948, pp. 3421–3424.

Yoshihiko Ito, et al., "The First Total Synthesis of OPC–15161", *J. Org. Chem.*, 1991, 56, pp. 4864–4867.

Clark, Robin D., et al., "Preparation of Indoles and Oxindoles from N–(Tert–Butoxycarbonyl)–2–Alkylanilines", *Synthesis*, Oct. 1991, pp. 871–878.

Wayland, E. Noland, et al., "Nitration of Indoles II, The Mononitration of Methylindoles", *J. Org. Chem.*, vol. 28, Sep. 1963, pp. 2262–2266.

Miyaura, N., et al., "The Palladium–Catalyzed Cross–Coupling Reaction of Phenylboronic Acid with Haloarenes in the Presnce of Bases", *Synthetic Communications*, 11:7 1981, pp. 513–519.

Reynolds, et al., "Analysis of Human Synovial Fluid Phospholipase A₂ on Short Chain Phosphatidylcholine–Mixed Micelles; Development of a Spectrophotometric Assay Suitable for a Microtiterplate Reader", *Analytical Biochem*, 204, 1992, pp. 190–197.

Rossum, et al., "Cumulative Dose–Response Curves", *Arch. Int. Pharmacodyn*, 143, No. 3–4, 1963, pp. 299–330.

Waud, Douglas R. "Analysis of Dose–Response Relationships", *Advances in General and Cellular Pharmacology*, eds., Narahashi, Branchi, 1:145–178, 1976.

Julia, Marc. et al., "No. 193—Recherches en serie indolique." Memoire No. VI: *Bull. Soc. Chim.*, 1962, 1060.

*Primary Examiner*—David B. Springer
*Attorney, Agent, or Firm*—Roger S. Benjamin; David E. Boone

[57] ABSTRACT

A class of novel 1H-indole-3-acetic acid hydrazides is disclosed together with the use of such indole compounds for inhibiting sPLA₂ mediated release of fatty acids (e.g., arachidonic acid) for treatment of conditions such as septic shock.

10 Claims, No Drawings

1H-INDOLE-3-ACETIC ACID HYDRAZIDE SPLA$_2$ INHIBITORS

This application is a division of application Ser. No. 08/048,608 filed Apr. 16, 1993.

FIELD OF THE INVENTION

This invention relates to novel 1H-indole-3-acetic acid hydrazides useful for inhibiting sPLA$_2$ mediated release of arachidonic acid for conditions such as septic shock.

BACKGROUND OF THE INVENTION

The structure and physical properties of human non-pancreatic secretory phospholipase A$_2$ (hereinafter called, "sPLA$_2$") has been thoroughly described in two articles, namely, "Cloning and Recombinant Expression of Phospholipase A$_2$ Present in Rheumatoid Arthritic Synovial Fluid" by Seilhamer, Jeffrey J.; Pruzanski, Waldemar; Vadas Peter; Plant, Shelley; Miller, Judy A.; Kloss, Jean; and Johnson, Lorin K.; *The Journal of Biological Chemistry*, Vol. 264, No. 10, Issue of Apr. 5, pp. 5335–5338, 1989; and "Structure and Properties of a Human Non-pancreatic Phospholipase A$_2$" by Kramer, Ruth M.; Hession, Catherine; Johansen, Berit; Hayes, Gretchen; McGray, Paula; Chow, E. Pingchang; Tizard, Richard; and Pepinsky, R. Blake; *The Journal of Biological Chemistry*, Vol. 264, No. 10, Issue of Apr. 5, pp. 5768–5775, 1989; the disclosures of which are incorporated herein by reference.

It is believed that sPLA$_2$ is a rate limiting enzyme in the arachidonic acid cascade which hydrolyzes membrane phospholipids. Thus, it is important to develop compounds which inhibit sPLA$_2$ mediated release of fatty acids (e.g., arachidonic acid). Such compounds would be of value in general treatment of conditions induced and/or maintained by overproduction of sPLA$_2$; such as septic shock, adult respiratory distress syndrome, pancreatitis, trauma, bronchial asthma, allergic rhinitis, rheumatoid arthritis, and etc.

Indolyl-3 substituted compounds having glyoxylamide functionality are described in U.S. Pat. No. 2,825,734. This patent related to a process for converting glyoxyamides to 3-(2-amino-1-hydroxyethyl)indoles.

U.S. Pat. No. 3,271,416 describes indolyl aliphatic acids as sun screening agents and intermediates. These acids may be —NH$_2$ substituted (see, definition of M in claim 1) and require 5- or 6- position substitution with nitrogen or sulfur functional groups.

U.S. Pat. No. 2,890,223 and the article "The Synthesis of Tryptamines Related to Serotaonin", by Elliott Shaw, J. Am. Chem. Soc., Vol. 77, 1955, (pp. 4319–4324 describe several amide derivatives of 3-indoleacetic acids. These compounds are used in the preparation of 5-lower alkoxy tryptamines and are stated to have utility for influencing serotonin related functions in the brain.

Selected indole type compounds have been described in the literature for the treatment of arthritic disorders. Thus, U.S. Pat. Nos. 3,196,162; 3,242,162; 3,242,163; and 3,242, 193 (see, Col. 3, lines 55–60, Example 56) describe indolyl aliphatic acids together with their related salts, esters, and amides. These compounds are closely related to compounds like indomethacin, have a substituted benzyl group at the 1 position and likely achieve their beneficial action being cyclooxygenase inhibitors.

The article, "Recherches en serie indolique. VI sur tryptamines substituees", by Marc Julia, Jean Igolen and Hanne Igolen, Bull. Soc. Chim. France, 1962, pp. 1060–1068, describes certain indole-3-acetic acid hydrazides and their conversion to tryptamine derivatives.

It is desirable to develop new compounds and treatments for sPLA$_2$ induced diseases.

SUMMARY OF THE INVENTION

This invention is a novel use of the class of compounds known as 1H-indole-3-acetic acid hydrazide to inhibit human sPLA$_2$ mediated release of arachidonic acid.

This invention is also novel classes of 1H-indole-3-acetic acid hydrazide having potent and selective effectiveness as inhibitors of human sPLA$_2$.

This invention is also pharmaceutical compositions containing the 1H-indole-3-acetic acid hydrazide of the invention.

This invention is also a method of preventing and treating septic shock using the 1H-indole-3-acetic acid hydrazides of the invention.

DETAILED DESCRIPTION OF THE INVENTION

The compounds of the invention having utility for inhibiting sPLA$_2$ mediated release of arachidonic acid are selected from "1H-indole-3-hydrazides" having the general formula (A);

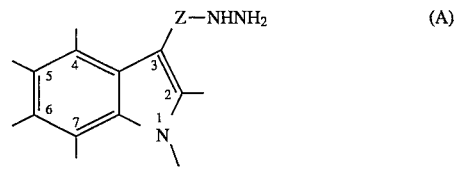

where Z is a divalent organic radical represented by

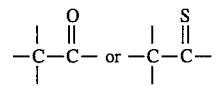

and the unsubstituted positions on the indolyl nucleus are independently satisfied by hydrogen or a non-interfering organic radical.

Certain 1H-indole-3-acetic acid hydrazides of the invention are preferred embodiments of formula (A) and for these compounds certain defining terms are used herein. In particular, the term, "alkyl" by itself or as part of another substituent means, unless otherwise defined, a straight or branched chain monovalent hydrocarbon radical such as methyl, ethyl, n-propyl, isopropyl, n-butyl, tertiary butyl, isobutyl, sec-butyl, n-pentyl, and n-hexyl. The term, "alkenyl" employed alone or in combination with other terms means a straight chain or branched monovalent hydrocarbon group having the stated number range of carbon atoms, and typified by groups such as vinyl, propenyl, crotonyl, isopentenyl, and various butenyl isomers. The term, "halo" means fluoro, chloro, bromo, or iodo. The term, "substituted or unsubstituted 5 to 10 membered heterocyclic ring", refers to compounds having nuclei such as pyrrole, furan, thiophene, pyridine, piperidine, azepine, indole, quinoline, imidazole, oxazole, thiazole, pyrazine, and pyrimidine. The term, "carbocyclic ring" means an organic nucleus whose ring forming atoms are solely carbon atoms, for example, a nucleus derived from benzene, naphthalene, cyclopentene, cyclohexane, or bicycloheptadiene. The term, "acidic group" means an organic group which when attached to an indole nucleus thru suitable connecting atoms (e.g., an alkylidene chain) acts as a proton donor capable of hydrogen bonding. Illustrative "acidic groups" include the following substituents:

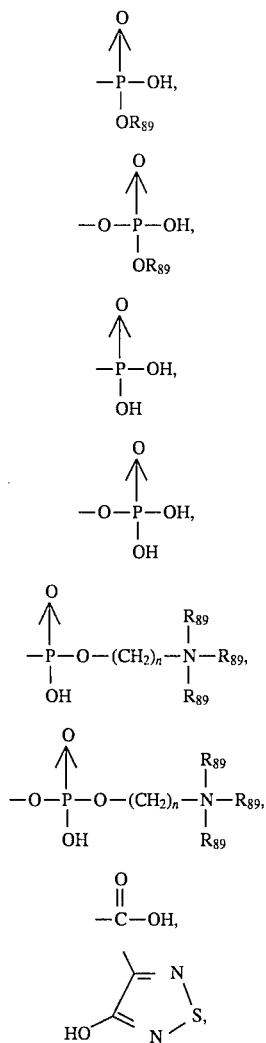

where $R_{89}$ is alkyl.

A preferred species of 1H-indole-3-acetic acid hydrazide useful in the practice of this invention are those substituted at the 2 position by groups other than hydrogen and represented by such compounds as represented by the formula (I), and pharmaceutically acceptable salts thereof;

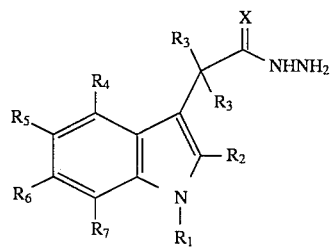

wherein
X is oxygen or sulfur;
$R_1$ is selected from groups (i), (ii) and (iii) where;
(i) is $C_4$–$C_{20}$ alkyl, $C_4$–$C_{20}$ alkenyl, $C_4$–$C_{20}$ alkynyl, $C_4$–$C_{20}$ haloalkyl, $C_4$–$C_{12}$ cycloalkyl, or (ii) is aryl or aryl substituted by halo, —CN, —CHO, —OH, —SH, $C_1$–$C_{10}$ alkylthio, $C_1$–$C_{10}$ alkoxy, $C_1$–$C_{10}$ alkyl, carboxyl, amino, or hydroxyamino;
(iii) is

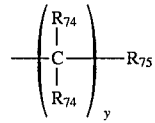

where y is from 1 to 8, $R_{74}$ is, independently, hydrogen or $C_1$–$C_{10}$ alkyl, and $R_{75}$ is aryl or aryl substituted by halo, —CN, —CHO, —OH, nitro, phenyl, —SH, $C_1$–$C_{10}$ alkylthio, $C_1$–$C_{10}$ alkoxy, $C_1$–$C_{10}$ alkyl, amino, hydroxyamino or a substituted or unsubstituted 5 to 8 membered heterocyclic ring;

$R_2$ is halo, $C_1$–$C_3$ alkyl, ethenyl, $C_1$–$C_2$ alkylthio, $C_1$–$C_2$ alkoxy, —CHO, —CN;

each $R_3$ is independently hydrogen, $C_1$–$C_3$ alkyl, or halo;

$R_4$, $R_5$, $R_6$, and $R_7$ are each independently hydrogen, $C_1$–$C_{10}$ alkyl, $C_2$–$C_{10}$ alkenyl, $C_2$–$C_{10}$ alkynyl, $C_3$–$C_8$ cycloalkyl, aryl, aralkyl, or any two adjacent hydrocarbyl groups in the set $R_4$, $R_5$, $R_6$, and $R_7$ combined with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or a group having the formula;

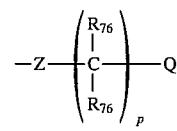

where,
each $R_{76}$ is independently selected from hydrogen, $C_1$–$C_{10}$ alkyl, hydroxy, or both $R_{76}$ taken together are =O;
p is 1 to 8,
Z is a bond, —O—, —N($C_1$–$C_{10}$ alkyl)—, —NH, or —S—;
and
Q is —CON($R_{82}R_{83}$), -5-tetrazolyl, —SO$_3$H,

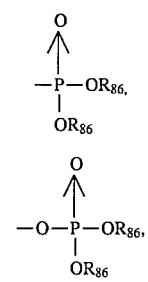

-continued

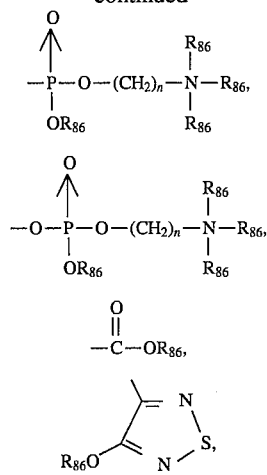

where $R_{86}$ is independently selected from hydrogen, a metal, or $C_1$–$C_{10}$ alkyl.

Another preferred species of acetic acid hydrazide useful in the practice of this invention are those substituted at the 1 position by groups other than benzyl, for example, alkyl and aryl. Such acetic acid hydrazides are represented by the formula (II), and pharmaceutically acceptable salts thereof;

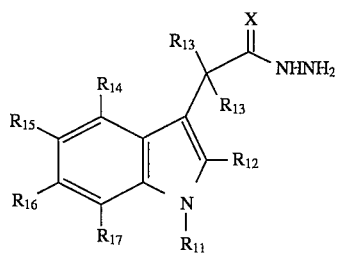

wherein;

X is oxygen or sulfur;

$R_{11}$ is selected from groups (i), (ii) and (iii) where;
(i) is $C_4$–$C_{20}$ alkyl, $C_4$–$C_{20}$ alkenyl, $C_4$–$C_{20}$ alkynyl, $C_4$–$C_{20}$ haloalkyl, $C_4$–$C_{12}$ cycloalkyl, or
(ii) is aryl or aryl substituted by halo, nitro, —CN, —CHO, —OH, —SH, $C_1$–$C_{10}$ alkyl, $C_1$–$C_{10}$ alkylthio, $C_1$–$C_{10}$ alkoxyl, carboxyl, amino, or hydroxyamino; and
(iii) is —(NH)—($R_{81}$), where $R_{81}$ is a group recited in (i) or (ii);

$R_{12}$ is hydrogen, halo, $C_1$–$C_3$ alkyl, ethenyl, $C_1$–$C_2$ alkylthio, $C_1$–$C_2$ alkoxy, —CHO, —CN;

each $R_{13}$ is independently hydrogen, $C_1$–$C_3$ alkyl, or halo;

$R_{14}$, $R_{15}$, $R_{16}$, and $R_{17}$ are each independently hydrogen, $C_1$–$C_{10}$ alkyl, $C_2$–$C_{10}$ alkenyl, $C_2$–$C_{10}$ alkynyl, $C_3$–$C_8$ cycloalkyl, aryl, aralkyl, or any two adjacent hydrocarbyl groups in the set $R_{14}$, $R_{15}$, $R_{16}$, and $R_{17}$ combined with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$–$C_{10}$ alkyl, $C_1$–$C_{10}$ hydroxyalkyl or taken together with N, $R_{82}$ and $R_{83}$ form a 5 to 8 membered heterocyclic ring; or a group having the formula;

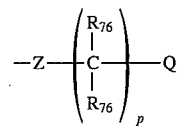

where, each $R_{76}$ is independently selected from hydrogen, $C_1$–$C_{10}$ alkyl, hydroxy, or both $R_{76}$ taken together are =O;

p is 1 to 8,

Z is a bond, —O—, —N($C_1$–$C_{10}$ alkyl)—, —NH, or —S—; and

Q is —CON($R_{82}R_{83}$), -5-tetrazolyl, —SO$_3$H,

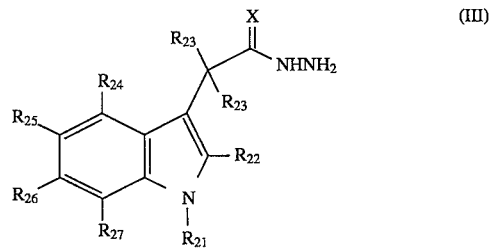

where $R_{86}$ is, independently, hydrogen, a metal, or $C_1$–$C_{10}$ alkyl.

Another preferred species of acetic acid hydrazide useful in the practice of this invention are those substituted at the 5 or 6 positions by groups other than methoxy, for example, acidic groups or simple derivatives of such acidic groups. Such acetic acid hydrazides are represented by the formula (III), and pharmaceutically acceptable salts thereof;

(III)

wherein;

X is oxygen or sulfur;

$R_{21}$ is selected from groups (i), (ii) and (iii) where;
(i) is $C_4$–$C_{20}$ alkyl, $C_4$–$C_{20}$ alkenyl, $C_4$–$C_{20}$ alkynyl, $C_4$–$C_{20}$ haloalkyl, $C_4$–$C_{12}$ cycloalkyl, or
(ii) is aryl or aryl substituted by halo, —CN, —CHO, —OH, —SH, $C_1$–$C_{10}$ alkylthio, $C_1$–$C_{10}$ alkoxy, $C_1$–$C_{10}$ alkyl, carboxyl, amino, or hydroxyamino;
(iii) is $$-\left(\begin{array}{c}R_{74}\\|\\C\\|\\R_{74}\end{array}\right)_y-R_{75}$$

where y is from 1 to 8, $R_{74}$ is, independently, hydrogen or $C_1$–$C_{10}$ alkyl, and $R_{75}$ is aryl or aryl substituted by halo, —CN, —CHO, —OH, nitro, phenyl, —SH, $C_1$–$C_{10}$ alkylthio, $C_1$–$C_{10}$ alkoxy, $C_1$–$C_{10}$ alkyl, amino, hydroxyamino or a substituted or unsubstituted 5 to 8 membered heterocyclic ring;

$R_{22}$ is hydrogen, halo, $C_1$–$C_3$ alkyl, ethenyl, $C_1$–$C_2$ alkylthio, $C_1$–$C_2$ alkoxy, —CHO, —CN;

each $R_{23}$ is independently hydrogen, $C_1$–$C_3$ alkyl, or halo;

$R_{24}$, $R_{25}$, $R_{26}$, and $R_{27}$ are each independently hydrogen, $C_1$–$C_{10}$ alkyl, $C_2$–$C_{10}$ alkenyl, $C_2$–$C_{10}$ alkynyl, $C_3$–$C_8$ cycloalkyl, aryl, aralkyl, or any two adjacent hydrocarbyl groups in the set $R_{24}$, $R_{25}$, $R_{26}$, and $R_{27}$ combined with the ring carbon atoms to which they are attached to form a 5 or 6 membered substituted or unsubstituted carbocyclic ring; or $C_1$–$C_{10}$ haloalkyl, $C_2$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or
a group having the formula;

$$-Z-\left(\begin{array}{c}R_{76}\\|\\C\\|\\R_{76}\end{array}\right)_p-Q$$

where, each $R_{76}$ is independently selected from hydrogen, $C_1$–$C_{10}$ alkyl, hydroxy, or both $R_{76}$ taken together are =O;

p is 1 to 8,

Z is a bond, —O—, —N($C_1$–$C_{10}$ alkyl)—, —NH, or —S—;

and

Q is —CON($R_{82}R_{83}$), -5-tetrazolyl, —SO$_3$H, $$-\overset{O}{\underset{OR_{86}}{\overset{\|}{P}}}-OR_{86},\ -O-\overset{O}{\underset{OR_{86}}{\overset{\|}{P}}}-OR_{86},\ -\overset{O}{\underset{OR_{86}}{\overset{\|}{P}}}-O-(CH_2)_n-\overset{R_{86}}{\underset{R_{86}}{\overset{|}{N}}}-R_{86},$$

$$-O-\overset{O}{\underset{OR_{86}}{\overset{\|}{P}}}-O-(CH_2)_n-\overset{R_{86}}{\underset{R_{86}}{\overset{|}{N}}}-R_{86},\ -\overset{O}{\overset{\|}{C}}-OR_{86},\ R_{86}O\diagdown\diagup{=}N\diagdown S\diagup N$$

where $R_{86}$ is, independently, hydrogen, a metal, or $C_1$–$C_{10}$ alkyl.

Most preferred are those acetic acid hydrazides represented by the formula (V), and pharmaceutically acceptable salts thereof;

(V)

[Structure showing indole ring with substituents $R_{51}$, $R_{52}$, $R_{53}$, $R_{53}$, $R_{54}$, $R_{55}$, $R_{56}$, $R_{57}$, and side chain with X (=O), NH$_2$]

wherein;

X is oxygen;

$R_{51}$ is $$-\overset{R_{84}}{\underset{R_{84}}{\overset{|}{C}}}-R_{87}$$

where, $R_{84}$ is hydrogen or $C_1$–$C_{10}$ alkyl, and $R_{87}$ is aryl or aryl substituted by halo, —CN, —CHO, —OH, nitro, phenyl, —SH, $C_1$–$C_{10}$ alkylthio, $C_1$–$C_{10}$ alkyl, $C_1$–$C_{10}$ alkoxyl, carboxyl, amino, hydroxyamino or a substituted or unsubstituted 5 to 8 membered heterocyclic ring;

$R_{52}$ is halo, methylthio, or $C_1$–$C_3$ alkyl;

each $R_{53}$ is hydrogen or halo;

$R_{54}$, $R_{55}$, $R_{56}$, and $R_{57}$ are each independently hydrogen, $C_1$–$C_{10}$ alkyl, $C_2$–$C_{10}$ alkenyl, $C_2$–$C_{10}$ alkynyl, $C_3$–$C_8$ cycloalkyl, aryl, aralkyl, or any two adjacent hydrocarbyl groups in the set $R_{54}$, $R_{55}$, $R_{56}$, and $R_{57}$ combined with the ring carbon atoms to which they are attached to form a 5 or 6 membered substituted or unsubstituted carbocyclic ring; or $C_1$–$C_{10}$ haloalkyl, $C_2$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or
a group having the formula;

$$-Z-\left(\begin{array}{c}R_{76}\\|\\C\\|\\R_{76}\end{array}\right)_p-Q$$

where, each $R_{76}$ is independently selected from hydrogen, $C_1$–$C_{10}$ alkyl, hydroxy, or both $R_{76}$ taken together are =O;

p is 1 to 8,

Z is a bond, —O—, —N($C_1$-$C_{10}$ alkyl)—, —NH, or —S—;

and

Q is —CON($R_{82}R_{83}$), -5-tetrazolyl, —$SO_3H$,

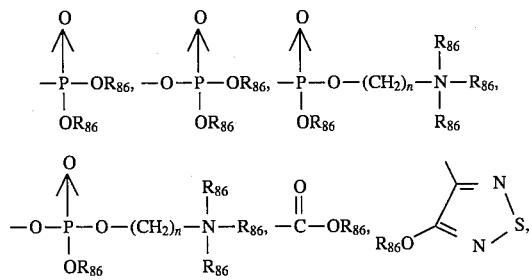

where $R_{86}$ is, independently, hydrogen, a metal, or $C_1$–$C_{10}$ alkyl.

Illustrative of the novel compounds having utility in this invention are the following:

5-cyclopentoxy-2-ethyl-1-(phenylmethyl)-1H-indole-3-acetic acid hydrazide, 2-ethyl-5-methoxy-1-(phenylmethyl)-1H-indole-3-acetic acid hydrazide 2-ethyl-5-methyl-1-(phenylmethyl)-1H-indole-3-acetic acid hydrazide 5-methoxy-2-methyl-1-(phenylmethyl)-1H-indole-3-acetic acid hydrazide, 1-[(3-chlorophenyl)methyl]-5-methoxy-2-methyl-1H-indole-3-acetic acid hydrazide, 2-chloro-5-methoxy-1-(phenylmethyl)-1H-indole-3-acetic acid hydrazide, 2-bromo-5-methoxy-1-(phenylmethyl)-1H-indole-3-acetic acid hydrazide, 5-methoxy-2-(methylthio)-1-(phenylmethyl)-1H-indole-3-acetic acid hydrazide, 5-chloro-2-methyl-1-(phenylmethyl)-1H-indole-3-acetic acid hydrazide, 5-carboxy-1-[(3-chlorophenyl)methyl]-2-methyl-1H-indole-3-acetic acid hydrazide, and mixtures thereof.

The salts of the above 1H-indole-3-acetic acid hydrazide compounds of formulae I, II, III, V, or those named are an additional aspect of the invention. Many of the salts (prepared from a corresponding indole acid or ester functional parent compound) are more water soluble and physiologically suitable than the parent compound. Examples of salts within the purview of this invention are alkali salts such as sodium, potassium and calcium as well as organic amines derived from glucosamine, morpholine, choline or diethylamine.

Synthesis Methods

The synthesis of the 1H-indole-3-acetic acid hydrazides of structure (I) can be accomplished by known methods. Procedures useful for the syntheses of the compounds of this invention are outlined in the following reaction schemes:

In the first scheme, the 1H-indole-3-acetic acid esters, II, can be readily

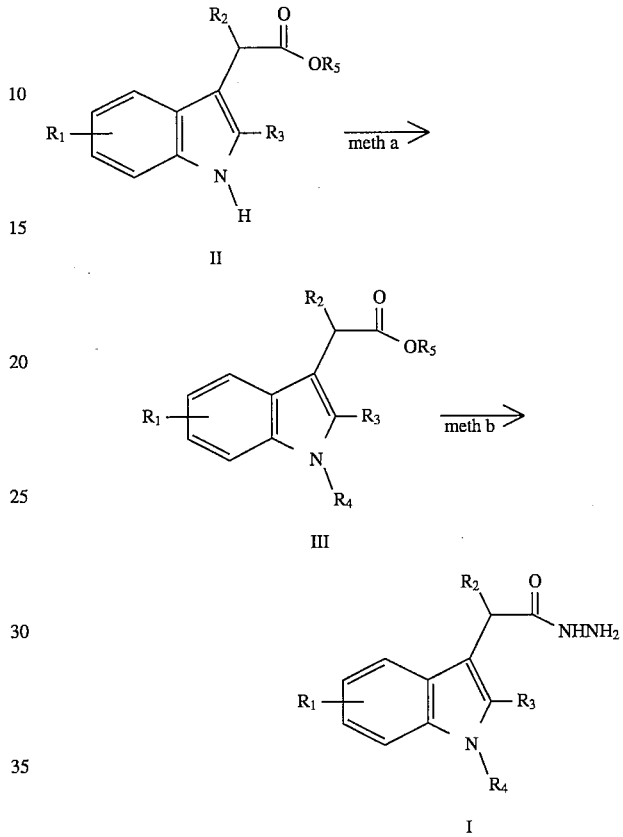

Scheme 1 alkylated by an alkyl halide or arylalkyl halide in a solvent such as N,N-dimethylformamide(DMF) in the presence of a base(meth a) to give the intermediate 1-alkyl-1H-indole-3-acetic acid esters, III. Bases such as potassium t-butoxide and sodium hydride were particularly useful. It is advantageous to react the indole, II, with the base to first form the salt of II and then add the alkylating agent. Most alkylations can be carried out at room temperature. Treatment of the 1-alkyl-1H-indole-3-acetic acid esters, III, with hydrazine or hydrazine hydrate in ethanol(meth b) gives the desired 1-alkyl-1H-indole-3-acetic acid hydrazides, I. This condensation to form I is usually carried out at the reflux temperature of the solvent for a period of 1 to 24 hours.

The intermediate 1H-indole-3-acetic acid esters, II, can be obtained from several synthetic routes as illustrated in Scheme 2. The 1H-indole-3-acetic acids, IV, are readily esterified in an alcohol such as methanol in the Scheme 2.

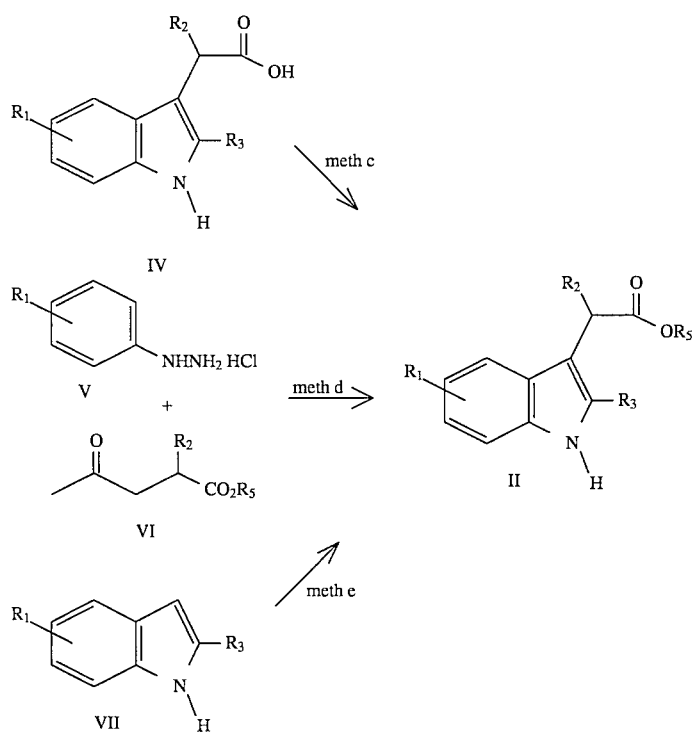

presence of a strong acid(meth c), such as sulfuric acid to give II. Substituted phenylhydrazines, V, can be reacted with levulinic acid derivatives, VI, by the well known Fisher-indole synthesis(meth d) to give ref. R. B. Carlin and E. E. Fisher, J. Am. Chem. Soc., 1948, 70, 3421.

directly the indole, II. Ethanol as solvent at reflux temperature and hydrogen chloride as the acid catalyst were generally used. Indoles that are unsubstituted at the 3-position, VII, can be alkylated by first forming the Zinc salts of VII and treating these salts with alkyl 2-bromoalkanoate ref. Yoshihiko Ito, Hideaki Sato, Masahiro Murakami, J. Org. Chem., 1991, 56, 4864–4867.

(meth e) to give II. The Zinc salts of VII can be prepared by reacting the indoles VII first with n-butyl lithium using tetrahydrofuran as solvent and then with zinc chloride in ether. The solvent for this reaction is usually changed to toluene by removing the ether and THF solvent at reduced pressure and adding toluene.

Many of the intermediate indoles, VII, are commercially available. For additional substituted derivatives of VII, the reactions in Scheme 3 were ref. Robin D. Clark, Joseph M. Muchowski, Lawrence E. Fisher Lee A. Flippin, David B. Repke, Michel Souchet, Synthesis, 1991, 871–878.

Scheme 3.

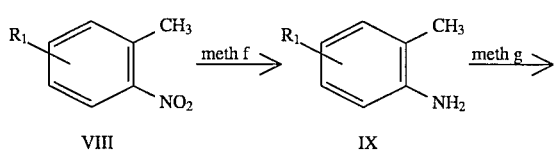

-continued
Scheme 3.

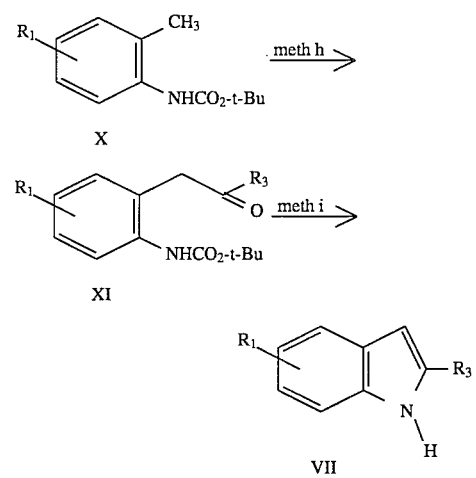

employed. Ortho-nitrotoluene derivatives, VIII, are catalytically reduced using palladium-on-carbon as catalyst to give the ortho-methylanilines, IX, which are treated with di-tert-butyl dicarbonate in THF at reflux temperature(meth g) to give the N-tert-butoxycarbonylanilines, X. The dianion of X is formed in THF by treatment with two equivalents of sec-butyl lithium and reacted with one equivalent of an N-methoxy-N-methylalkanoic acid amide to give(meth h) the aryl ketone, XI. These ketones on treatment with trifluoroacetic acid(meth i) are both cyclized and deprotected on the nitrogen to give the indoles, VII.

Indoles of type VII that are substituted at the 5- position with nitro, are ref. Wayland E. Noland, Lowell R. Smith, and Donald C. Johnson, J. Org. Chem., 1963, 28, 2262–2266.

obtained by adding sodium nitrate to the appropriate indole previously dissolved in sulfuric acid (meth j).

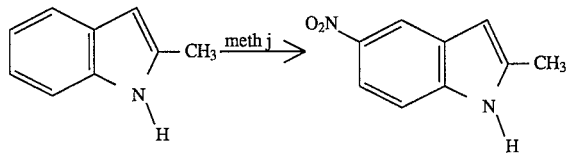

Derivatives where $R_4$ is 1-(hydroxyphenyl)methyl-, are obtained by hydrogenolyses of the corresponding 1-(benzyloxyphenyl)methyl derivatives(meth k). Derivatives where $R_4$ is 1-(aminophenyl)methyl- are readily obtained from the corresponding nitro compounds (meth l).

To synthesize compounds where the $R_1$ substituent is hydroxy, the methoxy substituted indole-3-acetic acid, XII(readily obtained by hydrolyses of III), is demethylated by reaction with $BBr_3$(meth m) to give XIII, which is ref. Tsung-Ying Shen and Charles A. Winter, Adv. Drug Res., 1977, 12, 176.

esterified by method c to give XIV. Hydroxy derivatives XIV can be alkylated by treatment with an arylalkylhalide in the presence of potassium carbonate(meth n) to give intermediate esters III where $R_1$

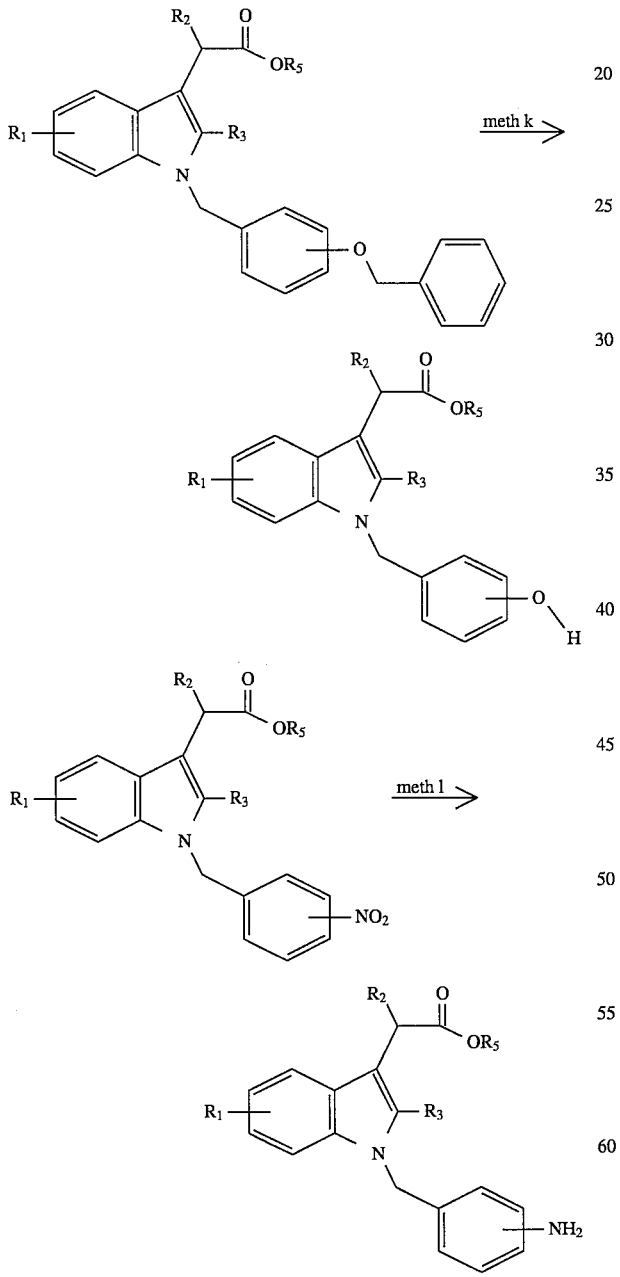

Scheme 4.

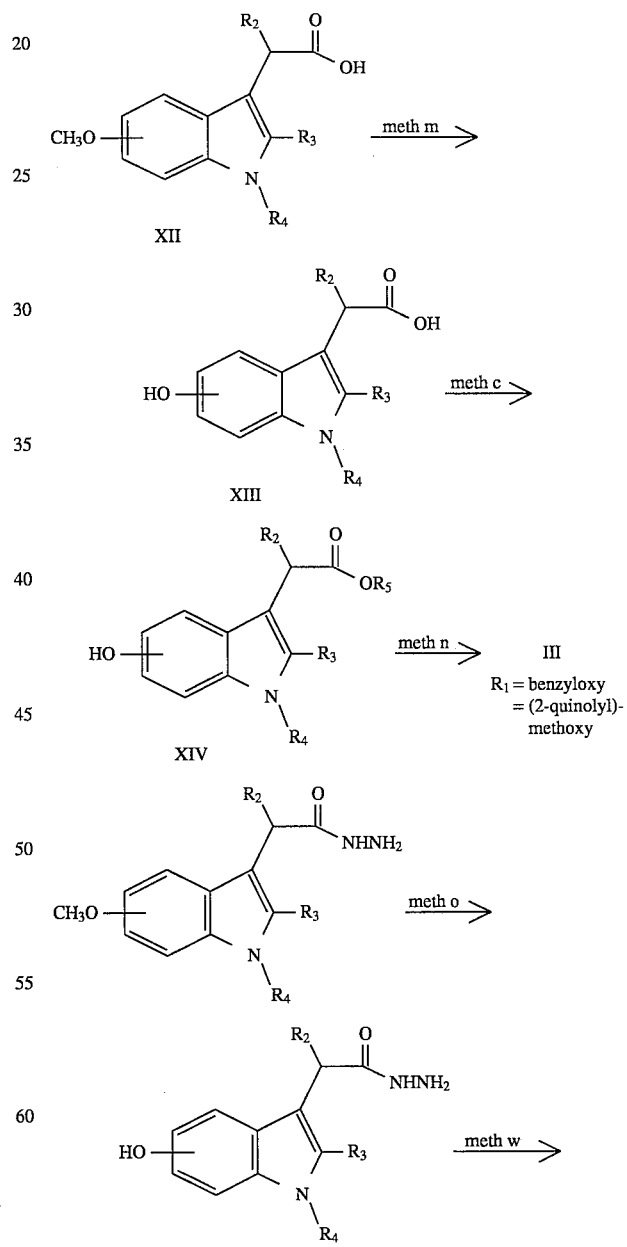

15
-continued
Scheme 4.

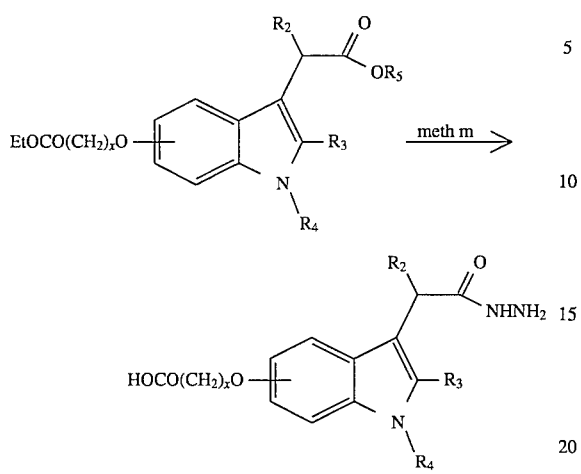

is arylmethoxy. The methoxy substituted 1H-indole-3-acetic acid hydrazides can be demethylated directly to the hydroxy substituted 1H-indole-3-acetic acid hydrazides using the BBr$_3$ conditions (meth o). These may be alkylated directly with a bromoalkanoic acid ester (meth w) using sodium hydride as a base and DMSO as solvent to give the ester acid hydrazide. The ester acid hydrazide was hydrolized by method M to the carboxy acid acid hydrazide.

Compounds of structure I and III where R$_1$ is phenyl, are made by phenylation ref. N. Miyaura, T. Yamag, A. Suzuk: Synth. Commun. 1981, 11, p. 513–519.

of the intermediates where R$_1$ is Br (meth p). This phenylation can be carried

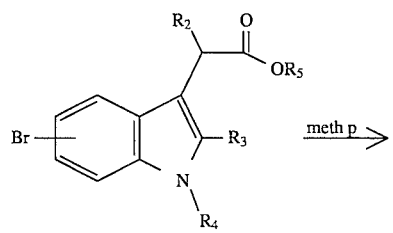

16
-continued

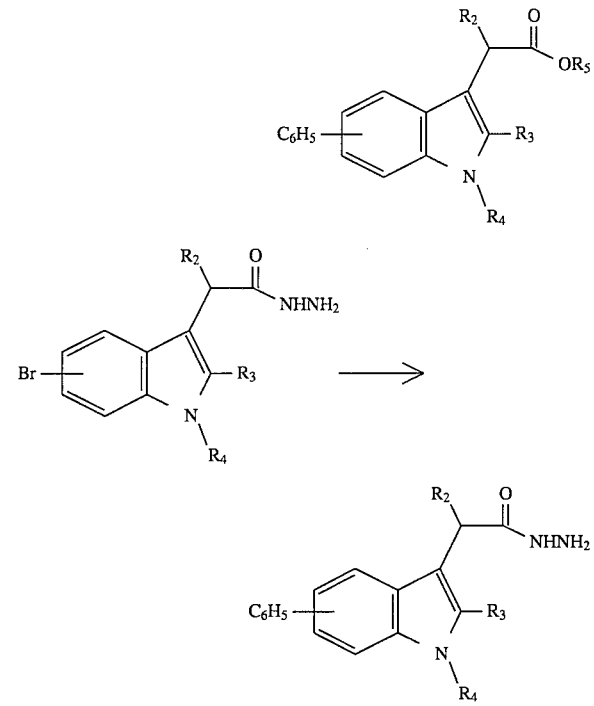

out on the appropriate bromo ester or bromo hydrazide.

The intermediate 1H-indole-3-acetic acid esters, III, where R$_3$ is chloro were made by reacting the 1H-indole-3-acetic acid ester, III, where R$_3$ is a

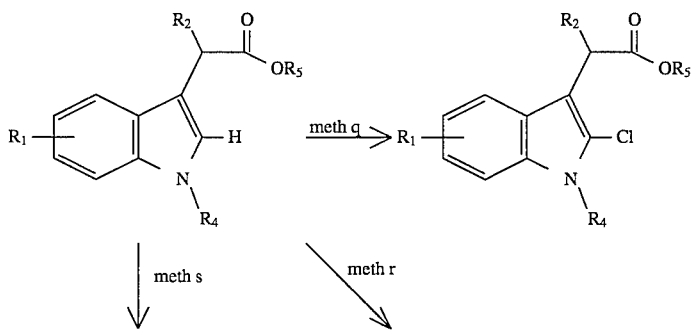

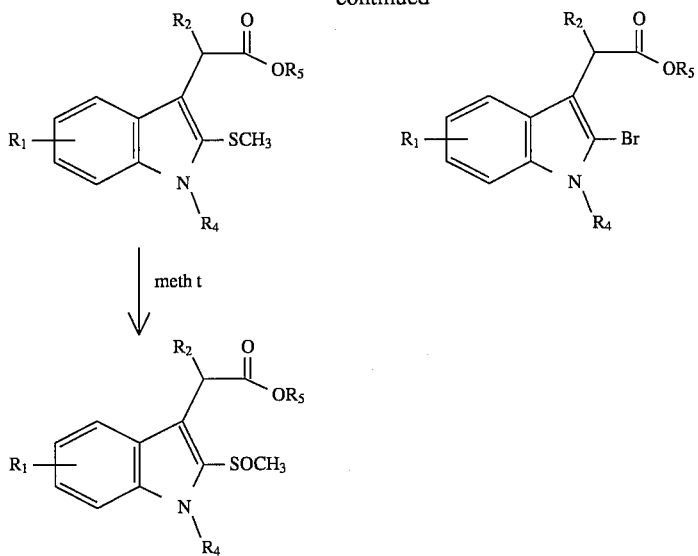

hydrogen atom with N-chlorosuccinimide(meth q). In a similar fashion, treatment with N-bromosuccinimide(meth r) or methanesulfenyl chloride(meth s) gave the 2-bromo- and 2-methylthio-indoles, respectively. The 2-methyl thio-indole could be oxidized with m-chloroperbenzoic acid to give the 2-methlysulfinyl- indole(meth t).

The intermediate 1H-indole-3-acetic acid ester, III, where $R_1$ is carboxy

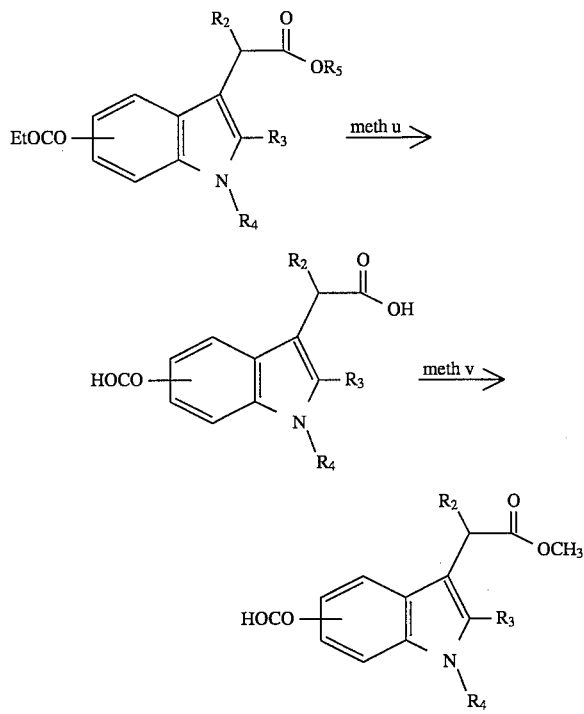

is obtained by selectively esterifying the dicarboxylic acid derivative (synthesized by hydrolysis of the di ester by meth u) to give the 1H-indole-3-acetic acid mono ester derivative.

Described below are examples of the present invention which are provided only for illustrative purposes. They are not intended to limit the scope of the present invention in any way as numerous embodiments within the scope of the claims will be apparent to those of ordinary skill in the art.

EXAMPLES

Example 1

Preparation of 5-Ethoxy-2-methyl-1-(phenylmethyl)-1H-indole-3-acetic acid hydrazide.

A. 4-Ethoxy-2-methyl-1-nitrobenzene. A solution of 15.3 g (0.1 mol) of 3-methyl-4-nitrophenol, 23.4 g (0.15 mol) of iodoethane and 27.6 g (0.2 mol) of $K_2CO_3$ in 250 mL of methyl ethyl ketone was heated to maintain reflux for 16 hours. After cooling the reaction mixture was poured into water and extracted with EtOAc. The EtOAc solution was washed with water, 1N NaOH, water, and dried over $Na_2SO_4$. After removing the solvent at reduced pressure, there was obtained 16.8g (93% yield) of 4-ethoxy-2-methyl-1-nitrobenzene, melting at 41°–43° C.

Analyses: Calc'd for $C_9H_{11}NO_3$: C, 59.66; H, 6.12; N, 7.73. Found: C, 59.58; H, 6.28; N, 7.79.

B. 4-Ethoxy-2-methylaniline. 4-Ethoxy-2-methyl-1-nitrobenzene(16.5 g, 0.091 mol) was hydrogenated at a pressure of 60 psi (4218 g/cm²) of hydrogen in 135 mL of ethanol using 1.6 g of Pd/C as catalyst for 4 hours. The catalyst was filtered and the product distilled at 54°–5° C./0.08 mmHg to give 10.62 g (78% yield) of 4-ethoxy-2-methylaniline.

Analyses: Calc'd for $C_9H_{13}NO$: C, 71.49; H, 8.67; N, 9.26. Found: C, 72.07; H, 8.95; N, 10.42.

C. N-tert-Butoxycarbonyl-4-ethoxy-2-methylaniline. A solution of 4-ethoxy-2-methylaniline (10.5 g, 0.0695 mol) and 15.5 g (0.071 mol) of di-tert-butyl dicarbonate in 200 mL of tetrahydrofuran was heated slowly to reflux and reflux maintained for 2 hours. After cooling, the reaction mixture was concentrated at reduced pressure and the residue dissolved the EtOAc. The EtOAc solution was washed with 1N citric acid solution, dried over $Na_2SO_4$, and concentrated at reduced pressure. Crystallization of the residue from hexane gave 10.26 g (59% yield) of N-tert-butoxycarbonyl-4-ethoxy-2-methylaniline melting at 55°–56° C.

Analyses: Calc'd for $C_{14}H_{21}NO_3$: C, 66.91; H, 8.42; N, 5.57. Found: C, 66.69; H, 8.23; N, 5.52.

D. 5-Ethoxy-2-methyl-1H-indole. A solution of 1.3M sec-butyl lithium/cyclohexane (105.7 mL, 0.137 mol) was added slowly to 17.25 g (0.0687 mol) of N-tert-butoxycarbonyl-4-ethoxy-2-methylaniline in 250 mL of THF while keeping the temperature below −40° C. with a dry ice-ethanol bath. After 0.25 hours 7.21 g (0.07 mol) of N-methoxy-N-methylacetamide in an equal volume of THF was added dropwise. The reaction mixture was stirred 1 hour, the cooling bath removed and stirred an additional 1 hour. It was then poured into a mixture of 500 mL of ether and 500 mL of 1N HCl. The organic layer was separated, washed with water and dried over $Na_2SO_4$. After removing the solvent there remained 17.7 g of crude 1-(2tert-butoxycarbonylamino-5-ethoxyphenyl)-2-propanone. This material and 25 g of trifluoroacetic acid in 400 mL of $CH_2Cl_2$ was stirred at room temperature for 16 hours. The mixture was washed twice with water, a saturated $Na_2CO_3$ solution and dried over $Na_2SO_4$. After removing the solvent, the product was chromatographed on silica eluting with toluene to give 4.95 g (41% yield) of 5-ethoxy-2-methyl-1H-indole melting at 76°–77° C.

Analyses: Calc'd for $C_{11}H_{13}NO$: C, 75.40; H, 7.48; N, 7.99. Found: C, 77.07; H, 7.83; N, 8.09.

E. 5-Ethoxy-2-methyl-1H-indole-3-acetic acid methyl ester. To a cooled solution of 4.85 g (0.0277 mol) of 5-ethoxy-2-methyl-1H-indole in 40 mL of THF was added 17.3 mL (0.0277 mol) of a 1.6M solution of n-butyl lithium in hexane keeping the temperature below 10° C. with an ice-ethanol bath. After 0.25 hours, 27.7 ml (0.0277 mol) of a 1M solution of $ZnCl_2$ in ether was added. The cooling bath was removed and the mixture stirred for 2 hours, concentrated at reduced pressure to a wax which was dissolved in 40 mL of toluene. To this solution was added 2.62 mL (0.0277 mol) of methyl 2-bromoacetate, the mixture was stirred 24 hours and poured into 100 mL of 1N HCl and 100 mL of EtOAc. The organic layer was washed twice with water, dried ($Na_2SO_4$), and concentrated at reduced pressure. The residue was chromatographed on silica and eluted with 5% EtOAc/toluene to give 5.0 g (73%) of 5-ethoxy-2-methyl-1H-indole-3-acetic acid methyl ester as an oil.

Analyses: Calc'd for $C_{14}H_{17}NO_3$: C, 68.00; H, 6.93; N, 5.66. Found: C, 68.04; H, 7.07; N, 5.77.

F. 5-Ethoxy-2-methyl-1-(phenylmethyl)-1H-indole-3-acetic acid methyl ester. A suspension of 80 mg (2 mmol) of 60% NaH/mineral oil was washed with hexane and placed in 8 mL of DMF. With ice-bath cooling, 494 mg (2 mmol) of 5-ethoxy-2-methyl-1H-indole-3-acetic acid methyl ester was added and stirred 1 hour, then 0.24 mL of benzyl bromide was added, and stirring maintained for 1.5 hour. The mixture was diluted with water, extracted with EtOAc, the EtOAc solution washed with water/NaCl and dried ($MgSO_4$). The solution was concentrated at reduced pressure, and the product chromatographed on silica, eluting with 25% EtOAc/hexane to give 372 mg (55% yield) of 5-ethoxy-2-methyl-1-(phenylmethyl)-1H-indole-3-acetic acid methyl ester, which solidified on standing, melting point, 82°–85° C.

Analyses: Calc'd for $C_{21}H_{23}NO_3$: C, 74.75; H, 6.87; N, 4.15. Found: C, 75.60; H, 7.04; N, 4.03.

G. 5-Ethoxy-2-methyl-1-(phenylmethyl)-1H-indole-3-acetic acid hydrazide. A solution of 323 mg (0.95 mmol) of 5-ethoxy-2-methyl-1-(phenylmethyl)-1H-indole-3-acetic acid methyl ester and 1.5 mL of 98% hydrazine in 5 mL of ethanol was heated to maintain reflux for 16 hours. The mixture was cooled, diluted with water and extracted with EtOAc. The EtOAc solution was washed with water/NaCl. dried($MgSO_4$), and concentrated at reduced pressure. The residue was crystallized from MeOH to give 77 mg (23% yield) of 5-ethoxy-2-methyl-1-(phenylmethyl)-1H-indole-3-acetic acid hydrazide, melting point, 145°–148° C.

Analyses: Calc'd for $C_{20}H_{23}N_3O_2$: C, 71.19; H, 6.87; N, 12.45. Found: C, 71.49; H, 6.94; N, 12.38.

Example 2

Preparation of 5-Cyclopentoxy-2-ethyl-1-(phenylmethyl)-1H-indole-3-acetic acid hydrazide.

A. 4-Cyclopentoxy-2-methyl-1-nitrobenzene. Using the method described in Example 1, Part A, 15.3 g (0.1 mol) of 3-methyl-4-nitrophenol, was reacted with 16.1 mL (0.15 mol) of bromocyclopentane and 27.6 g (0.2 mol) of $K_2CO_3$ to give 17.5 g (79% yield) of 4-cyclopentoxy-2-methyl-1-nitrobenzene as an oil.

B. 4-Cyclopentoxy-2-methylaniline. 4-Cyclopentoxy-2-methyl-1-nitrobenzene (17.5 g, 0.0792 mol) was hydrogenated by the method in Example 1, Part B to give 10.3 g (68% yield) of 4-cyclopentoxy-2-methylaniline that boiled at 100°–110° C./0.07 mmHg.

Analyses: Calc'd for $C_{12}H_{17}NO$: C, 75.35; H, 8.96; N, 7.32. Found: C, 75.50; H, 9.10; N, 7.57.

C. N-tert-Butoxycarbonyl-4-cyclopentoxy-2-methylaniline. By the procedure in Example 1, Part C, 10.3 g (0.54 mole) of 4-cyclopentoxy-2-methylaniline was reacted with 12.24 g (0.056 mol) of di-tert-butyl dicarbonate to give 6.3 g (40% yield) of N-tert-butoxycarbonyl-4-cyclopentoxy-2-methylaniline melting at 75°–77° C., after crystallizing from toluene/hexane.

Analyses: Calc'd for $C_{17}H_{25}NO_3$: C, 70.07; H, 8.65; N, 4.81. Found: C, 69.79; H, 8.67; N, 4.60.

D. 1-[2-(tert-Butoxycarbonylamino)-5-cyclopentoxyphenyl]-2-butanone. A solution of 1.3M sec-butyl lithium/cyclohexane (33.3 mL, 0.0433 mol) was added slowly to 6.3 g (0.0216 mol) of N-tert-butoxycarbonyl-4-cyclopentoxy-2-methylaniline in 80 mL of THF while keeping the temperature below −40° C. with a dry ice-ethanol bath. The bath was removed and the temperature allowed to rise to −20° C. and then the bath was replaced. After the temperature had cooled to −60° C., 2.57 g (0.022 mol) of N-methoxy-N-methylpropanamide in an equal volume of THF was added dropwise. The reaction mixture was stirred 1 hour, the cooling bath removed and stirred an additional 1 hour. It was then poured into a mixture of 200 mL of ether and 200 mL of 1N HCl. The organic layer was separated, washed with water and dried over $Na_2SO_4$. After removing the solvent the residue was crystallized from hexane to give 3.58 g (48% yield) of 1-(2-(tert-butoxycarbonylamino)-5-cyclopentoxyphenyl]-2-butanone, melting at 71°–73° C.

Analyses: Calc'd for $C_{20}H_{29}NO_4$: C, 69.14; H, 8.41; N, 4.03. Found: C, 69.17; H, 8.42; N, 4.14.

E. 5-Cyclopentoxy-2-ethyl-1H-indole. 1-[2-(tert-Butoxycarbonylamino-5-cyclopentoxyphenyl)]-2-butanone (6.45 g, 0.0186 mol) in 120 mL of $CH_2Cl_2$ and 20 mL of trifluoroacetic acid was stirred for 20 hours, washed with water, $NaHCO_3$ solution and the product chromatographed on silica (eluted with 5% EtOAc/toluene) to give 2.35 g (50% yield) of 5-cyclopentoxy-2-ethyl-1H-indole as an oil.

Analyses: Calc'd for $C_{15}H_{19}NO$: C, 78.56; H, 8.35; N, 6.11. Found: C, 78.84 H, 8.41; N, 6.19.

F. 5-Cyclopentoxy-2-ethyl-1H-indole-3-acetic acid methyl ester. As in Example 1, Part E, 2.33 g (0.0102 mol) of 5-cyclopentoxy-2-ethyl-1H-indole was treated with 6.4 mL (0.0102 mol) of a 1.6M solution of n-butyl lithium in hexane, 10.2 mL (0.0102 mol) of a 1M solution of $ZnCl_2$ in ether, and 0.97 mL (0.0102 mol) of methyl 2-bromoacetate to give after chromatography on silica (5% EtOAc/toluene) 1.8 g (59%) of 5-cyclopentoxy-2-methyl-1H-indole-3-acetic acid methyl ester as an oil.

Analyses: Calc'd for $C_{18}H_{23}NO_3$: C, 71.74; H, 7.69; N, 4.65. Found: C, 71.64; H, 7.89; N, 4.70.

G. 5-Cyclopentoxy-2-ethyl-1-(phenylmethyl)-1H-indole-3-acetic acid methyl ester. By the method described in Example 1, Part F, 602 mg (2 mmol) of 5-cyclopentoxy-2-ethyl-1H-indole-3-acetic acid methyl ester was converted to 427 mg (55% yield, oil) of 5-cyclopentoxy-2-ethyl-1-(phenylmethyl)-1H-indole-3-acetic acid methyl ester, purified by chromatography on silica (33% EtOAc/hexane).

Analyses: Calc'd for $C_{25}H_{29}NO_3$: C, 76.78; H, 7.47; N, 3.58. Found: C, 76.68; H, 7.62; N, 3.62.

H. 5-Cyclopentoxy-2-ethyl-1-(phenylmethyl)-1H-indole-3-acetic acid hydrazide. Using the method described in Example 1, Part G, 417 mg (1.07 mmol) of 5-cyclopentoxy-2-ethyl-1-(phenylmethyl)-1H-indole-3-acetic acid methyl ester was reacted with 1.2 mL of hydrazine to give 163 mg (39% yield) of 5-cyclopentoxy-2-ethyl-1-(phenylmethyl)-1H-indole-3-acetic acid hydrazide after crystallizing from MeOH (melting point, 117°–118° C.).

Analyses: Calc'd for $C_{24}H_{29}N_3O_2$: C, 73.62; H, 7.47; N, 10.73. Found: C, 73.52; H, 7.61; N, 10.55.

Example 3

Preparation of 2-Ethyl-5-methoxy-1-(phenylmethyl)-1H-indole-3-acetic acid hydrazide.

A. N-tert-Butoxycarbonyl-4-methoxy-2-methylaniline. By the procedure in Example 1, Part C, 13.7 g (0.1 mole) of 4-methoxy-2-methylaniline was reacted with 25 g (0.1145 mol) of di-tert-butyl dicarbonate to give 17.25 g (73% yield) of N-tert-butoxycarbonyl-4-methoxy-2-methylaniline melting at 80°–82° C., after crystallizing from hexane.

Analyses: Calc'd for $C_{13}H_{19}NO_3$: C, 65.80; H, 8.07; N, 5.90. Found: C, 65.86; H, 8.15; N, 5.61.

B. 1-[2-(tert-Butoxycarbonylamino)-5-methoxyphenyl]-2-butanone. Using the method described in Example 2, Part D, 11.85 g (0.05 mol) of N-tert-butoxycarbonyl-4-methoxy-2-methylaniline was treated with 1.3M sec-butyl lithium/cyclohexane (81 mL, 0.105 mol) and 6.1 g (0.052 mol) of N-methoxy-N-methylpropanamide to give 10.9 g (74% yield) 1-[2-(tert-butoxycarbonylamino)-5-methoxyphenyl]-2-butanone, melting at 80°–81° C., after chromatography on silica eluting with 5% EtOAc/toluene.

Analyses: Calc'd for $C_{16}H_{23}NO_4$: C, 65.51; H, 7.90; N, 4.77. Found: C, 65.69; H, 7.89; N, 4.90.

C. 2-Ethyl-5-methoxy-1H-indole.-1-[2-(tert-Butoxycarbonylamino)-5-methoxyphenyl]-2-butanone (7.33 g, 0.025 mol) was treated with 20 mL of trifluoroacetic acid as described in Example 2, Part E and the product chromatographed on silica and eluted with 20% EtOAc/hexane to give 2.54 g (58% yield) of 2-ethyl-5-methoxy-1H-indole as a white solid, mp 49°–50° C.

Analyses: Calc'd for $C_{11}H_{13}NO$: C, 75.40; H, 7.48; N, 7.99. Found: C, 75.64 H, 7.61; N, 8.04.

D. 2-Ethyl-5-methoxy-1H-indole-3-acetic acid methyl ester. As in Example 1, Part E, 3.5 g (0.02 mol) of 5-methoxy-2-ethyl-1H-indole was treated with 12.5 mL (0.02 mol) of a 1.6M solution of n-butyl lithium in hexane, 20 ml (0.02 mol) of a 1M solution of $ZnCl_2$ in ether, and 1.89 mL (0.02 mol) of methyl 2-bromoacetate to give after chromatography on silica (toluene→10% EtOAc/toluene) 3.32 g (59%) of 2-ethyl-5-methoxy-1H-indole-3-acetic acid methyl ester as an oil.

Analyses: Calc'd for $C_{14}H_{17}NO_3$: C, 67.99; H, 6.93; N, 5.66. Found: C, 67.73; H, 6.94; N, 5.39.

E. 2-Ethyl-5-methoxy-1-(phenylmethyl)-1H-indole-3-acetic acid methyl ester. A solution of 2.47 g (0.01 mol) of 2-ethyl-5-methoxy-1H-indole-3-acetic acid methyl ester in 25 mL of DMF was treated with 1.12 g (0.01 mol) of potassium t-butoxide, stirred 0.5 hour, and 1.15 mL (0.01 mol) of benzyl chloride added. After 72 hours the reaction mixture was diluted with water, extracted with EtOAc, the EtOAc solution was then washed four times with water and dried over $Na_2SO_4$. After concentrating at reduced pressure, the product was purified by chromatography on silica, eluting with a gradient, toluene→10% EtOAc/toluene, to give 1.5 g (44% yield) of 2-ethyl-5-methoxy-1-(phenylmethyl)-1H-indole-3-acetic acid methyl ester as an oil.

Analyses: Calc'd for $C_{21}H_{23}NO_3$: C, 74.75; H, 6.87; N, 4.15. Found: C, 75.00; H, 6.99; N, 4.28.

F. 2-Ethyl-5-methoxy-1-(phenylmethyl)-1H-indole-3-acetic acid hydrazide. Using the method described in Example 1, Part G, 748 mg (2.2 mmol) of 2-ethyl-5-methoxy-1-(phenylmethyl)-1H-indole-3-acetic acid methyl ester was reacted with 2.2 mL of hydrazine to give 552 mg (74% yield) of 2-ethyl-5-methoxy-1-(phenylmethyl)-1H-indole-3-acetic acid hydrazide, that crystallized out of the reaction mixture on cooling (melting point, 138°–140° C.).

Analyses: Calc'd for $C_{20}H_{23}N_3O_2$: C, 71.19; H, 6.87; N, 12.45. Found: C, 71.13 H, 6.86; N, 12.33.

Example 4

Preparation of 1-([1,1'-biphenyl]-2-ylmethyl)-2-ethyl-5-methoxy-1H-indole-3-acetic acid hydrazide.

A. 1-([1,1'-Biphenyl]-2-ylmethyl)-2-ethyl-5-methoxy-1H-indole-3-acetic acid methyl ester. Applying the procedures in Example 1 Part F, 483 mg (2 mmol) of 2-ethyl-5-methoxy-1H-indole-3-acetic acid methyl ester was treated with 48 mg (2 mmol) of 60% NaH/mineral oil and 0.37 mL (2 mmol) of 2-(bromomethyl)-biphenyl to give after chromatography on silica (elution with 20% EtOAc/hexane), 362 mg (44% yield) of 1-([1,1'-biphenyl]-2-ylmethyl)-2-ethyl-5-methoxy-1H-indole-3-acetic acid methyl ester as an oil.

Analyses: Calc'd for $C_{27}H_{27}NO_3$: C, 78.42; H, 6.58; N, 3.39. Found: C, 78.70; H, 6.59; N, 3.43.

B. 1-([1,1'-Biphenyl]-2-ylmethyl)-2-ethyl-5-methoxy-1H-indole-3-acetic acid hydrazide. Using the method described in Example 1, Part G, 859 mg (2.15 mmol) of 1-([1,1'-biphenyl]-2-ylmethyl)-2-ethyl-5-methoxy-1H-indole-3-acetic acid methyl ester was reacted with 2.5 mL of hydrazine to give 300 mg (36% yield) of 1-([1,1'-biphenyl]-2-ylmethyl)-2-ethyl-5-methoxy-1H-indole-3-acetic acid hydrazide, crystallized from MeOH, mp, 123°–125° C.

Analyses: Calc'd for $C_{26}H_{27}N_3O_2$: C, 75.52; H, 6.58; N, 10.16. Found: C, 75.29 H, 6.65; N, 9.95.

Example 5

Preparation of 5-Methoxy-1-(phenylmethyl)-2-propyl-1H-indole-3-acetic acid hydrazide.

A. 1-[2-(tert-Butoxycarbonylamino)-5-methoxyphenyl]-2-pentanone. Using the method described in Example 2, Part D, 15.17 g (0.064 mol) of N-tert-butoxycarbonyl-4-methoxy-2-methylaniline was treated with 1.3M sec-butyl lithium/cyclohexane (100 mL, 0.13 mol) and 8.4 g (0.064 mol) of N-methoxy-N-methylbutanamide to give 14.31 g (73% yield) of 1-(tert-butoxycarbonylamino-5-methoxyphenyl)-2-pentanone, melting at 77°–78° C., after chromatography on silica eluting with 5% EtOAc/toluene.

Analyses: Calc'd for $C_{17}H_{25}NO_4$: C, 66.43; H, 8.20; N, 4.56. Found: C, 66.42; H, 8.09; N, 4.71.

B. 5-methoxy-2-propyl-1H-indole.-1-[2-(tert-Butoxycarbonylamino)-5-methoxyphenyl]-2-pentanone (14.27 g, 0.0465 mol) was treated with 20 mL of trifluoroacetic acid as described in Example 2, Part E and the product crystallized from hexane to give 5.5 g (58% yield) of 5-methoxy-2-propyl-1H-indole as a white solid, mp 49°–50° C.

Analyses: Calc'd for $C_{12}H_{15}NO$: C, 76.16; H, 7.99; N, 7.40. Found: C, 76.36 H, 8.07; N, 7.52.

C. 5-Methoxy-2-propyl-1H-indole-3-acetic acid methyl ester. As in Example 1, Part E, 5.125 g (0.0271 mole) of 5-methoxy-2-propyl-1H-indole was treated with 16.9 mL (0.0271 mol) of a 1.6M solution of n-butyl lithium in hexane, 27.1 mL (0.0271 mol) of a 1M solution of $ZnCl_2$ in ether, and 2.7 mL (0.0271 mol) of methyl 2-bromoacetate to give after chromatography on silica (20% EtOAc/ hexane) 4.65 g (66%) of 5-methoxy-2-propyl-1H-indole-3-acetic acid methyl ester as an oil.

Analyses: Calc'd for $C_{15}H_{19}NO_3$: C, 68.94; H, 7.33; N, 5.36. Found: C, 68.69; H, 7.36; N, 5.63.

D. 5-Methoxy-1-(phenylmethyl)-2-propyl-1H-indole-3-acetic acid methyl ester. Using the procedure described in Example 1 Part F, 522 mg (2 mmol) of 5-methoxy-2-propyl-1H-indole-3-acetic acid methyl ester was reacted with 48 mg (2 mmol) of 60% NaH/mineral oil and 0.24 mL (2 mmol) of benzyl bromide to give after silica chromatography (25% EtOAc/hexane) 501 mg (71%) of 5-methoxy-1-(phenylmethyl)-2-propyl-1H-indole-3-acetic acid methyl ester as an oil.

E. 5-Methoxy-1-(phenylmethyl)-2-propyl-1H-indole-3-acetic acid hydrazide. Using the method described in Example 1, Part G, 480 mg (1.37 mmol) of 5-methoxy-1-(phenylmethyl)-2-propy-1H-indole-3-acetic acid methyl ester was reacted with 1.4 mL of hydrazine to give after crystallizing from MeOH 56 mg (74% yield) of 5-methoxy-1-(phenylmethyl)-2-propyl-1H-indole-3-acetic acid hydrazide, mp 140°–141° C.

Analyses: Calc'd for $C_{21}H_{25}N_3O_2$: C, 71.77; H, 7.17; N, 11.96. Found: C, 71.98 H, 7.12; N, 11.98.

Example 6

Preparation of 2-Ethyl-5-methyl-1-(phenylmethyl)-1H-indole-3-acetic acid hydrazide.

A. N-tert-Butoxycarbonyl-2,4-dimethylaniline. By the procedure in Example 1, Part C, 27.4 g (0.2 mole) of 2,4-dimethylaniline was reacted with 50 g (0.229 mol) of di-tert-butyl dicarbonate to give 18.42 g (76% yield) of N-tert-butoxycarbonyl-2,4-dimethylaniline melting at 90°–91° C., after crystallizing from hexane.

Analyses: Calc'd for $C_{13}H_{19}NO_2$: C, 70.56; H, 8.65; N, 6.33. Found: C, 67.18; H, 8.90; N, 5.39.

B. 2-Ethyl-5-methyl-1H-indole. Using methods described in Example 1, Part D, 11.05 g (0.05 mol) of N-tert-butoxycarbonyl-2,4-dimethylaniline was reacted with 81 mL of 1.3M sec-butyl lithium and 6.1 g (0.05 mol) of N-methoxy-N-methylpropanamide to give the crude 1-[2-(tert-butoxycarbonylamino)-5-methylphenyl)-2-pentanone. Treatment of this material with trifluoroacetic acid and crystallization from EtOAc/hexane gave 1.82 g (13% yield) of 2-ethyl-5-methyl-1H-indole, mp, 77°–78° C.

Analyses: Calc'd for $C_{11}H_{13}N$: C, 82.97; H, 8.23; N, 8.80. Found: C, 83.19; H, 8.35; N, 8.89.

C. 2-Ethyl-5-methyl-1H-indole-3-acetic acid methyl ester. As in Example 1, Part E, 3.18 g (0.02 mole) of 2-ethyl-5-methyl-1H-indole was treated with 12.5 mL (0.02 mol) of a 1.6M solution of n-butyl lithium in hexane, 20 ml (0.02 mol) of a 1M solution of $ZnCl_2$ in ether, and 1.89mL (0.02 mol) of methyl 2-bromoacetate to give after chromatography on silica(toluene→20% EtOAc/hexane) 3.23 g (70%) of 2-ethyl-5-methyl-1H-indole-3-acetic acid methyl ester as an oil.

Analyses: Calc'd for $C_{14}H_{17}NO_2$: C, 72.70; H, 7.41; N, 6.06. Found: C, 70.76; H, 7.29; N, 5.85.

D. 2-Ethyl-5-methyl-1-(phenylmethyl)-1H-indole-3-acetic acid methyl ester. Using the procedure described in Example 3 Part E, 1.73 g (0.0075 mol) of 2-ethyl-5-methyl-1H-indole-3-acetic acid methyl ester was reacted with 0.84 g (0.0075 mol) of potassium t-butoxide and 0.86 mL (2 mmol) of benzyl chloride to give after silica chromatography (2% EtOAc/toluene) 1.74 g (71%) of 2-ethyl-5-methyl-1-(phenylmethyl)-1H-indole-3-acetic acid methyl ester as an oil.

Analyses: Calc'd for $C_{21}H_{23}NO_2$: C, 78.47; H, 7.21; N, 4.36. Found: C, 78.68; H, 7.30; N, 4.42.

E. 2-Ethyl-5-methyl-1-(phenylmethyl)-1H-indole-3-acetic acid hydrazide. Using the method described in Example 1, Part G, 1.4 g (0.0044 mol) of 2-ethyl-5-methyl-1-(phenylmethyl)-1H-indole-3-acetic acid methyl ester was reacted with 2 mL of hydrazine to give after crystallizing from MeOH 0.77 g (55% yield) of 2-ethyl-5-methyl-1-(phenylmethyl)-1H-indole-3-acetic acid hydrazide, mp 115°–125° C.).

Analyses: Calc'd for $C_{20}H_{23}N_3O$: C, 74.74; H, 7.21; N, 13.07. Found: C, 74.73 H, 7.23; N, 13.00.

Example 7

Preparation of 2-Ethyl-5-fluoro-1-(phenylmethyl)-1H-indole-3-acetic acid hydrazide.

A. N-tert-Butoxycarbonyl-4-fluoro-2-methylaniline. By the procedure in Example 1, Part C, 44 g (0.352 mole) of 4-fluoro-2-methylaniline was reacted with 80.75 g (0.37 mol) of di-tert-butyl dicarbonate to give 60.1 g (76% yield) of N-tert-butoxycarbonyl-4-fluoro-2-methylaniline melting at 93°–95° C., after crystallizing from hexane.

Analyses: Calc'd for $C_{12}H_{16}FNO_2$: C, 63.98; H, 7.16; N, 6.22. Found: C, 63.84; H, 7.32; N, 6.26.

B. 1-[2-(tert-Butoxycarbonylamino)-5-fluorophenyl)-2-pentanone. Using methods described in Example 2, Part D, 14.4 g (0.064 mol) of N-tert-butoxycarbonyl-4-fluoro-2-methylaniline was reacted with 100 mL of 1.3M sec-butyl lithium and 7.5 g (0.064 mol) of N-methoxy-N-methylpropanamide to give after crystallizing from hexane 11.2 g (62% yield) of 1-[2-(tert-butoxycarbonylamino)-5-fluorophenyl)-2-pentanone, mp 110°–112° C.

Analyses: Calc'd for $C_{15}H_{20}FNO_3$: C, 64.04; H, 7.17 N, 4.98. Found: C, 63.02; H, 7.29; N, 4.93.

C. 2-Ethyl-5-fluoro-1H-indole.-1-[2-(tert-Butoxycarbonylamino)-5-fluorophenyl)-2-pentanone (19.0 g, 0.0676 mol) was treated with 25 mL of trifluoroacetic acid as described in Example 2, Part E and the product chromatographed on silica and eluted with toluene to give 8.89 g (81% yield) of 2-ethyl-5-fluoro-1H-indole as a white solid, mp 41°–42° C.

Analyses: Calc'd for $C_{10}H_{10}FN$: C, 73.60; H, 6.18; N, 8.58. Found: C, 73.37; H, 6.39; N, 8.31.

D. 2-Ethyl-5-fluoro-1H-indole-3-acetic acid methyl ester. As in Example 1, Part E, 8.8 g (0.054 mole) of 2-ethyl-5-fluoro-1H-indole was treated with 34.4 mL (0.055 mol) of a 1.6M solution of n-butyl lithium in hexane, 55 ml (0.055 mol) of a 1M solution of $ZnCl_2$ in ether, and 5.21 mL (0.055 mol) of methyl 2-bromoacetate to give after chromatography on silica (5% EtOAc/toluene) 6.9 g (54%) of 2-ethyl-5-fluoro-1H-indole-3-acetic acid methyl ester as an oil.

Analyses: Calc'd for $C_{13}H_{14}FNO_2$: C, 66.37; H, 6.00; N, 5.95. Found: C, 66.47; H, 6.15; N, 5.97.

E. 2-Ethyl-5-fluoro-1-(phenylmethyl)-1H-indole-3-acetic acid methyl ester. Using the procedure described in Example 3 Part E, 3.17 g (0.0135 mol) of 2-ethyl-5-fluoro-1H-indole-3-acetic acid methyl ester was reacted with 1.5 g (0.0135 mol) of potassium t-butoxide and 1.55 mL (0.0135 mol) of benzyl chloride to give after silica chromatography (5% EtOAc/toluene) 3.76 g(71%) of 2-ethyl-5-fluoro-1-(phenylmethyl)- 1H-indole-3-acetic acid methyl ester as an oil.

Analyses: Calc'd for $C_{20}H_{20}FNO_2$: C, 73.83; H, 6.20; N, 4.30. Found: C, 74.41; H, 6.35; N, 4.19.

F. 2-Ethyl-5-fluoro-1-(phenylmethyl)-1H-indole-3-acetic acid hydrazide. Using the method described in Example 1, Part G, 3.7 g (0.0114 mol) of 2-ethyl-5-fluoro-1-(phenylmethyl)-1H-indole-3-acetic acid methyl ester was reacted with 10 mL of hydrazine to give after crystallizing from MeOH/water 1.63 g (44% yield) of 2-ethyl-5-fluoro-1-(phenylmethyl)-1H-indole-3-acetic acid hydrazide, mp 127°–128° C.

Analyses: Calc'd for $C_{19}H_{20}FN_3O$: C, 70.13; H, 6.19; N, 12.91. Found: C, 70.26 H, 6.17; N, 12.71.

Example 8

Preparation of 6-Chloro-2-methyl-1-(phenylmethyl)-1H-indole-3-acetic acid hydrazide.

A. N-tert-Butoxycarbonyl-4-chloro-2-methylaniline. By the procedure in Example 1, Part C, 28.3 g (0.2 mole) of 5-chloro-2-methylaniline was reacted with 48.1 g (0.22 mol) of di-tert-butyl dicarbonate to give 37.1 g (77% yield) of N-tert-butoxycarbonyl-5-chloro-2-methylaniline melting at 100°–102° C., after crystallizing from hexane.

Analyses: Calc'd for $C_{12}H_{16}ClNO_2$: C, 59.63; H, 6.67; N, 5.79. Found: C, 59.75; H, 6.83; N, 5.74.

B. 1-[2-(tert-Butoxycarbonylamino)-4-chlorophenyl]-2-butanone. Using methods described in Example 2, Part D, 7.73 g (0.032 mol) of N-tert-butoxycarbonyl-4-chloro-2-methylaniline was reacted with 50 mL (0.065 mol) of 1.3M sec-butyl lithium and 3.3 g (0.032 mol) of N-methoxy-N-methylacetamide to give after crystallizing from hexane 3.49 g (38% yield) of 1-[2-(tert-butoxycarbonylamino)-4-chlorophenyl]-2-butanone, mp 89°–90° C.

Analyses: Calc'd for $C_{14}H_{18}ClNO_3$: C, 59.26; H, 6.39 N, 4.94. Found: C, 59.14; H, 6.30; N, 5.16.

C. 6-Chloro-2-methyl-1H-indole.-1-[2-(tert-Butoxycarbonylamino)-4-chlorophenyl]-2-butanone (3.49 g, 0.0123 mol) was treated with 10 mL of trifluoroacetic acid as described in Example 2, Part E, and the product chromatographed on silica and eluted with a gradient solvent (toluene→5% EtOAc/toluene) to give 1.2 g (59% yield) of 6-chloro-2-methyl-1H-indole as a white solid, mp 120°–122° C.

Analyses: Calc'd for $C_9H_8ClN$: C, 65.23; H, 4.87; N, 8.46. Found: C, 65.09; H, 5.07; N, 8.24.

D. 6-Chloro-2-methyl-1H-indole-3-acetic acid methyl ester. As in Example 1, Part E, 2.2 g (0.0133 mole) of 6-chloro-2-methyl-1H-indole was treated with 8.3 mL (0.0133 mol) of a 1.6M solution of n-butyl lithium in hexane, 14 ml (0.014 mol) of a 1M solution of $ZnCl_2$ in ether, and 1.26 mL (0.0133 mol) of methyl 2-bromoacetate to give after chromatography on silica (gradient, toluene→10% EtOAc/toluene) 2.1 g (66%) of 6-chloro-2-methyl-1H-indole-3-acetic acid methyl ester as an oil.

Analyses: Calc'd for $C_{12}H_{12}ClNO_2$: C, 60.64; H, 5.09; N, 5.89. Found: C, 60.78; H, 5.10; N, 5.84.

E. 6-Chloro-2-methyl-1-(phenylmethyl)-1H-indole-3-acetic acid methyl ester. Using the procedure described in Example 3 Part E, 1.0 g (0.00421 mol) of 6-chloro-2-methyl-1H-indole-3-acetic acid methyl ester was reacted with 0.472 g (0.00421 mol) of potassium t-butoxide and 0.48 mL (0.00421 mol) of benzyl chloride to give after silica chromatography (gradient, toluene→10% EtOAc/toluene) 0.97 g (70%) of 6-chloro-2-methyl-1-(phenylmethyl)-1H-indole-3-acetic acid methyl ester, mp, 92°–93° C.

Analyses: Calc'd for $C_{19}H_{18}ClNO_2$: C, 69.62; H, 5.54; N, 4.27. Found: C, 69.84; H, 5.49; N, 4.55.

F. 6-Chloro-2-methyl-1-(phenylmethyl)-1H-indole-3-acetic acid hydrazide. Using the method described in Example 1, Part G, 0.97 g (2.96 mmol) of 6-chloro-2-methyl-1-(phenylmethyl)-1H-indole-3-acetic acid methyl ester was reacted with 3 mL of hydrazine to give after crystallizing from MeOH 0.4 g (41% yield) of 6-chloro-2-methyl-1-(phenylmethyl)-1H-indole-3-acetic acid hydrazide, mp 179°–181° C.

Analyses: Calc'd for $C_{18}H_{18}ClN_3O$: C, 65.95; H, 5.54; N, 12.82. Found: C, 65.54 H, 5.47; N, 12.21.

Example 9

Preparation of 5-Benzyloxy-1-(phenylmethyl)-1H-indole-3-acetic acid hydrazide.

A. 5-Benzyloxy-1H-indole-3-acetic acid ethyl ester. As described in Example 1, Part E, 80 g (0.358 mol) of 5-benzyloxy-1H-indole was treated with 222 mL of 1.6M n-butyl lithium in hexane, 360 mL of 1M $ZnCl_2$ in ether, and 39.92 mL of ethyl 2-bromoacetate to give after chromatography on silica(gradient, toluene→5% EtOAc/toluene) 30 g (27% yield) of 5-benzyloxy-1H-indole-3-acetic acid ethyl ester, mp, 57°–59° C.

Analyses: Calc'd for $C_{19}H_{19}NO_3$: C, 73.77; H, 6.19; N, 5.43. Found: C, 73.75; H, 6.34; N, 4.50.

B. 5-Benzyloxy-1-(phenylmethyl)-1H-indole-3-acetic acid ethyl ester. Using the procedure described in Example 3 Part E, 6.18 g (0.02 mol) of 5-benzyloxy-1H-indole-3-acetic acid ethyl ester was reacted with 2.24 g (0.02 mol) of potassium t-butoxide and 2.3 mL (0.02 mol) of benzyl chloride to give after silica chromatography (gradient, toluene→6% EtOAc/toluene) 5.0 g (63%) of 5-benzyloxy-1-(phenylmethyl)-1H-indole-3-acetic acid ethyl ester, mp, 107°–109° C.

Analyses: Calc'd for $C_{26}H_{25}NO_3$: C, 78.17; H, 6.31; N, 3.51. Found: C, 78.46; H, 6.60; N, 3.59.

C. 5-Benzyloxy-1-(phenylmethyl)-1H-indole-3-acetic acid hydrazide. Using the method described in Example 1, Part G, 2.0 g (5 mmol) of 5-benzyloxy-1-(phenylmethyl)-1H-indole-3-acetic acid ethyl ester was reacted with 3 mL of hydrazine to give after crystallizing from MeOH 1.25 g (62% yield) of 5-benzyloxy-1-(phenylmethyl)-1H-indole-3-acetic acid hydrazide, mp 149°–150° C.

Analyses: Calc'd for $C_{24}H_{23}N_3O_2$: C, 74.78; H, 6.01; N, 10.90. Found: C, 74.91 H, 6.04; N, 10.97.

Example 10

Preparation of 2-Methyl-1-(phenylmethyl)-1H-indole-3-acetic acid hydrazide.

A. 2-Methyl-1H-indole-3-acetic acid methyl ester. To a solution of 25 g (0.132 mol) of 2-methyl-1H-indole-3-acetic acid in 500 mL of methanol was added 10 mL of methanesulfonic acid and the mixture stirred for 24 hours. The reaction mixture was diluted with water, extracted with EtOAc, the EtOAc solution was washed with water, $Na_2CO_3$ solution and with water. After drying over $Na_2SO_4$, the solvent was removed at reduced pressure to give 26.62 g (97% yield) of 2-methyl-1H-indole-3-acetic acid methyl ester as an oil.

Analyses: Calc'd for $C_{12}H_{13}NO_2$: C, 70.92; H, 6.45; N, 6.89. Found: C, 70.71 H, 6.48; N, 7.08.

B. 2-Methyl-1-(phenylmethyl)-1H-indole-3-acetic acid methyl ester. Using the procedure described in Example 3 Part E, 6.09 g (0.03 mol) of 2-methyl-1H-indole-3-acetic acid methyl ester was reacted with 3.36 g (0.03 mol) of potassium t-butoxide and 3.45 mL (0.03 mol) of benzyl chloride to give after silica chromatography(gradient, toluene→5% EtOAc/toluene) 6.0 g(68%) of 2-methyl-1-(phenylmethyl)-1H-indole-3-acetic acid methyl ester, mp, 71°–73° C.

Analyses: Calc'd for $C_{19}H_{19}NO_2$: C, 77.79; H, 6.53; N, 4.77. Found: C, 78.00; H, 6.51; N, 5.06.

C. 2-Methyl-1-(phenylmethyl)-1H-indole-3-acetic acid hydrazide. Using the method described in Example 1, Part G, 2.0 g (6.83 mmol) of 2-methyl-1-(phenylmethyl)-1H-indole-3-acetic acid ethyl ester was reacted with 5 mL of hydrazine to give after crystallizing from MeOH 1.2 g (60% yield) of 2-methyl-1-(phenylmethyl)-1H-indole-3-acetic acid hydrazide, mp 140°–143° C.

Analyses: Calc'd for $C_{18}H_{19}N_3O$: C, 73.70; H, 6.53; N, 14.32. Found: C, 73.95; H, 6.76; N, 14.60.

Example 11

Preparation of 1-(2-Methoxy-1-naphthalenylmethyl)-2-methyl-1H-indole-3-acetic acid hydrazide.

A. 1-(2-Methoxy-1-naphthalenylmethyl)-2-methyl-1H-indole-3-acetic acid methyl ester. Using the procedure described in Example 3 Part E, 4.06 g (0.02 mol) of 2-methyl-1H-indole-3-acetic acid methyl ester was reacted with 2.24 g (0.03 mol) of potassium t-butoxide and 4.13 g (0.02 mol) of 1-chloromethyl-2-methoxynaphthalene to give after silica chromatography (gradient, toluene→5% EtOAc/toluene) 4.95 g (66%) of 1-(2-methoxy-1-naphthalenylmethyl)-2-methyl-1H-indole-3-acetic acid methyl ester, mp, 120°–123° C.

Analyses: Calc'd for $C_{24}H_{23}NO_3$: C, 77.19; H, 6.21; N, 3.75. Found: C, 77.45; H, 6.27; N, 3.69.

B. 1-(2-Methoxy-1-naphthalenylmethyl)-2-methyl-1H-indole-3-acetic acid hydrazide. Using the method described in Example 1, Part G, 4.9 g (0.0131 mol) of 2-methyl-1-(2-methoxy-1-naphthalenylmethyl)-1H-indole-3-acetic acid methyl ester was reacted with 10 mL of hydrazine to give after crystallizing from MeOH/CH$_2$Cl$_2$ 3.02 g (62% yield) of 2-methyl-1-(2-methoxy-1-naphthalenylmethyl)-1H-indole-3-acetic acid hydrazide, mp 201°–203° C.

Analyses: Calc'd for $C_{23}H_{23}N_3O_2$: C, 73.97; H, 6.21; N 11.52. Found: C, 74.24; H, 6.28; N, 11.51.

Example 12

Preparation of 1-([1,1'-Biphenyl]-2-ylmethyl)-5-methoxy-1H-indole-3-acetic acid hydrazide.

A. 1-([1,1'-Biphenyl]-2-ylmethyl)-5-methoxy-1H-indole-3-acetic acid ethyl ester. Using the procedure described in Example 1 Part F, 1.2 g (5 mmol) of 5-methoxy-1H-indole-3-acetic acid ethyl ester was reacted with 200 mg (5 mmol) of 60% NaH/mineral oil, and 0.9 mL (5 mmol) of 2-chloromethylbiphenyl to give after silica chromatography(20% EtOAc/hexane) 1.15 g (58%) of 1-([1,1'-biphenyl]-2-ylmethyl)-5-methoxy-1H-indole-3-acetic acid ethyl ester as an oil.

Analyses: Calc'd for $C_{26}H_{25}NO_3$: C, 78.17; H, 6.31; N, 3.51. Found: C, 78.81; H, 6.28; N, 3.47.

B. 1-([1,1'-Biphenyl]-2-ylmethyl)-5-methoxy-1H-indole-3-acetic acid hydrazide. Using the method described in Example 1, Part G, 859 mg (2.15 mmol) of 1-([1,1'-biphenyl]-2-ylmethyl)-5-methoxy-1H-indole-3-acetic acid ethyl ester was reacted with 2.5 mL of hydrazine to give after crystallizing from MeOH/hexane 300 mg (36% yield) of 1-([1,1'-Biphenyl]-2-ylmethyl)-5-methoxy-1H-indole-3-acetic acid hydrazide, mp 123°–125° C.

Analyses: Calc'd for $C_{24}H_{23}N_3O_2$: C, 74.78; H, 6.01; N, 10.90. Found: C, 75.01 H, 6.27; N, 10.87.

Example 13

Preparation of 5-Methoxy-2-methyl-1-(2-methyl-1-propyl)-1H-indole-3-acetic acid hydrazide.

A. 5-Methoxy-2-methyl-1H-indole-3-acetic acid ethyl ester. Dry hydrogen chloride was bubbled into a solution of 27.95 g (0.16 mol) of 4-methoxyphenylhydrazine hydrochloride and 19.72 g (0.17 mol) of levulinic acid in 500 mL of ethanol for 0.5 hour while cooling with an ice-water bath. The bath was removed and the reaction slowly heated to reflux and reflux maintained for 20 hours. After cooling the mixture was poured into water and extracted with EtOAc. The EtOAc solution was washed with sodium bicarbonate solution and dried over Na$_2$SO$_4$. After removing the solvent at reduced pressure, the residue was chromatographed over silica eluting with 5% EtOAc/toluene to give 14.2 g (36% yield) of 5-methoxy-2-methyl-1H-indole-3-acetic acid ethyl ester, mp, 38°–40° C.

Analyses: Calc'd for $C_{14}H_{17}NO_3$: C, 67.99; H, 6.93; N, 5.66. Found: C, 68.24 H, 6.88; N, 5.75.

B. 5-Methoxy-2-methyl-1-(2-methyl-1-propyl)-1H-indole-3-acetic acid ethyl ester. A solution of 2.06 g (8.34 mmol) of 5-methoxy-2-methyl-1H-indole-3-acetic acid ethyl ester, 3 g of potassium carbonate, and 3 mL of 2-methyl-1-propyl iodide was heated at 65° C. for 96 hours, and the mixture poured into water. The product was extracted with EtOAc and the EtOAc washed four times with water and dried over Na$_2$SO$_4$. Silica chromatograpy eluting with a gradient, toluene→10% EtOAc/toluene, gave 0.26 g (10% yield) of 5-methoxy-2-methyl-1-(2-methyl-1-propyl)-1H-indole-3-acetic acid ethyl ester as an oil.

C. 5-Methoxy-2-methyl-1-(2-methyl-1-propyl)-1H-indole-3-acetic acid hydrazide. As described in Example 1, Part G, 230 mg (0.76 mmol) of 5-methoxy-2-methyl-1-(2-methyl-1-propyl)-1H-indole-3-acetic acid ethyl ester and 1 mL of hydrazine were reacted to give upon recrystallization from MeOH, 10 mg (4.5% yield) of 5-methoxy-2-methyl-1-(2-methyl-1-propyl)-1H-indole-3-acetic acid hydrazide, mp, 113°–116° C.

Analyses: Calc'd for $C_{16}H_{23}N_3O_2$: C, 66.41; H, 8.01; N, 14.52. Found: C, 65.79 H, 8.10; N, 14.16.

Example 14

Preparation of 1-Decyl-5-methoxy-2-methyl-1H-indole-3-acetic acid hydrazide.

A. 1-Decyl-5-methoxy-2-methyl-1H-indole-3-acetic acid ethyl ester. Using the procedure described in Example 3 Part E, 2.47 g (0.01 mol) of 5-methoxy-2-methyl-1H-indole-3-acetic acid ethyl ester was reacted with 1.12 g (0.01 mol) of potassium t-butoxide and 2.07 mL (0.01 mol) of decyl bromide to give after silica chromatography (gradient, toluene→5% EtOAc/toluene) 2.16 g (56%) of 1-decyl-5-methoxy-2-methyl-1H-indole-3-acetic acid ethyl ester as an oil.

Analyses: Calc'd for $C_{24}H_{37}NO_3$: C, 74.38; H, 9.62; N, 3.61. Found: C, 74.53; H, 9.38; N, 3.57.

B. 1-Decyl-5-methoxy-2-methyl-1H-indole-3-acetic acid hydrazide. As described in Example 1, Part G, 2.1 g (0.00545 mol) of 1-decyl-5-methoxy-2-methyl-1H-indole-3-acetic acid ethyl ester and 5 mL of hydrazine were reacted to give upon recrystallization from MeOH, 0.65 g (32% yield) of 1-decyl-5-methoxy-2-methyl-1H-indole-3-acetic acid hydrazide, mp, 129°–131° C.

Analyses: Calc'd for $C_{22}H_{35}N_3O_2$: C, 70.74; H, 9.44; N, 11.25. Found: C, 70.79; H, 9.60; N, 11.13.

Example 15

Preparation of 5-Methoxy-2-methyl-1-octadecyl-1H-indole-3-acetic acid hydrazide.

A. 5-Methoxy-2-methyl-1-octadecyl-1H-indole-3-acetic acid methyl ester. Using the procedure described in Example 1, Part F, 494 mg (2 mmol) of 5-methoxy-2-methyl-1H-indole- 3-acetic acid ethyl ester was reacted with 80 mg (2 mmol) of 60% NaH/mineral oil and 667 mg (2 mmol) of octadecyl bromide to give after crystallization from MeOH 648 mg (65%) of 5-methoxy-2-methyl-1-octadecyl-1H-indole-3-acetic acid methyl ester,mp, 68°–69° C.

Analyses: Calc'd for $C_{32}H_{53}NO_3$: C, 76.91; H, 10.69; N, 2.80. Found: C, 76.71; H, 10.50; N, 2.99.

B. 5-Methoxy-2-methyl-1-octadecyl-1H-indole-3-acetic acid hydrazide. Using the method described in Example 1, Part G, 250 mg (0.5 mmol) of 5-methoxy-2- methyl-1-octadecyl-1H-indole-3-acetic acid methyl ester was reacted with 0.5 mL of hydrazine to give after crystallizing from the reaction mixture 130 mg (54% yield) of 5-methoxy-2-methyl-1-octadecyl-1H-indole-3-acetic acid hydrazide, mp 121°–123° C.

Analyses: Calc'd for $C_{30}H_{51}N_3O_2$: C, 74.18; H, 10.58; N, 8.65. Found: C, 74.45 H, 10.64; N, 8.63.

Example 16

Preparation of 5-Methoxy-2-methyl-1-(phenylmethyl)-1H-indole-3-acetic acid hydrazide.

A. 5-Methoxy-2-methyl-1-(phenylmethyl)-1H-indole-3-acetic acid ethyl ester. Using the procedure described in Example 3 Part E, 4.07 g (0.0165 mol) of 5-methoxy-2-methyl-1H-indole-3-acetic acid ethyl ester was reacted with 1.85 g (0.0165 mol) of potassium t-butoxide and 1.96 mL (0.0165 mol) of benzyl chloride to give after silica chromatography(gradient, toluene→10% EtOAc/toluene) 3.78 g (68% yield) of 5-methoxy-2-methyl-1-(phenylmethyl)-1H-indole-3-acetic acid ethyl ester, mp, 63°–64° C.

Analyses: Calc'd for $C_{21}H_{23}NO_3$: C, 74.75; H, 6.87; N, 4.15. Found: C, 74.76; H, 6.89; N, 4.28.

B. 5-Methoxy-2-methyl-1-(phenylmethyl)-1H-indole-3-acetic acid hydrazide. A solution of 1.0 g (2.96 mmol) of 5-methoxy-2-methyl-1-(phenylmethyl)-1H-indole-3-acetic acid ethyl ester and 5 mL of hydrazine in 50 mL of MeOH was heated to maintain reflux for 8 h, cooled, diluted with water and extracted with EtOAc. The EtOAc solution was washed with saturated NaCl solution and dried over $Na_2SO_4$. The solvent was evaporated at reduced pressure and the residue triturated with ether to give 920 mg (96% yield) of 5-methoxy-2-methyl-1-(phenylmethyl)-1H-indole-3-acetic acid hydrazide, mp, 161°–162° C.

Analyses: Calc'd for $C_{19}H_{21}N_3O_2$: C, 70.53; H, 6.54; N, 12.99. Found: C, 70.41; H, 6.58; N, 12.93.

Example 17

Preparation of 1-(2-Chlorophenylmethyl)-5-methoxy-2-methyl-1H-indole-3-acetic acid hydrazide.

A. 1-(2-Chlorophenylmethyl)-5-methoxy-2-methyl-1H-indole-3-acetic acid ethyl ester. Using the procedure described in Example 1 Part F, 494 mg (2 mmol) of 5-methoxy-2-methyl-1H-indole-3-acetic acid ethyl ester was reacted with 80 mg (2 mmol) of 60% NaH/mineral oil and 0.25 mL (2 mmol) of ortho-chlorobenzylchloride and after chromatography on silica (eluting with 30% EtOAc/hexane) and crystallizing with MeOH there was obtained 414 mg (56%) of 1-(2-chlorophenylmethyl)-5-methoxy-2-methyl-1H-indole-3-acetic acid ethyl ester, mp, 74°–77° C.

Analyses: Calc'd for $C_{21}H_{22}ClNO_3$: C, 67.83; H, 5.95; N, 3.77. Found: C, 67.88; H, 6.09; N, 3.84.

B. 1-(2-Chlorophenylmethyl)-5-methoxy-2-methyl-1H-indole-3-acetic acid hydrazide. Using the method described in Example 1, Part G, 395 mg (1.06 mmol) of 1-(2-chlorophenylmethyl)-5-methoxy-2-methyl-1H-indole-3-acetic acid ethyl ester was reacted with 1.0 mL of hydrazine to give after crystallizing from MeOH 200 mg (53% yield) of 1-(2-chlorophenylmethyl)-5-methoxy-2-methyl-1H-indole-3-acetic acid hydrazide, mp 99°–100.5° C.

Analyses: Calc'd for $C_{19}H_{20}ClN_3O_2$: C, 63.77; H, 5.63; N, 11.74. Found: C, 63.51 H, 5.77; N, 11.45

Example 18

Preparation of 1-(3-Chlorophenylmethyl)-5-methoxy-2-methyl-1H-indole-3-acetic acid hydrazide.

A. 1-(2-Chlorophenylmethyl)-5-methoxy-2-methyl-1H-indole-3-acetic acid ethyl ester. Using the procedure described in Example 1, Part F, 494 mg (2 mmol) of 5-methoxy-2-methyl-1H-indole-3-acetic acid ethyl ester was reacted with 80 mg (2 mmol) of 60% NaH/mineral oil and 0.25 mL (2 mmol) of meta-chlorobenzylchloride and after chromatography on silica (eluting with 33% EtOAc/hexane) and crystallizing from MeOH there was obtained 409 mg (55%) of 1-(3-chlorophenylmethyl)-5-methoxy-2-methyl-1H-indole-3-acetic acid ethyl ester, mp, 79°–81° C.

Analyses: Calc'd for $C_{21}H_{22}ClNO_3$: C, 67.83; H, 5.95; N, 3.77. Found: C, 67.55; H, 5.95; N, 3.76.

B. 1-(3-Chlorophenylmethyl)-5-methoxy-2-methyl-1H-indole-3-acetic acid hydrazide. Using the method described in Example 1, Part G, 395 mg (1.06 mmol) of 1-(3-Chlorophenylmethyl)-5-methoxy-2-methyl-1H-indole-3-acetic acid ethyl ester was reacted with 1.0 mL of hydrazine to give after crystallizing from MeOH 257 mg (68% yield) of 1-(3-Chlorophenylmethyl)-5-methoxy-2-methyl-1H-indole-3-acetic acid hydrazide, mp 139°–140° C.

Analyses: Calc'd for $C_{19}H_{20}ClN_3O_2$: C, 63.77; H, 5.63; N, 11.74. Found: C, 63.79 H, 5.69; N, 11.67.

Example 19

Preparation of 1-(4-Chlorophenylmethyl)-5-methoxy-2-methyl-1H-indole-3-acetic acid hydrazide.

A. 1-(4-Chlorophenylmethyl)-5-methoxy-2-methyl-1H-indole-3-acetic acid ethyl ester. Using the procedure described in Example 1 Part F, 494 mg (2 mmol) of 5-methoxy-2-methyl-1H-indole-3-acetic acid ethyl ester was reacted with 80 mg (2 mmol) of 60% NaH/mineral oil and 322 mg (2 mmol) of para-chlorobenzylchloride and after chromatography on silica (eluting with 30% EtOAc/hexane) and crystallizing with MeOH there was obtained 348 mg (47%) of 1-(4-chlorophenylmethyl)-5-methoxy-2-methyl-1H-indole-3-acetic acid ethyl ester, mp, 98°–100° C.

Analyses: Calc'd for $C_{21}H_{22}ClNO_3$: C, 67.83; H, 5.95; N, 3.77. Found: C, 67.98; H, 5.92; N, 3.69.

B. 1-(4-Chlorophenylmethyl)-5-methoxy-2-methyl-1H-indole-3-acetic acid hydrazide. Using the method described in Example 1, Part G, 333 mg (0.9 mmol) of 1-(4-chlorophenylmethyl)-5-methoxy-2-methyl-1H-indole-3-acetic acid ethyl ester was reacted with 1.0 mL of hydrazine to give after crystallizing from MeOH 251 mg (78% yield) of 1-(4-chlorophenylmethyl)-5-methoxy-2-methyl-1H-indole-3-acetic acid hydrazide, mp 177°–180° C.

Analyses: Calc'd for $C_{19}H_{20}ClN_3O_2$: C, 63.77; H, 5.63; N, 11.74. Found: C, 64.02 H, 5.77; N, 11.45.

Example 20

Preparation of 1-(2,5-Dichlorophenylmethyl)-5-methoxy-2-methyl-1H-indole-3-acetic acid hydrazide.

A. 1-(2,5-Dichlorophenylmethyl)-5-methoxy-2-methyl-1H-indole-3-acetic acid ethyl ester. Using the procedure described in Example 1, Part F, 494 mg (2 mmol) of 5-methoxy-2-methyl-1H-indole-3-acetic acid ethyl ester was reacted with 80 mg (2 mmol) of 60% NaH/mineral oil and 391 mg (2 mmol) of (2,5-dichlorophenyl)methyl chloride and after chromatography on silica (eluting with 20% EtOAc/hexane) and crystallizing with MeOH there was obtained 236 mg (29%) of 1-(2,5-dichlorophenylmethyl)-5-methoxy-2-methyl-1H-indole-3-acetic acid ethyl ester, mp, 146°–148° C.

Analyses: Calc'd for $C_{21}H_{21}Cl_2NO_3$: C, 62.08; H, 5.21; N, 3.45. Found: C, 62.34; H, 5.23; N, 3.72.

B. 1-(2,5-Dichlorophenylmethyl)-5-methoxy-2-methyl-1H-indole-3-acetic acid hydrazide. Using the method described in Example 1, Part G, 221 mg (0.54 mmol) of 1-(2,5-dichlorophenylmethyl)-5-methoxy-2-methyl-1H-indole-3-acetic acid ethyl ester was reacted with 0.6 mL of hydrazine to give after crystallizing from MeOH 135 mg (64% yield) of 1-(2,5-dichlorophenylmethyl)-5-methoxy-2-methyl-1H-indole-3-acetic acid hydrazide, mp 168°–170° C.

Analyses: Calc'd for $C_{19}H_{19}Cl_2N_3O_2$: C, 58.17; H, 4.88; N, 10.71. Found: C, 58.46; H, 4.94; N, 10.73.

Example 21

Preparation of 1-(2,6-Dichlorophenylmethyl)-5-methoxy-2-methyl-1H-indole-3-acetic acid hydrazide.

A. 1-(2,6-Dichlorophenylmethyl)-5-methoxy-2-methyl-1H-indole-3-acetic acid ethyl ester. Using the procedure described in Example 1 Part F, 494 mg (2 mmol) of 5-methoxy-2-methyl-1H-indole-3-acetic acid ethyl ester was reacted with 80 mg (2 mmol) of 60% NaH/mineral oil and 391 mg (2 mmol) of (2,6-dichlorophenyl) methyl chloride and after chromatography on silica (eluting with 25% EtOAc/hexane) there was obtained 556 mg (68%) of 1-(2, 6-dichlorophenylmethyl)-5-methoxy-2-methyl-1H-indole-3-acetic acid ethyl ester, mp, 131°–131° C.

Analyses: Calc'd for $C_{21}H_{21}Cl_2NO_3$: C, 62.08; H, 5.21; N, 3.45. Found: C, 61.79; H, 5.23; N, 3.751.

B. 1-(2,6-Dichlorophenylmethyl)-5-methoxy-2-methyl-1H-indole-3-acetic acid hydrazide. Using the method described in Example 1, Part G, 533 mg (1.3 mmol) of 1-2,6-dichlorophenylmethyl)-5-methoxy-2-methyl-1H-indole-3-acetic acid ethyl ester was reacted with 1.3 mL of hydrazine to give after crystallizing from MeOH 250 mg (61% yield) of 1-(2,6-dichlorophenylmethyl)-5-methoxy-2-methyl-1H-indole-3-acetic acid hydrazide, mp 194°–196° C.

Analyses: Calc'd for $C_{19}H_{19}Cl_2N_3O_2$: C, 58.17; H, 4.88; N, 10.71. Found: C, 58.65; H, 4.98; N, 10.68.

Example 22

Preparation of 5-Methoxy-1-[(3-methylphenyl)methyl]-2-methyl-1H-indole-3-acetic acid hydrazide.

A. 5-Methoxy-1-[(3-methylphenyl)methyl]-2-methyl-1H-indole-3-acetic acid ethyl ester. Using the procedure described in Example 1 Part F, 494 mg (2 mmol) of 5-methoxy-2-methyl-1H-indole-3-acetic acid ethyl ester was reacted with 80 mg (2 mmol) of 60% NaH/mineral oil and 0.26 mL (2 mmol) of meta-methylbenzylchloride and after chromatography on silica (eluting with 20% EtOAc/hexane) there was obtained 438 mg (62%) of 5-methoxy-1-[(3-methylphenyl)methyl]-2-methyl-1H-indole-3-acetic acid ethyl ester as an oil.

Analyses: Calc'd for $C_{22}H_{25}NO_3$: C, 75.19; H, 7.17; N, 3.99. Found: C, 75.46; H, 7.29; N, 3.97.

B. 5-Methoxy-1-[(3-methylphenyl)methyl]-2-methyl-1H-indole-3-acetic acid hydrazide. Using the method described in Example 1, Part G, 409 mg (1.17 mmol) of 5-methoxy-1-[(3-methylphenyl)methyl]-2-methyl-1H-indole-3-acetic acid ethyl ester was reacted with 1.2 mL of hydrazine to give after crystallizing from MeOH 157 mg (40% yield) of 5-methoxy-1-[(3-methylphenyl)methyl]-2-methyl-1H-indole-3-acetic acid hydrazide, mp 133°–135° C.

Analyses: Calc'd for $C_{20}H_{23}N_3O_2$: C, 71.19 H, 6.87; N, 12.45. Found: C, 71.42; H, 6.97; N, 12.66.

Example 23

Preparation of 5-Methoxy-2-methyl-1-[(3-trifluoromethylphenyl)methyl]-1H-indole-3-acetic acid hydrazide.

A. 5-Methoxy-2-methyl-1-[(3-trifluoromethylphenyl)methyl]-1H-indole-3-acetic acid ethyl ester. Using the procedure described in Example 1 Part F, 494 mg (2 mmol) of 5-methoxy-2-methyl-1H-indole-3-acetic acid ethyl ester was reacted with 80 mg (2 mmol) of 60% NaH/mineral oil and 389 mg (2 mmol) of meta-trifluoromethylbenzylchloride and after chromatography on silica(eluting with 20% EtOAc/hexane) and crystallization from MeOH there was obtained 410 mg (51%) of 5-methoxy-2-methyl-1-[(3-trifluoromethylphenyl)methyl]-1H-indole-3-acetic acid ethyl ester, mp 95°–97° C.

Analyses: Calc'd for $C_{22}H_{22}F_3NO_3$: C, 65.18; H, 5.47; N, 3.46. Found: C, 65.41; H, 5.53 N, 3.60.

B. 5-Methoxy-2-methyl-1-[(3-trifluoromethylphenyl)methyl]-1H-indole-3-acetic acid hydrazide. Using the method described in Example 1, Part G, 390 mg (0.96 mmol) of 5-methoxy-2-methyl-1-[(3-trifluoromethylphenyl)methyl]-1H-indole-3-acetic acid ethyl ester was reacted with 1.2 mL of hydrazine to give after crystallizing from MeOH 166 mg (44% yield) of 5-methoxy-2-methyl-1-[(3-trifluoromethylphenyl)methyl]-1H-indole-3-acetic acid hydrazide, mp 162°–165° C.

Analyses: Calc'd for $C_{20}H_{20}F_3N_3O_2$: C, 61.38 H, 5.15; N, 10.74. Found: C, 61.58; H, 5.24; N, 10.95.

Example 24

Preparation of 1-([1,1'-Biphenyl]-2-ylmethyl)-5-methoxy-2-methyl-1H-indole-3-acetic acid hydrazide.

A. 1-([1,1'-Biphenyl]-2-ylmethyl)-5-methoxy-2-methyl-1H-indole-3-acetic acid ethyl ester. Applying the procedures in Example 1 Part F, 483 mg (2 mmol) of 5-methoxy-2-methyl-1H-indole-3-acetic acid methyl ester was treated with 80 mg (2 mmol) of 60% NaH/mineral oil and 0.37 mL (2 mmol) of 2-(bromomethyl)biphenyl to give after chromatography on silica (elution with 25% EtOAc/hexane), 567 mg (69% yield) of 1-([1,1'-biphenyl]-2-ylmethyl)-5-methoxy-2-methyl-1H-indole-3-acetic acid ethyl ester as a yellow oil.

Analyses: Calc'd for $C_{27}H_{27}NO_3$: C, 78.42; H, 6.58; N, 3.39. Found: C, 78.12; H, 6.47; N, 3.03.

B. 1-([1,1'-Biphenyl]-2-ylmethyl)-5-methoxy-2-methyl-1H-indole-3-acetic acid hydrazide. Using the method described in Example 1, Part G, 552 mg (1.34 mmol) of 1-([1,1'-biphenyl]-2-ylmethyl)-5-methoxy-2-methyl-1H-indole-3-acetic acid ethyl ester was reacted with 2.0 mL of hydrazine to give after chromatography on silica (eluted with EtOAc) 150 mg (28% yield) of 1-([1,1'-biphenyl]-2-ylmethyl)-5-methoxy-2-methyl-1H-indole-3-acetic acid hydrazide.

Analyses: Calc'd for $C_{25}H_{25}N_3O_2$: C, 75.16; H, 6.31; N, 10.52. Found: C, 75.01 H, 6.34; N, 10.26.

Example 25

Preparation of 1-([1,1'-Biphenyl]-3-ylmethyl)-5-methoxy-2-methyl-1H-indole-3-acetic acid hydrazide.

A. 1-([1,1'-Biphenyl]-3-ylmethyl)-5-methoxy-2-methyl-1H-indole-3-acetic acid ethyl ester. Applying the procedures in Example 1 Part F, 483 mg (2 mmol) of 5-methoxy-2-methyl-1H-indole-3-acetic acid methyl ester was treated with 80 mg (2 mmol) of 60% NaH/mineral oil and 405 mg (2 mmol) of 3-(chloromethyl)-biphenyl to give after chromatography on silica(elution with 33% EtOAc/hexane), 510 mg (62% yield) of 1-([1,1'-biphenyl]-3-ylmethyl)-5-methoxy-2-methyl-1H-indole-3-acetic acid ethyl ester as a yellow oil.

B. 1-([1,1'-Biphenyl]-3-ylmethyl)-5-methoxy-2-methyl-1H-indole-3-acetic acid hydrazide. Using the method described in Example 1, Part G, 490 mg (1.2 mmol) of 1-([1,1'-biphenyl]-3-ylmethyl)-5-methoxy-2-methyl-1H-indole-3-acetic acid ethyl ester was reacted with 1.2 mL of hydrazine to give after crystallization from MeOH 316 mg (66% yield) of 1-[1,1'-biphenyl]-3-ylmethyl)-5-methoxy-2-methyl-1H-indole-3-acetic acid hydrazide.

Analyses: Calc'd for $C_{25}H_{25}N_3O_2$: C, 75.16; H, 6.31; N, 10.52. Found: C, 74.96 H, 6.32; N, 10.28.

Example 26

Preparation of 5-Methoxy-1-[(2-methoxyphenyl)methyl]-2-methyl-1H-indole-3-acetic acid hydrazide.

A. 5-Methoxy-1-[(2-methoxyphenyl)methyl]-2-methyl-1H-indole-3-acetic acid. Using the procedure described in Example 1, Part F, 2.0 g (8.12 mmol) of 5-methoxy-2-methyl-1H-indole-3-acetic acid ethyl ester was reacted with 325 mg (8.12 mmol) of 60% NaH/mineral oil and 1.272 g (8.12 mmol) of ortho-methoxybenzylchloride and after chromatography on silica (eluting with 25% EtOAc/hexane) there was obtained 1.74 g (52%) of 5-methoxy-1-[(2-methoxyphenyl)methyl]-2-methyl-1H-indole-3-acetic acid ethyl ester as an oil. This oil (1.74 g) in 30 mL of MeOH and 15 mL of 1N NaOH was heated to maintain reflux for 20 hours. The mixture was diluted with water, extracted with EtOAc, then the EtOAc solution was dried ($Na_2SO_4$), the solvent removed at reduced pressure and the residue crystallized from MeOH to give 1.1 g (68% yield) of 5-methoxy-1-[(2-methoxyphenyl)methyl]-2-methyl-1H-indole-3-acetic acid, mp 176°–180° C.

Analyses: Calc'd for $C_{22}H_{21}NO_4$: C, 70.78; H, 6.24; N, 4.13. Found: C, 70.98; H, 6.42; N, 4.19.

B. 5-Methoxy-1-[(2-methoxyphenyl)methyl]-2-methyl-1H-indole-3-acetic acid methyl ester. Using the procedure described in Example 10, Part A, 848 mg (2.5 mmol) of 5-methoxy- 1-[(2-methoxyphenyl)methyl]-2-methyl-1H-indole-3-acetic acid was treated with 0.2 mL of methanesulfonic acid in 20 mL of MeOH to give after chromatography on silica (eluting with 20% EtOAc/hexane) 655 mg (74%) of 5-methoxy-1-[(2-methoxyphenyl)methyl]-2-methyl-1H-indole-3-acetic acid methyl ester, mp 98°–100° C.

Analyses: Calc'd for $C_{21}H_{23}NO_4$: C, 71.37; H, 6.56; N, 3.96. Found: C, 71.59; H, 6.74; N, 3.81.

C. 5-Methoxy-1-[(2-methoxyphenyl)methyl]-2-methyl-1N-indole-3-acetic acid hydrazide. Using the method described in Example 1, Part G, 640 mg (1.8 mmol) of 5-methoxy-1-[(2-methoxyphenyl)methyl]-2-methyl-1H-indole-3-acetic acid methyl ester was reacted with 2.0 mL of hydrazine to give after crystallizing from MeOH 358 mg (56% yield) of 5-methoxy-1-[(2-methoxy-phenyl)methyl]-2-methyl-1H-indole-3-acetic acid hydrazide, mp 140°–143° C.

Analyses: Calc'd for $C_{20}H_{23}N_3O_3$: C, 67.97H, 6.56; N, 11.89. Found: C, 68.84; H, 6.67; N, 11.84.

Example 27

Preparation of 5-Methoxy-1-[(3-methoxyphenyl)methyl]-2-methyl-1H-indole-3-acetic acid hydrazide.

A. 5-Methoxy-1-[(3-methoxyphenyl)methyl]-2-methyl-1H-indole-3-acetic acid ethyl ester. Using the procedure described in Example 1 Part F, 494 mg (2 mmol) of 5-methoxy-2-methyl-1H-indole-3-acetic acid ethyl ester was reacted with 80 mg (2 mmol) of 60% NaH/mineral oil and 313 mg (2 mmol) of meta-methoxybenzylchloride and after chromatography on silica (eluting with 20% EtOAc/hexane) there was obtained after crystallizing from MeOH, 424 mg (58%) of 5-methoxy-1-[(3-methoxyphenyl)methyl] -2-methyl-1H-indole-3-acetic acid ethyl ester, mp 88°–90° C.

Analyses: Calc'd for $C_{22}H_{25}NO_4$: C, 71.91; H, 6.86; N, 3.81. Found: C, 72.05; H, 6.99; N, 4.07.

B. 5-Methoxy-1-[(3-methoxyphenyl)methyl]-2-methyl-1H-indole-3-acetic acid hydrazide. Using the method described in Example 1, Part G, 406 mg (1.1 mmol) of 5-methoxy-1-[(3-methoxyphenyl)methyl]-2-methyl-1H-indole-3-acetic acid ethyl ester was reacted with 1.0 mL of hydrazine to give after crystallizing from MeOH 240 mg (62% yield) of 5-methoxy-1-[(3-methoxy-phenyl)methyl]-2- methyl-1H-indole-3-acetic acid hydrazide, mp 161°–163° C.

Analyses: Calc'd for $C_{20}H_{23}N_3O_3$: C, 67.97H, 6.56; N, 1.89. Found: C, 68.00; H, 6.61; N, 12.02.

Example 28

Preparation of 5-Methoxy-1-[(4-methoxyphenyl)methyl]-2-methyl-1H-indole-3-acetic acid hydrazide.

A. 5-Methoxy-1-[(4-methoxyphenyl)methyl]-2-methyl-1H-indole-3-acetic acid ethyl ester. Using the procedure described in Example 1, Part F, 494 mg (2 mmol) of 5-methoxy-2-methyl-1H-indole-3-acetic acid ethyl ester was reacted with 80 mg (2 mmol) of 60% NaH/mineral oil and 0.3 mL (2 mmol) of para-methoxybenzylchloride and after chromatography on silica (eluting with 25% EtOAc/hexane) there was obtained 341 mg (46%) of 5-methoxy-1-[(4-methoxyphenyl)methyl]-2-methyl-1H-indole-3-acetic acid ethyl ester as an oil.

Analyses: Calc'd for $C_{22}H_{25}NO_4$: C, 71.91; H, 6.86; N, 3.81. Found: C,72.62 ; H, 6.75; N, 3.41

B. 5-Methoxy-1-[(4-methoxyphenyl)methyl]-2-methyl-1H-indole-3-acetic acid hydrazide. Using the method described in Example 1, Part G, 317 mg (0.86 mmol ) of 5-methoxy-1-[(4-methoxyphenyl)methyl]-2-methyl-1H-indole-3-acetic acid ethyl ester was reacted with 1.0 mL of hydrazine to give after crystallizing from MeOH 124 mg (41% yield) of 5-methoxy-1-[(4-methoxy-phenyl)methyl]-2-methyl-1H-indole-3-acetic acid hydrazide, mp 161°–163° C.

Analyses: Calc'd for $C_{20}H_{23}N_3O_3$: C, 67.97H, 6.56; N, 11.89. Found: C, 68.21; H, 6.65; N, 11.95.

Example 29

Preparation of 1-[(3-Decyloxyphenyl)methyl]-5-methoxy-2-methyl-1H-indole-3-acetic acid hydrazide.

A. 1-[(3-Decyloxyphenyl)methyl]-5-methoxy-2-methyl-1H-indole -3-acetic acid ethyl ester. Using the procedure described in Example 1, Part F, 494 mg (2 mmol) of 5-methoxy-2-methyl-1H-indole-3-acetic acid ethyl ester was reacted with 80 mg (2 mmol) of 60% NaH/mineral oil and 565 mg (2 mmol) of meta-decyloxybenzylchloride and after chromatography on silica (eluting with 20% EtOAc/hexane) there was obtained 590 mg (60%) of 1-[(3-decyloxyphenyl)methyl]-5-methoxy-2-methyl-1H-indole-3-acetic acid ethyl ester as an oil.

Analyses: Calc'd for $C_{31}H_{43}NO_4$: C, 75.42; H, 8.78; N, 2.84. Found: C, 75.21; H, 9.00; N, 2.78.

B. 1-[(3-Decyloxyphenyl)methyl]-5-methoxy-2-methyl-1H-indole-3-acetic acid hydrazide. Using the method described in Example 1, Part G, 571 mg (1.16 mmol) of 1-[(3-decyloxyphenyl)methyl]-5-methoxy-2-methyl-1H-indole-3-acetic acid ethyl ester was react ed with 1.5 mL of hydrazine to give after crystalling from MeOH 188 mg (34% yield) of 1-[(3-decyloxyphenyl)methyl]-5-methoxy-2-methyl-1H-indole-3-acetic acid hydrazide, mp 66°–76° C.

Analyses: Calc'd for $C_{29}H_{41}N_3O_3$: C, 72.62H, 8.62; N, 8.76. Found: C, 72.92; H, 8.66; N, 6.99.

Example 30

Preparation of 1-[(3-Benzyloxyphenyl)methyl]-5-methoxy-2-methyl-1H-indole-3-acetic acid hydrazide.

A. 1-[(3-Benzyloxyphenyl)methyl]-5-methoxy-2-methyl-1H-indole-3-acetic acid ethyl ester. Using the procedure described in Example 1 Part F, 494 mg (2 mmol) of 5-methoxy-2-methyl-1H-indole-3-acetic acid ethyl ester was reacted with 80 mg (2 mmol) of 60% NaH/mineral oil and 465 mg (2 mmol) of meta-benzyloxybenzyl chloride and after chromatography on silica (eluting with 20% EtOAc/hexane) and crystallizing from MeOH there was obtained 376 mg (42%) of 1-[(3-benzyloxyphenyl)methyl]-5-methoxy-2-methyl-1H-indole-3-acetic acid, mp, 60°–70° C.

Analyses: Calc'd for $C_{28}H_{29}NO_4$: C, 75.82; H, 6.59; N, 3.16. Found: C, 76.06; H, 6.56; N, 3.35.

B. 1-[(3-Benzyloxyphenyl)methyl]-5-methoxy-2-methyl-1H-indole-3-acetic acid hydrazide. Using the method described in Example 1, Part G, 369 mg (0.83 mmol) of 1-[(3-benzyloxyphenyl)methyl]-5-methoxy-2-methyl-1H-indole-3-acetic acid ethyl ester was reacted with 0.83 mL of hydrazine to give after crystalling from MeOH 180 mg (51% yield) of 1-[(3-benzyloxyphenyl)methyl]-5-methoxy-2-methyl-1H-indole-3-acetic acid hydrazide, mp, 130°–132° C.

Analyses: Calc'd for $C_{26}H_{27}N_3O_3$: C, 72.71H, 6.34; N, 9.78. Found: C, 72.92; H, 6.50; N, 9.99.

Example 31

Preparation of 1-[(3-Hydroxyphenyl)methyl]-5-methoxy-2-methyl-1H-indole-3-acetic acid hydrazide.

A  1-[(3-hydroxyphenyl)methyl]-5-methoxy-2-methyl-1H-indole-3-acetic acid ethyl ester. A solution of 357 mg (0.8 mmol) of 1-[(3-benzloxyphenyl)methyl]-5-methoxy-2-methyl-1H-indole-3-acetic acid ethyl ester (Example 31, Part A) in 30 mL of 1:1 tetrahydrofuran/EtOH was hydrogenated at 60 psi (4218 g/cm²) of hydrogen for 16 hours using 90 mg of Pd/BaSO₄. The catalyst was filtered and the filtrate concentrated at reduced pressure. The residue was taken up in EtOAc and washed with water and saturated NaCl solution. After drying over MgSO₄, the product was chromatographed over silica eluting with 1:1 EtOAc.hexane, then EtOAc to give after crystallizing from MeOH, 100 mg (35% yield) of 1-[(3-hydroxyphenyl)methyl]-5-methoxy-2-methyl-1H-indole-3-acetic acid ethyl ester, mp 114°–116° C.

Analyses: Calc'd for $C_{21}H_{23}NO_4$: C, 71.37; H, 6.56; N, 3.96. Found: C, 71.63; H, 6.49 ; N, 4.14.

B. 1-[(3-Hydroxyphenyl)methyl]-5-methoxy-2-methyl-1H-indole-3-acetic acid hydrazide. Using the method described in Example 1, Part G, 76 mg (0.22 mmol) of 1-[(3-hydroxyphenyl)-methyl]-5-methoxy-2-methyl-1H-indole-3-acetic acid ethyl ester was reacted with 0.22 mL of hydrazine to give after crystallizing from MeOH 35 mg (47% yield) of 1-[(3-hydroxyphenyl)methyl]-5-methoxy-2-methyl-1H-indole-3-acetic acid hydrazide, mp 201°–203° C.

Analyses: Calc'd for $C_{19}H_{21}N_3O_3$: C, 67.24H, 6.24; N, 12.38. Found: C, 67.46; H, 6.36; N, 12.33.

Example 32

Preparation of 1-[(4-Benzyloxyphenyl)methyl]-5-methoxy-2-methyl-1H-indole-3-acetic acid hydrazide.

A. 1-[(4-Benzyloxyphenyl)methyl]-5-methoxy-2-methyl-1H-indole-3-acetic acid ethyl ester. Using the procedure described in Example 1, Part F, 494 mg (2 mmol) of 5-methoxy-2-methyl-1H-indole-3-acetic acid ethyl ester was reacted with 80 mg (2 mmol) of 60% NaH/mineral oil and 465 mg (2 mmol) of para-benzyloxybenzylchloride and after chromatography on silica (eluting with 20% EtOAc/hexane) and crystallizing from MeOH there was obtained 347 mg(39%) of 1-[(4-benzyloxyphenyl)methyl]-5-methoxy-2-methyl-1H-indole-3-acetic acid ethyl ester, mp, 118°–119° C.

Analyses: Calc'd for $C_{28}H_{29}NO_4$: C, 75.82; H, 6.59; N, 3.16. Found: C, 75.94; H, 6.60; N, 2.96.

B. 1-[(4-Benzyloxyphenyl)methyl]-5-methoxy-2-methyl-1H-indole-3-acetic acid hydrazide. Using the method described in Example 1, Part G, 315 mg (0.7 mmol) of 1-[(4-benzyloxy-phenyl)methyl]-5-methoxy-2-methyl-1H-indole-3-acetic acid ethyl ester was reacted with 1.0 mL of hydrazine to give after crystallizing from MeOH 246 mg (82% yield) of 1-[(4-benzyloxyphenyl)methyl]-5-methoxy-2-methyl-1H-indole-3-acetic acid hydrazide, mp, 179°–180° C.

Analyses: Calc'd for $C_{26}H_{27}N_3O_3$: C, 72.71H, 6.34; N, 9.78. Found: C, 72.76; H, 6.43; N, 10.01.

Example 33

Preparation of 1-[(4-Hydroxyphenyl)methyl]-5-methoxy-2-methyl-1H-indole-3-acetic acid hydrazide.

A. 1-[(4-Hydroxyphenyl)methyl]-5-methoxy-2-methyl-1H-indole-3-acetic acid ethyl ester. Using the procedure described in Example 32, Part A, 357 mg (0.8 mmol) of 1-[(4-benzyloxyphenyl)methyl]-5-methoxy-2-methyl-1H-indole-3-acetic acid ethyl ester (Example 33, Part A) was hydrogenated to give, after chromatography on silica (eluted with 25% EtOAc/hexane) and crystallization from MeOH, 202 mg (77% yield) of 1-[(4-hydroxyphenyl)methyl]-5- methoxy-2-methyl-1H-indole-3-acetic acid ethyl ester, mp, 113°–115° C.

Analyses: Calc'd for $C_{21}H_{23}NO_4$: C, 71.37; H, 6.56; N, 3.96. Found: C, 71.08; H, 6.57; N, 4.18.

B. 1-[(4-Hydroxyphenyl)methyl]-5-methoxy-2-methyl-1H-indole-3-acetic acid hydrazide. Using the method described in Example 1, Part G, 182 mg (0.5 mmol) of 1-[(4-hydroxyphenyl)-methyl]-5-methoxy-2-methyl-1H-indole-3-acetic acid ethyl ester was reacted with 1.0 mL of hydrazine to give after crystallizing from MeOH 110 mg (65% yield) of 1-[(4-hydroxyphenyl)methyl]-5-methoxy-2-methyl-1H-indole-3-acetic acid hydrazide, mp, 211°–214° C.

Analyses : Calc'd for $C_{19}H_{21}N_3O_3$: C, 67.24H, 6.24; N, 12.38. Found: C, 67.74; H, 6.32; N, 11.83.

Example 34

Preparation of 5-Methoxy-2-methyl-1-[(3-nitrophenyl)methyl]-1H-indole-3-acetic acid hydrazide.

A. 5-Methoxy-2-methyl-1-[(3-nitrophenyl)methyl]-1H-indole-3-acetic acid ethyl ester. Using the procedure described in Example 1, Part F, 494 mg (2 mmol) of 5-methoxy-2-methyl-1H-indole-3-acetic acid ethyl ester was reacted with 80 mg (2 mmol) of 60% NaH/mineral oil and 432 mg (2 mmol) of meta-nitrobenzyl bromide and after chromatography on silica (eluting with 25% EtOAc/hexane) and crystallization from MeOH, there was obtained 141 mg(18%) of 5-methoxy-2-methyl-1-[(3-nitrophenyl)methyl]-1H-indole-3-acetic acid ethyl ester, mp 105°–106° C.

Analyses: Calc'd for $C_{21}H_{22}N_2O_5$: C, 65.96; H, 5.80; N, 7.33. Found: C, 6 5.84; H, 5.86; N, 7.36.

B. 5-Methoxy-2-methyl-1-[(3-nitrophenyl)methyl]-1H-indole-3-acetic acid hydrazide. Using the method described in Example 1, Part G, 115 mg (0.3 mmol) of 5-methoxy-2-methyl-1-[(3-nitrophenyl)methyl]-1H-indole-3-acetic acid ethyl ester was reacted with 0.3 mL of hydrazine to give after crystallizing from MeOH 42 mg (38% yield) of 5-methoxy-2-methyl-1-[(3-nitrophenyl)methyl]-1H-indole-3-acetic acid hydrazide, mp, 177°–179° C.

Analyses: Calc'd for $C_{19}H_{20}N_4O_4$: C, 61.95H, 5.47; N, 15.21. Found: C, 62.53; H, 5.56; N, 14.96.

Example 35

Preparation of 1-[(3-Aminophenyl)methyl]-5-methoxy-2-methyl-1H-indole-3-acetic acid hydrazide.

A. 1-[(3-Aminophenyl)methyl]-5-methoxy-2-methyl-1H-indole-3-acetic acid ethyl ester. A solution of 500 mg (1.3 mmol) of 5-methoxy-2-methyl-1-[(3-nitrophenyl)methyl]-1H-indole-3-acetic acid ethyl ester in 50 mL of EtOH was hydrogenated for 16 hours at room temperature using 0.1 g of 5% Pd/C and 60 psi (4218 g/cm$^2$) of hydrogen. The catalyst was filtered and the filtrate concentrated at reduced pressure. The residue was chromatographed on silica, eluting with 25% EtOAc/hexane to give 234 mg (51% yield) of 1-[(3-aminophenyl)methyl]-5-methoxy-2-methyl-1H-indole-3-acetic acid ethyl ester as an oil.

Analyses: Calc'd for $C_{21}H_{24}N_2O_3$: C, 71.57; H, 6.86; N, 7.95. Found: C, 71.18; H, 6.75; N, 7.52.

B. 1-[(3-Aminophenyl)methyl]-5-methoxy-2-methyl-1H-indole-3-acetic acid hydrazide. Using the method described in Example 1, Part G, 192 mg (0.54 mmol) of 1-[(3-aminophenyl)-methyl]5-methoxy-2-methyl-1H-indole-3-acetic acid ethyl ester was reacted with 1.0 mL of hydrazine to give after crystallizing from MeOH 73 mg (40% yield) of 1-[(3-aminophenyl)methyl]-5-methoxy-2-methyl-1H-indole-3-acetic acid hydrazide, mp, 154°–156° C.

Analyses: Calc'd for $C_{19}H_{22}N_4O_2$: C, 67.44; H, 6.55; N, 16.56. Found: C, 67.47; H, 6.49; N, 16.46.

Example 36

Preparation of 5-Methoxy-2-methyl-1-(1-phenylethyl)-1H-indole-3-acetic acid hydrazide.

A. 5-Methoxy-2-methyl-1-(1-phenylethyl)-1H-indole-3-acetic acid ethyl ester. Using the procedure described in Example 1, Part F, 494 mg (2 mmol) of 5-methoxy-2-methyl-1H-indole- 3-acetic acid ethyl ester was reacted with 80 mg (2 mmol) of 60% NaH/mineral oil and 0.27 mL (2 mmol) of (1-bromoethyl)benzene and after chromatography on silica (eluting with 25% EtOAc/hexane) there was obtained 160 mg (22%) of 5-methoxy-2-methyl-1-(1-phenylethyl)1H-indole-3-acetic acid acid ethyl ester as an oil.

Analyses: Calc'd for $C_{22}H_{25}NO_3$: C, 75.19; H, 7.17; N, 3.99. Found: C, 75.45; H, 7.45; N, 4.40.

B. 5-Methoxy-2-methyl-1-(1-phenylethyl)-1H-indole-3-acetic acid hydrazide. Using the method described in Example 1, Part G, 143 mg (0.4 mmol) of 5-methoxy-2-methyl-1-(1-phenylethyl)-1H-indole-3-acetic acid ethyl ester was reacted with 0.5 mL of hydrazine to give after chromatography on silica (eluting with EtOAc) 80 mg (59% yield) of 5-methoxy-2-methyl-1-(1-phenylethyl)-1H-indole-3-acetic acid hydrazide as a white foam.

Analyses: Calc'd for $C_{20}H_{23}N_3O_2$: C, 71.19; H, 6.87; N, 12.45. Found: C, 71.41; H, 7.07; N, 12.53.

Example 37

Preparation of 5-Methoxy-2-methyl-1-[(2-pyridyl)methyl]-1H-indole-3-acetic acid hydrazide.

A. 5-Methoxy-2-methyl-1-[(2-pyridyl)methyl]-1H-indole-3-acetic acid ethyl ester. Using the procedure described in Example 1, Part F, 494 mg (2 mmol) of 5-methoxy-2-methyl-1H-indole-3-acetic acid ethyl ester was reacted with 160 mg (4 mmol) of 60% NaH/mineral oil and 328 mg (2 mmol) of 2-picolyl chloride hydrochloride and after chromatography on silica (eluting with 50% EtOAc/hexane) there was obtained 510 mg (75%) of 5-methoxy-2-methyl-1-[(2-pyridyl)methyl]-1H-indole-3-acetic acid ethyl ester as an oil.

Analyses: Calc'd for $C_{20}H_{22}N_2O_3$: C, 70.99; H, 6.55; N, 8.28. Found: C, 71.28; H, 6.84; N, 8.44.

B. 5-Methoxy-2-methyl-1-[(2-pyridyl)methyl]-1H-indole-3-acetic acid hydrazide. Using the method described in Example 1, Part G, 480 mg (1.4 mmol) of 5-methoxy-2-methyl-1-[(2-pyridyl)methyl]-1H-indole-3-acetic acid ethyl ester was reacted with 1.4 mL of hydrazine to give on crystallization from MeOH 304 mg (67% yield) of 5-methoxy-2-methyl-1-[(2-pyridyl)methyl]-1H-indole-3-acetic acid hydrazide, mp, 147°–148° C.

Analyses: Calc'd for $C_{18}H_{20}N_4O_2$: C, 66.65H, 6.22; N, 17.27. Found: C, 66.40; H, 6.21; N, 17.34.

Example 38

Preparation of 5-Methoxy-2-methyl-1-[(3-pyridyl)methyl]-1H-indole-3-acetic acid hydrazide.

A. 5-Methoxy-2-methyl-1-[(3-pyridyl)methyl]-1H-indole-3-acetic acid ethyl ester. To a solution of 247 mg (1 mmol) of 5-methoxy-2-methyl-1H-indole-3-acetic acid ethyl ester in 5 mL of DMSO was added 154 mg of 85% KOH. The mixture was cooled with an ice-water bath and 164 mg (1 mmol) of 3-picolyl chloride hydrochloride was added. The cooling bath was removed and the mixture stirred for 4 hours. After diluting with water the product was extracted with EtOAc and the EtOAc solution washed with saturated NaCl solution. After drying over $MgSO_4$, the product was chromatographed over silica eluting with 50% EtOAc/hexane and then crystallized from MeOH to give 75 mg (22% yield) of 5-methoxy-2-methyl-1-[(3-pyridyl)methyl ]-1H-indole-3-acetic acid ethyl ester, mp, 109°–111° C.

Analyses: Calc'd for $C_{20}H_{22}N_2O_3$: C, 70.99; H, 6.55; N, 8.28. Found: C, 71.05; H, 6.66 ; N, 8.20.

B. 5-Methoxy-2-methyl-1-[(3-pyridyl)methyl]-1H-indole-3-acetic acid hydrazide. Using the method described in Example 1, Part G, 340 mg (1.0 mmol) of 5-methoxy-2-methyl-1-[(3-pyridyl)methyl]-1H-indole-3-acetic acid ethyl ester was reacted with 1.0 mL of hydrazine to give on crystallization from MeOH 54 mg (17% yield) of 5-methoxy-2-methyl-1-[(3-pyridyl)methyl]-1H-indole-3-acetic acid hydrazide, mp 153°–154.5° C.

Analyses: Calc'd for $C_{218}H_{20}N_4O_2$: C, 66.65H, 6.22; N, 17.27. Found: C, 66.84; H, 6.36; N, 17.17.

Example 39

Preparation of 5-Methoxy-2-methyl-1-[(4-pyridyl)methyl]-1H-indole-3-acetic acid hydrazide.

A. 5-Methoxy-2-methyl-1-[(4-pyridyl)methyl]-1H-indole-3-acetic acid ethyl ester. Using the procedure described in Example 1, Part F, 494 mg (2 mmol) of 5-methoxy-2-methyl-1H-indole-3-acetic acid ethyl ester was reacted with 160 mg (4 mmol) of 60% NaH/mineral oil and 328 mg (2 mmol) of 4-picolyl chloride hydrochloride and after chromatography on silica (eluting with 50% EtOAc/hexane) there was obtained 480 mg (71%) of 5-methoxy-2-methyl-1-[(4-pyridyl)methyl]-1H-indole-3-acetic acid ethyl ester as an oil which solidified on standing.

B. 5-Methoxy-2-methyl-1-[(4-pyridyl)methyl]-1H-indole-3-acetic acid hydrazide. Using the method described in Example 1, Part G, 410 mg (1.2 mmol) of 5-methoxy-2-methyl-1-[(4-pyridyl)methyl]-1H-indole-3-acetic acid ethyl ester was reacted with 1.2 mL of hydrazine to give on crystallization from MeOH 148 mg (38% yield) of 5-methoxy-2-methyl-1-[(4-pyridyl)methyl]-1H-indole-3-acetic acid hydrazide, mp, 192°–193.5° C.

Analyses: Calc'd for $C_{18}H_{20}N_4O_2$: C, 66.65H, 6.22; N, 17.27. Found: C, 66.54; H, 6.27; N, 17.10.

Example 40

Preparation of 5-Methoxy-2-methyl-1-[(2-quinolyl)methyl]-1H-indole-3-acetic acid hydrazide.

A. 5-Methoxy-2-methyl-1-[(2-quinolyl)methyl]-1H-indole-3-acetic acid ethyl ester. Using the procedure described in Example 1, Part F, 525 mg (2.1 mmol) of 5-methoxy-2-methyl-1H-indole-3-acetic acid ethyl ester was reacted with 168 mg (4.2 mmol) of 60% NaH/mineral oil and 450 mg (2.1 mmol) of 2-chloromethyl-quinoline hydrochloride and after chromatography on silica (eluting with 25% EtOAc/hexane) there was obtained 466 mg (57%) of 5-methoxy-2-methyl-1-[(2-quinolyl)methyl]-1H-indole-3-acetic acid ethyl ester as an oil.

B. 5-Methoxy-2-methyl-1-[(2-quinolyl)methyl]-1H-indole-3-acetic acid hydrazide. Using the method described in Example 1, Part G, 446 mg (1.15 mmol) of 5-methoxy-2-methyl-1-[(2-quinolyl)methyl]-1H-indole-3-acetic acid ethyl ester was reacted with 1.0 mL of hydrazine to give on crystallization from MeOH 238 mg (55% yield) of 5-methoxy-2-methyl-1-[(2-quinolyl)methyl]-1H-indole-3-acetic acid hydrazide, mp, 173°–175° C.

Analyses: Calc'd for $C_{22}H_{22}N_4O_2$: C, 70.57H, 5.92; N, 4.96. Found: C, 70.37; H, 6.02; N, 14.93.

Example 41

Preparation of 5-Methoxy-2-methyl-1-(3-phenylpropyl)-1H-indole-3-acetic acid hydrazide.

A. 5-Methoxy-2-methyl-1-(3-phenylpropyl)-1H-indole-3-acetic acid ethyl ester. Using the procedure described in Example 1 Part F, 494 mg (2 mmol) of 5-methoxy-2-methyl-1H-indole-3-acetic acid ethyl ester was reacted with 80 mg (2 mmol) of 60% NaH/mineral oil and 0.3 mL (2 mmol) of 1-bromo-3-phenylpropane and after chromatography on silica(eluting with 25% EtOAc/hexane) there was obtained 424 mg (58%) of 5-methoxy-2-methyl-1-(3-phenylpropyl)-1H-indole-3-acetic acid ethyl ester as an oil.

Analyses: Calc'd for $C_{23}H_{27}NO_3$: C, 75.59; H, 7.45; N, 3.83. Found: C, 75.71; H, 7.70; N, 3.90.

B. 5-Methoxy-2-methyl-1-(3-phenylpropyl)-1H-indole-3-acetic acid hydrazide. Using the method described in Example 1, Part G, 308 mg (0.84 mmol) of 5-methoxy-2-methyl-1-(3-phenylpropyl)-1H-indole-3-acetic acid ethyl ester was reacted with 0.9 mL of hydrazine to give after crystallizing from MeOH 93 mg (31% yield) of 5-methoxy-2-methyl-1-(3-phenylpropyl)-1H-indole-3-acetic acid hydrazide, mp, 133°–135° C.

Analyses: Calc'd for $C_{21}H_{25}N_3O_2$: C, 71.77; H, 7.17; N, 11.96. Found: C, 72.02; H, 7.38; N, 11.98.

Example 42

Preparation of 5-Methoxy-2-methyl-1-(4-phenylbutyl)-1H-indole-3-acetic acid hydrazide.

A. 5-Methoxy-2-methyl-1-(4-phenylbutyl)-1H-indole-3-acetic acid ethyl ester. Using the procedure described in Example 1, Part F, 494 mg (2 mmol) of 5-methoxy-2-methyl-1H-indole-3-acetic acid ethyl ester was reacted with 80 mg (2 mmol) of 60% NaH/mineral oil and 337 mg (2 mmol of 4-chlorobutylbenzene and after chromatography on silica (eluting with 20% EtOAc/hexane) there was obtained 234 mg (15%) of 5-methoxy-2-methyl-1-(4-phenylbutyl)-1H-indole-3-acetic acid ethyl ester as an oil.

Analyses: Calc'd for $C_{24}H_{29}NO_3$: C, 75.96; H, 7.70; N, 3.69. Found: C, 76.18; H, 7.73 ; N, 3.79.

B. 5-Methoxy-2-methyl-1-(4-phenylbutyl)-1H-indole-3-acetic acid hydrazide. Using the method described in Example 1, Part G, 215 mg (0.57 mmol) of 5-methoxy-2-methyl-1-(4-phenylbutyl)-1H-indole-3-acetic acid ethyl ester was reacted with 0.6 mL of hydrazine to give after crystallizing from MeOH 62 mg 30% yield) of 5-methoxy-2-methyl-1-(4-phenylbutyl)-1H-indole-3-acetic acid hydrazide, mp, 133°–135° C.

Analyses: Calc'd for $C_{22}H_{27}N_3O_2$: C, 72.30; H, 7.45; N, 11.50. Found: C, 72.32; H, 7.45; N, 11.35.

Example 43

Preparation of 2-Chloro-5-methoxy-1-(phenylmethyl)-1H-indole-3-acetic acid hydrazide.

A. 5-Methoxy-1-(phenylmethyl)-1H-indole-3-acetic acid phenylmethyl ester. A solution of 2.0 g (10 mmol) of 5-methoxy-1H-indole-3-acetic acid in 100 mL of DMF was treated in portions with 1.0 g (25 mmol) of 60% NaH/mineral oil and after 10 minutes, 3 mL of benzyl bromide added. After 22 hours, the mixture was diluted with water, extracted with EtOAc, the EtOAc solution washed with water, saturated NaCl solution and dried over $Na_2SO_4$. After concentrating at reduced pressure, the residue was chromatographed over silica eluting with $CH_2Cl_2$ to give 3.7 g (96% yield) of 5-methoxy-1-(phenylmethyl)-1H-indole-3-acetic acid phenylmethyl ester as an oil (structure confirmed by nmr).

B. 2-Chloro-5-methoxy-1-(phenylmethyl)-1H-indole-3-acetic acid phenylmethyl ester. While cooling at −5° C., 0.6 mL (4.9 mmol) of borontrifluoride etherate was added to 770 mg (2 mmol) of 5-methoxy-1-(phenylmethyl)-1H-indole-3-acetic acid phenylmethyl ester in 100 mL of $CH_2Cl_2$, followed by 0.24 mL (3 mmol) of $SO_2Cl_2$. After 10 minutes, an aqueous $NaHCO_3$ solution was added, the $CH_2Cl_2$ layer separated, dried ($Na_2SO_4$), and concentrated at reduced pressure. The residue was chromatographed on silica eluting with a gradient (15% ether/hexane→100% ether) to give 100 mg (12% yield) of 2-chloro-5-methoxy-1-(phenylmethyl)-1H-indole-3-acetic acid phenylmethyl ester(structure confirmed by nmr).

C. 2-Chloro-5-methoxy-1-(phenylmethyl)-1H-indole-3-acetic acid hydrazide. A solution of 100 mg (0.238 mmol) of 2-chloro-5-methoxy-1H-indole-3-acetic acid phenylmethyl ester and 5 mL of hydrazine hydrate in 40 mL of EtOH was heated to maintain reflux for 1.5 hours. The reaction mixture was cooled, extracted with EtOAc, the EtOAc solution washed with saturated NaCl solution and dried over $Na_2SO_4$. After concentrating at reduced pressure, the residue was triturated with ether and dried to give 90 mg (100% yield) of 2-chloro-5-methoxy-1-(phenylmethyl)-1H-indole-3-acetic acid hydrazide, mp, 186°–187° C.

Analyses: Calc'd for $C_{18}H_{18}ClN_3O_2$: C, 62.88; H, 5.28; Cl, 10.31; N, 12.22. Found: C, 62.31; H, 5.62; Cl, 10.63; N, 11.30.

Example 44

Preparation of 2-Bromo-5-methoxy-1-(phenylmethyl)-1H-indole-3-acetic acid hydrazide.

A. 2-Bromo-5-methoxy-1-(phenylmethyl)-1H-indole-3-acetic acid phenylmethyl ester. With stirring, 450 mg (2.5 mmol) of N-bromosuccinimide was added to 910 mg (2.4 mmol) of 5-methoxy-1-(phenylmethyl)-1H-indole-3-acetic acid phenylmethyl ester (Example 44, Part A) in 75 mL of $CCl_4$. After 15 minutes, the reaction mixture was washed with an aqueous $Na_2S_2O_4$ solution, water, then saturated NaCl solution, and dried over $Na_2SO_4$. After concentrating at reduced pressure, the residue was chromatographed on silica eluting with a $CH_2Cl_2$ and crystallizing from ether/hexane to give 420 mg (69% yield) of 2-bromo-5-methoxy-1-(phenylmethyl)-1H-indole-3-acetic acid phenylmethyl ester, mp, 89°–90° C.

Analyses: Calc'd for $C_{25}H_{22}BrNO_3$: C, 64.66; H, 4.78; N, 3.02. Found: C, 64.43; H, 4.75; N, 2.96.

B. 2-Bromo-5-methoxy-1-(phenylmethyl)-1H-indole-3-acetic acid hydrazide. A solution of 340 mg (0.732 mmol) of 2-Bromo-5-methoxy-1-(phenylmethyl)-1H-indole-3-acetic acid phenylmethyl ester and 5 mL of hydrazine hydrate in 50 mL of EtOH was heated to maintain reflux for 2.75 hours. The reaction mixture was cooled, extracted with EtOAc, the EtOAc solution washed with saturated NaCl solution and dried over $Na_2SO_4$. After concentrating at reduced pressure, the residue was chromatographed on silica eluting with ether, then EtOAc to give 200 mg (71% yield) of 2-bromo-5-methoxy-1-(phenylmethyl)-1H-indole-3-acetic acid hydrazide, mp, 178°–180° C.

Analyses: Calc'd for $C_{18}H_{18}BrN_3O_2$: C, 55.68; H, 4.67; Br, 20.58;N, 10.82. Found: C, 54.02; H, 4.52; Br, 23.17; N, 10.69.

Example 45

Preparation of 5-Methoxy-2-methylthio-1-(phenylmethyl)-1H-indole-3-acetic acid hydrazide.

A. 5-Methoxy-2-methylthio-1-(phenylmethyl)-1H-indole-3-acetic acid phenylmethyl ester. A solution of 1.0 mL (11 mmol) of dimethyl disulfide in 25 mL of $CH_2Cl_2$ was cooled to −25° C., 0.8 mL (10 mmol) of $SO_2Cl_2$ added, the cooling bath removed, and the mixture stirred and let warm to room temperature. Three mL of this solution was added to 770 mg (2 mmol) of 5-methoxy-1-(phenylmethyl)-1H-indole-3-acetic acid phenylmethyl ester (Example 44, Part A) in 100 mL of $CH_2Cl_2$. After 0.5 hour, the reaction mixture was washed with an aqueous $Na_2CO_3$ solution, saturated NaCl solution, and dried over $Na_2SO_4$. After concentrating at reduced pressure, the residue was chromatographed on silica (eluted with a gradient, 20% ether/hexane→30% ether/hexane) and crystallized from ether/hexane to give 600 mg (70% yield) of 5-methoxy-2-methylthio-1-(phenylmethyl)-1H-indole-3-acetic acid phenylmethyl ester, mp, 89°–90° C.

Analyses: Calc'd for $C_{26}H_{25}NO_3S$: C, 72.36; H, 5.84; N, 3.25; S, 7.75. Found: C, 72.43; H, 5.87; N, 3.30; S,7.60.

B. 5-Methoxy-2-methylthio-1-(phenylmethyl)-1H-indole-3-acetic acid hydrazide. Using the procedure described in Example 45, Part B, 240 mg (0.555) of 5-methoxy-2-methylthio-1-(phenylmethyl)-1H-indole-3-acetic acid phenylmethyl ester and 5 mL of hydrazine hydrate in 40 mL of EtOH were converted to 205 mg (100% yield) of 5-methoxy-2-methylthio-1-(phenylmethyl)-1H-indole-3-acetic acid hydrazide, mp, 181°–182° C.

Analyses: Calc'd for $C_{19}H_{21}N_3O_2S$: C, 64.20; H, 5.95; N, 11.82; S, 9.02. Found: C, 64.05; H, 5.99; N, 11.53; S, 8.75.

Example 46

Preparation of 5-Methoxy-2-methylsulfinyl-1-(phenylmethyl)-1H-indole-3-acetic acid hydrazide.

A. 5-Methoxy-2-methylsulfinyl-1-(phenylmethyl)-1H-indole-3-acetic acid phenylmethyl ester. To a solution of 460 mg (1 mmol) of 5-methoxy-2-methylthio-1-(phenylmethyl)-1H-indole-3-acetic acid phenylmethyl ester in 50 mL of $CH_2Cl_2$ was added 200 mg (1.0 mmol) of m-chloroperbenzoic acid (80–85% pure) and the mixture stirred 0.75 hour. The reaction mixture was washed with $Na_2CO_3$ solution, dried($Na_2SO_4$), and concentrated at reduced pressure to give a residue that was chromatographed on silica (eluted with $CH_2Cl_2$, then ether) and crystallized from EtOH to give 424 mg (95% yield) of 5-methoxy-2-methylsulfinyl-1-(phenylmethyl)-1H-indole-3-acetic acid phenylmethyl ester, as a solid.

Analyses: Calc'd for $C_{26}H_{25}NO_4S$: C, 69.78; H, 5.63; N, 3.13; S, 7.16. Found: C, 69.99; H, 5.76; N, 3.24; S, 7.11.

B. 5-Methoxy-2-methylsulfinyl-1-(phenylmethyl)-1H-indole-3-acetic acid hydrazide. Using the procedure described in Example 45, Part B, 380 mg (0.85 mmol) of 5-methoxy-2-methylsulfinyl-1-(phenylmethyl)-1H-indole-3-acetic acid phenylmethyl ester and 3 mL of hydrazine hydrate in 30 mL of EtOH were reacted to give material that was crystallized from EtOAc to give 270 mg (85% yield) of 5-methoxy-2-methylsulfinyl-1-(phenylmethyl)-1H-indole-3-acetic acid hydrazide, mp, 172°–174° C.

Analyses: Calc'd for $C_{19}H_{21}N_3O_3S$: C, 61.44; H, 5.70; N, 11.31; S, 8.42. Found: C, 61.34; H,5.67; N, 11.20; S, 8.63.

Example 47

Preparation of 5-Fluoro-2-methyl-1-(phenylmethyl)-1H-indole-3-acetic acid hydrazide.

A. 5-Fluoro-2-methyl-1H-indole-3-acetic acid ethyl ester. As described in Example 14, Part A, 27.95 g (0.16 mol) of 4-fluorophenylhydrazine hydrochloride and 19.72 g (0.17 mol) of levulinic acid were reacted and after chromatography on silica (5% EtOAc/toluene) gave 5-fluoro-2-methyl-1H-indole-3-acetic acid ethyl ester as an oil.

Analyses: Calc'd for $C_{13}H_{14}FNO_2$: C, 66.37; H, 6.00; N, 5.95. Found: C, 66.12; H, 6.08; N, 5.87.

B. 5-Fluoro-2-methyl-1-(phenylmethyl)-1H-indole-3-acetic acid ether ester. Using the procedure described in Example 1, Part F, 470 mg (2 mmol) of 5-fluoro-2-methyl-1H-indole-3-acetic acid ethyl ester was reacted with 80 mg (2 mmol) of 60% NaH/mineral oil and 0.24 mL (2 mmol) benzyl bromide and after chromatography on silica (eluting with 25% EtOAc/hexane) and crystallizing from MeOH there was obtained 499 mg (77%) of 5-fluoro-2-methyl-1-(phenylmethyl)-1H-indole-3-acetic acid ether ester, mp, 79°–81° C.

Analyses: Calc'd for $C_{20}H_{20}FNO_2$: C, 73.83; H, 6.20; N, 4.30. Found: C, 74.12; H, 6.30; N, 4.31.

C. 5-Fluoro-2-methyl-1-(phenylmethyl)-1H-indole-3-acetic acid hydrazide. Using the method described in Example 1, Part G, 450 mg (1.4 mmol) of 5-fluoro-2-methyl-1-(phenylmethyl)-1H-indole-3-acetic acid ether ester was reacted with 2.0 mL of hydrazine to give after crystallizing from MeOH 170 mg (39% yield) of 5-fluoro-2-methyl-1-(phenylmethyl)-1H-indole-3-acetic acid hydrazide, mp, 167°–169° C.

Analyses: Calc'd for $C_{18}H_{18}FN_3O$: C, 69.44; H, 5.83; N, 13.50. Found: C, 69.70H, 5.87; N, 13.67.

Example 48

Preparation of 5-Chloro-2-methyl-1-(phenylmethyl)-1H-indole-3-acetic acid hydrazide.

A. 5-Chloro-2-methyl-1H-indole-3-acetic acid ethyl ester. As described in Example 14, Part A, 16.01 g (0.089 mol) of 4-chlorophenylhydrazine hydrochloride and 10.65 g (0.092 mol) of levulinic acid were treated with dry HCl in EtOH to give after chromatography on silica (eluted with 15% EtOAc/hexane) 11.5 g (51% yield) of 5-chloro-2-methyl-1H-indole-3-acetic acid ethyl ester as an oil.

Analyses: Calc'd for $C_{13}H_{14}ClNO_2$: C, 62.03; H, 5.61; N, 5.57. Found: C, 61.97; H, 5.58; N, 5.85.

B. 5-Chloro-2-methyl-1-(phenylmethyl)-1H-indole-3-acetic acid ether ester. Using the procedure described in Example 1, Part F, 503 mg (2 mmol) of 5-chloro-2-methyl-1H-indole-3-acetic acid ethyl ester was reacted with 80 mg (2 mmol) of 60% NaH/mineral oil and 0.24 mL (2 mmol) benzyl bromide and after chromatography on silica (eluting with 25% EtOAc/hexane) there was obtained 357 mg (52%) of 5-chloro-2-methyl-1-(2-phenylmethyl)-1H-indole-3-acetic acid ether ester as an oil.

Analyses: Calc'd for $C_{20}H_{20}ClNO_2$: C, 70.27; H, 5.90; N, 4.10. Found: C, 70.48; H, 5.80; N, 3.99.

C. 5-Chloro-2-methyl-1-(phenylmethyl)-1H-indole-3-acetic acid hydrazide. Using the method described in Example 1, Part G, 324 mg (0.95 mmol) of 5-chloro-2-methyl-1-(phenylmethyl)-1H-indole-3-acetic acid ether ester was reacted with 2.0 mL of hydrazine to give after crystallizing from MeOH 76 mg (24% yield) of 5-chloro-2-methyl-1-(phenylmethyl)-1H-indole-3-acetic acid hydrazide, mp, 167°–169° C.

Analyses: Calc'd for $C_{18}H_{18}ClN_3O$: C, 66.95; H, 5.53; N, 12.82. Found: C, 66.25H, 5.59; N, 12.79.

Example 49

Preparation of 5-Chloro-[(3-chlorophenyl)methyl]-2-methyl-1H-indole-3-acetic acid hydrazide.

A. 5-Chloro-[(3-chlorophenyl)methyl]-2-methyl-1H-indole-3-acetic acid ethyl ester. Using the procedure described in Example 1, Part F, 503 mg (2 mmol) of 5-chloro-2-methyl-1H-indole-3-acetic acid ethyl ester (Example 48, Part A) was reacted with 80 mg (2 mmol) of 60% NaH/mineral oil and 0.25 mL (2 mmol) of m-chlorobenzylchloride and after chromatography on silica (eluting with 20% EtOAc/hexane) and crystallization from MeOH there was obtained 325 mg (43%) of 5-chloro-[(3-chlorophenyl)-methyl]-2-methyl-1-1H-indole-3-acetic acid ethyl ester, mp, 97°–106° C.

Analyses: Calc'd for $C_{20}H_{19}Cl_2NO_2$: C, 63.84; H, 5.09; N, 3.72. Found: C, 64.07; H, 5.10; N, 3.63.

B. 5-Chloro-[(3-chlorophenyl)methyl]-2-methyl-1H-indole-3-acetic acid hydrazide. Using the method described in Example 1, Part G, 315 mg (0.83 mmol) of 5-chloro-[(3-chlorophenyl)methyl]-2-methyl-1-1H-indole-3-acetic acid ethyl ester was reacted with 0.9 mL of hydrazine to give after crystallizing from MeOH 119 mg (40% yield) of 5-chloro-[(3-chlorophenyl)-methyl]-2-methyl-1-1H-indole-3-acetic acid hydrazide, mp, 168°–170° C.

Analyses: Calc'd for $C_{18}H_{17}Cl_2N_3O$: C, 59.68; H, 4.73; N, 11.60. Found: C,59.79; H, 4.86; N, 11.83.

Example 50

Preparation of 5-Bromo-2-methyl-1-(phenylmethyl)-1H-indole-3-acetic acid hydrazide.

A. 5-Bromo-2-methyl-1H-indole-3-acetic acid ethyl ester. As described in Example 14, Part A, 32.3 g (0.144 mol) of 4-bromophenylhydrazine hydrochloride and 15.36 mL (0.15 mol) of levulinic acid were treated with dry HCl in 300 mL of EtOH to give after chromatography on silica (eluted with 5% EtOAc/toluene) 35.72 g (83% yield) of 5-bromo-2-methyl-1H-indole-3-acetic acid ethyl ester, that solidified on standing, mp, 65°–68° C.

Analyses: Calc'd for $C_{13}H_{14}BrNO_2$: C, 52.72; H, 4.77; N, 4.73. Found: C, 52.94; H, 4.77; N, 4.95.

B. 5-Bromo-2-methyl-1-(phenylmethyl)-1H-indole-3-acetic acid ethyl ester. Using the procedure described in Example 1, Part F, 592 mg (2 mmol) of 5-bromo-2-methyl-1H-indole-3-acetic acid ethyl ester was reacted with 80 mg (2 mmol) of 60% NaH/mineral oil and 0.24 mL (2 mmol) benzyl bromide and after chromatography on silica (eluting with 33% EtOAc/hexane) and crystallizing from MeOH there was obtained 330 mg (42%) of 5-bromo-2-methyl-1-(phenylmethyl)-1H-indole-3-acetic acid ethyl ester, mp, 83°–84° C.

Analyses: Calc'd for $C_{20}H_{20}BrNO_2$: C, 62.19; H, 5.22; N, 3.63. Found: C, 62.44; H, 5.29; N, 3.59.

C. 5-Bromo-2-methyl-1-(phenylmethyl)-1H-indole-3-acetic acid hydrazide. Using the method described in Example 1, Part G, 312 mg (0.81 mmol) of 5-bromo-2-methyl-1-(phenylmethyl)-1H-indole-3-acetic acid ethyl ester was reacted with 0.81 mL of hydrazine to give after crystallizing from MeOH 130 mg (43% yield) of 5-bromo-2-methyl-1-(phenylmethyl)-1H-indole-3-acetic acid hydrazide, mp 181°–182° C.

Analyses: Calc'd for $C_{18}H_{18}BrN_3O$: C, 58.08; H, 4.87; N, 11.29. Found: C, 58.37; H, 4.87 N, 11.27.

Example. 51

Preparation of 1-([1,1'-biphenyl]-3-ylmethyl)-5-bromo-2-methyl-1H-indole-3-acetic acid hydrazide.

A. 1-([1,1'-biphenyl]-3-ylmethyl)-5-bromo-2-methyl-1H-indole-3-acetic acid ethyl ester. Using the procedure described in Example 1, Part F, 592 mg (2 mmol) of 5-bromo-2-methyl-1H-indole-3-acetic acid ethyl ester (Example 51, Part A) was reacted with 80 mg (2 mmol) of 60% NaH/mineral oil and 405 mg (2 mmol) of 3-chloromethylbiphenyl and after workup of the reaction mixture and chromatography on silica (eluted with 33% EtOAc/hexane) there was obtained 690 mg 75%) of 1-([1,1'-biphenyl]-3-ylmethyl)-5-bromo-2-methyl-1H-indole-3-acetic acid ethyl ester as a yellow oil.

Analyses: Calc'd for $C_{26}H_{24}BrNO_2$: C, 67.54; H, 5.23; N, 3.03. Found: C, 67.73; H, 5.46; N, 2.74.

B. 1-([1,1'-biphenyl]-3-ylmethyl)-5-bromo-2-methyl-1H-indole-3-acetic acid hydrazide. Using the method described in Example 1, Part G, 550 mg (1.2 mmol) of 1-([1,1'-biphenyl]-3-ylmethyl)-5-bromo-2-methyl-1H-indole-3-acetic acid ethyl ester was reacted with 1.2 mL of hydrazine to give after crystallizing from MeOH 290 mg (54% yield) of 1-([1,1'-biphenyl]-3-ylmethyl)-5-bromo-2-methyl-1H-indole-3-acetic acid hydrazide, mp, 162°–164° C.

Analyses: Calc'd for $C_{24}H_{22}BrN_3O$: C, 64.29; H, 4.94; N, 9.37. Found: C, 64.52; H, 5.05; N, 9.16.

Example 52

Preparation of 1-[(3-Benzyloxyphenyl)methyl]-5-bromo-2-methyl-1H-indole-3-acetic acid hydrazide.

A. 1-[(3-Benzyloxyphenyl)methyl]-5-bromo-2-methyl-1-1H-indole-3-acetic acid ethyl ester. Using the procedure described in Example 1, Part F, 592 mg (2 mmol) of 5-bromo-2-methyl-1H-indole-3-acetic acid ethyl ester (Example 51, Part A) was reacted with 80 mg (2 mmol) of 60% NaH/mineral oil and 465 mg (2 mmol) of 3-benzyloxybenzylchloride and after workup of the reaction mixture and chromatograpy on silica(eluted with 33% EtOAc/hexane) there was obtained 592 mg (60%) of 1-[(3-benzyloxyphenyl)methyl]-5-bromo-2-methyl-1H-indole-3-acetic acid ethyl ester as an oil.

B. 1-[(3-Benzyloxyphenyl)methyl]-5-bromo-2-methyl-1H-indole-3-acetic acid hydrazide. Using the method described in Example 1, Part G, 565 mg (1.15 mmol) of 1-[(3-benzyloxyphenyl)methyl]-5-bromo-2-methyl-1H-indole-3-acetic acid ethyl ester was reacted with 1.2 mL of hydrazine to give after crystallization from MeOH 318 mg (60% yield) of 1-[(3-benzyloxyphenyl)methyl]-5-bromo-2-methyl-1H-indole-3-acetic acid hydrazide, mp, 163°–164° C.

Analyses: Calc'd for $C_{25}H_{24}BrN_3O_2$: C, 62.77; H, 5.06; N, 8.78. Found: C, 62.69; H, 5.21; N, 8.75.

Example 53

Preparation of 4-Bromo-2-methyl-1-(phenylmethyl)-1H-indole-3-acetic acid hydrazide.

A. 4-Bromo-2-methyl-1H-indole-3-acetic acid ethyl ester and 6-bromo-2-methyl-1H-indole-3-acetic acid ethyl ester. As described in Example 14, Part A, 25.0 g (0.112 mol) of 3-bromophenylhydrazine hydrochloride and 12.28 mL (0.12 mol) of levulinic acid were treated with dry HCl in 300 mL of EtOH and the reaction worked up to give an oil. Chromatograpy on silica eluting with 15% EtOAc/toluene gave in the early fractions, 11.84 g (36% yield) of 6-bromo-2-methyl-1H-indole-3-acetic acid ethyl ester, which solidified on standing, mp, 95°–98° C.

Analyses: Calc'd for $C_{13}H_{14}BrNO_2$: C, 52.72; H, 4.77; N, 4.73. Found: C, 53.59; H, 4.89; N, 4.31.

From the above chromatography, later fractions gave an oil which was triturated with cyclohexane to give 1.8 g (5.5% yield) of 4-bromo-2-methyl-1H-indole-3-acetic acid ethyl ester, mp, 74°–84° C.

Analyses: Calc'd for $C_{13}H_{14}BrNO_2$: C, 52.72; H, 4.77; N, 4.73. Found: C, 52.97; H, 4.78; N, 4.66.

B. 4-Bromo-2-methyl-1-(phenylmethyl)-1H-indole-3-acetic acid ethyl ester. Using the procedure described in Example 1, Part F, 1.18 g (4 mmol) of 4-bromo-2-methyl-1H-indole-3-acetic acid ethyl ester was reacted with 160 mg (2 mmol) of 60% NaH/mineral oil and 0.48 mL (4 mmol) benzyl bromide and after chromatography on silica (eluting with 25% EtOAc/hexane) and crystallizing from MeOH there was obtained 1.2 g (78%) of 4-bromo-2-methyl-1-(phenylmethyl)-1H-indole-3-acetic acid ethyl ester, mp, 133°–135° C.

Analyses: Calc'd for $C_{20}H_{20}BrNO_2$: C, 62.19; H, 5.22; N, 3.63. Found: C, 62.46; H, 5.31; N, 3.64.

C. 4-Bromo-2-methyl-1-(phenylmethyl)-1H-indole-3-acetic acid hydrazide. Using the method described in Example 1, Part G, 386 mg (1.0 mmol) of 4-bromo-2-methyl-1-(phenylmethyl)-1H-indole-3-acetic acid ethyl ester was reacted with 1.0 mL of hydrazine to give after crystallization from MeOH 214 mg (58% yield) of 4-bromo-2-methyl-1-(phenylmethyl)-1H-indole-3-acetic acid hydrazide, mp, 182°–183° C.

Analyses: Calc'd for $C_{18}H_{18}BrN_3O$: C, 58.08; H, 4.87; N, 11.29. Found: C, 58.11; H, 4.90; N, 11.49.

Example 54

Preparation of 6-Bromo-2-methyl-1-(phenylmethyl)-1H-indole-3-acetic acid hydrazide.

A. 6-Bromo-2-methyl-1-(phenylmethyl)-1H-indole-3-acetic acid ethyl ester. Using the procedure described in Example 1, Part F, 1.18 g (4 mmol) of 6-bromo-2-methyl-1H-indole-3-acetic acid ethyl ester (Example 54, Part A) was reacted with 160 mg (2 mmol) of 60% NaH/mineral oil and 0.48 mL (4 mmol) benzyl bromide and after chromatography on silica (eluting with 25% EtOAc/hexane) and crystallizing from MeOH there was obtained 776 mg (50%) of 6-bromo-2-methyl-1-(2-phenylmethyl)-1H-indole-3-acetic acid ethyl ester, mp, 99°–100° C.

Analyses: Calc'd for $C_{20}H_{20}BrNO_2$: C, 62.19; H, 5.22; N, 3.63. Found: C, 62.18; H, 5.29; N, 3.59.

B. 6-Bromo-2-methyl-1-(phenylmethyl)-1H-indole-3-acetic acid hydrazide. Using the method described in Example 1, Part G, 360 mg (0.93 mmol) of 6-bromo-2-methyl-1-(phenylmethyl)-1H-indole-3-acetic acid ethyl ester was reacted with 1.0 mL of hydrazine to give after crystallizing from MeOH 178 mg (51% yield) of 6-bromo-2-methyl-1-(phenylmethyl)-1H-indole-3-acetic acid hydrazide, mp, 183°–184° C.

Analyses: Calc'd for $C_{18}H_{18}BrN_3O$: C, 58.08; H, 4.87; N, 11.29. Found: C, 58.33; H, 4.96; N, 11.28.

Example 55

Preparation of 2-Methyl-4-phenyl-1-(phenylmethyl)-1H-indole-3-acetic acid hydrazide.

A. 2-Methyl-4-phenyl-1-(phenylmethyl)-1H-indole-3-acetic acid ethyl ester. To 25 mL of EtOH was added 386 mg (1.0 mmol) of 4-bromo-2-methyl-1-(phenylmethyl)-1H-indole-3-acetic acid ethyl ester (Example 54, Part B), 139 mg (0.12 mmol) of $Pd[P(C_6H_5)_3]_4$, and 4.5 mL of a 2M $Na_2CO_3$ solution. To this solution was added 281 mg (2.3 mmol) of phenylboric acid in 5 mL of EtOH and the resulting mixture heated to maintain reflux for 16 h. After cooling, the mixture was diluted with EtOAc and filtered thru celite. The filtrate was washed with water and saturated NaCl solution, dried ($MgSO_4$), and concentrated at reduced pressure. The residue was chromatographed on silica, eluting with 25% EtOAc/hexane and then recrystallized twice from MeOH to give 142 mg (37% yield) of 2-methyl-4-phenyl-1-(phenylmethyl)-1H-indole-3-acetic acid ethyl ester, mp, 115°–117° C.

Analyses: Calc'd for $C_{26}H_{25}NO_2$: C, 81.43; H, 6.57; N, 3.65. Found: C, 81.15; H, 6.70; N, 3.71.

B. 2-Methyl-4-phenyl-1-(phenylmethyl)-1H-indole-3-acetic acid hydrazide. Using the method described in Example 1, Part G, 127 mg (0.33 mmol) of 2-methyl-4-phenyl-1-(phenylmethyl)-1H-indole-3-acetic acid ethyl ester was reacted with 0.35 mL of hydrazine to give after crystallizing from MeOH/hexane 40 mg (32% yield) of 2-methyl-4-phenyl-1-(phenylmethyl)-1H-indole-3-acetic acid hydrazide, mp, 73°–77° C.

Analyses: Calc'd for $C_{24}H_{23}N_3O$: C, 78.02; H, 6.27; N, 11.37. Found: C, 78.10; H, 6.35; N, 11.44.

Example 56

Preparation of 2-Methyl-5-phenyl-1-(phenylmethyl)-1H-indole-3-acetic acid hydrazide.

A. 2-Methyl-5-phenyl-1-(phenylmethyl)-1H-indole-3-acetic acid ethyl ester. Using the method described in Example 56, Part A, 266 mg (0.7 mmol) of 5-bromo-2-methyl-1-(phenylmethyl)-1H-indole-3-acetic acid ethyl ester (Example 51, Part B), 194 mg (0.168 mmol) of $Pd[P(C_6H_5)_3]_4$, 3.2 mL of a 2M $Na_2CO_3$ solution, and 196 mg (1.6 mmol) of phenylboric acid were reacted to give, after silica chromatograpy and crystallization from MeOH, 95 mg (35% yield) of 2-methyl-5-phenyl-1-(phenylmethyl)-1H-indole-3-acetic acid ethyl ester, mp 116°–119° C.

Analyses: Calc'd for $C_{26}H_{25}NO_2$: C, 81.43; H, 6.57; N, 3.65. Found: C, 81.41; H, 6.64; N, 3.85.

B. 2-Methyl-5-phenyl-1-(phenylmethyl)-1H-indole-3-acetic acid hydrazide. Using the method described in Example 1, Part G, 80 mg (0.2 mmol) of 2-methyl-5-phenyl-1-(phenylmethyl)-1H-indole-3-acetic acid ethyl ester was reacted with 0.5 mL of hydrazine to give after crystallizing from MeOH 26 mg (35% yield) of 2-methyl-5-phenyl-1-(phenylmethyl)-1H-indole-3-acetic acid hydrazide, mp 154°–156° C.

Analyses: Calc'd for $C_{24}H_{23}N_3O$: C, 78.02; H, 6.27; N, 11.37. Found: C, 78.26; H, 6.28; N, 11.34.

Example 57

Preparation of 2-Methyl-6-phenyl-1-(phenylmethyl)-1H-indole-3-acetic acid hydrazide.

A. 2-Methyl-6-phenyl-1-(phenylmethyl)-1H-indole-3-acetic acid ethyl ester. Using the method described in Example 56, Part A, 386 mg (1.0 mmol) of 6-bromo-2-methyl-1-(phenylmethyl)-1H-indole-3-acetic acid ethyl ester (Example 55, Part A), 139 mg (0.12 mmol) of $Pd[P(C_6H_5)_3]_4$, 4.5 mL of a 2M $Na_2CO_3$ solution, and 281 mg (2.3 mmol) of phenylboric acid were reacted to give, after silica chromatograpy and crystallization from MeOH, 198 mg (52% yield) of 2-methyl-6-phenyl-1-(phenylmethyl)-1H-indole-3-acetic acid ethyl ester, mp, 90°–93° C.

Analyses: Calc'd for $C_{26}H_{25}NO_2$: C, 81.43; H, 6.57; N, 3.65. Found: C, 81.20; H, 6.73; N, 3.70.

B. 2-Methyl-6-phenyl-1-(phenylmethyl)-1H-indole-3-acetic acid hydrazide. Using the method described in Example 1, Part G, 170 mg (0.2 mmol) of 2-methyl-6-phenyl-1-(phenylmethyl)-1H-indole-3-acetic acid ethyl ester were reacted with 0.45 mL of hydrazine to give after crystallizing from MeOH 66 mg (41% yield) of 2-methyl-6-phenyl-1-(phenylmethyl)-1H-indole-3-acetic acid hydrazide, mp, 146°–147° C.

Analyses: Calc'd for $C_{24}H_{23}N_3O$: C, 78.02; H, 6.27; N, 11.37. Found: C, 78.24; H, 6.26; N, 11.27.

Example 58

Preparation of 1-[(3-Benzyloxyphenyl)methyl]-2-methyl-5-phenyl-1H-indole-3-acetic acid hydrazide.

Using the method described in Example 56, Part A, 95.6 mg (0.02 mmol) of 1-[(3-benzyloxyphenyl)methyl]-5-bromo-2-methyl-1H-indole-3-acetic acid hydrazide (Example 53, Part B), 28 mg (0.024 mmol) of $Pd[P(C_6H_5)_3]_4$, 0.9 mL of 2M $Na_2CO_3$ solution, and 56.12 mg (0.46 mmol) of phenylboric acid were reacted to give material that was chromatographed on silica. The column was eluted first with 25% EtOAc/hexane, EtOAc, and then 2% MeOH/EtOAc to give after crystallization from MeOH 22 mg (23% yield) of 1-[(3-benzyoxyphenyl)methyl]-2-methyl-5-phenyl-1H-indole-3-acetic acid hydrazide, mp, 114°–121° C.

Analyses: Calc'd for $C_{31}H_{29}N_3O_2$: C, 78.29; H, 6.15; N, 8.84. Found: C, 78.37; H, 6.20; N, 9.06.

Example 59

Preparation of 2,5-Dimethyl-1-(phenylmethyl)-1H-indole-3-acetic acid hydrazide.

A. 2,5-Dimethyl-1H-indole-3-acetic acid ethyl ester. As described in Example 14, Part A, 25 g (0.158 mol) of 4-methylphenylhydrazine hydrochloride and 18.3 g (0.158 mol) of levulinic acid were treated with dry HCl in 500 mL of EtOH to give after chromatography on silica(eluted with 5% EtOAc/toluene) 30.3 g (77% yield) of 2,5-dimethyl-1H-indole-3-acetic acid ethyl ester, that solidified on standing, mp, 40°–42° C.

Analyses: Calc'd for $C_{14}H_{17}NO_2$: C, 72.70; H, 7.41; N, 6.06. Found: C, 72.53; H, 7.54; N, 6.00.

B. 2,5-Dimethyl-1-(phenylmethyl)-1H-indole-3-acetic acid ethyl ester. Using the procedure described in Example 1, Part F, 464 mg (2 mmol) of 2,5-dimethyl-1H-indole-3-acetic acid ethyl ester was reacted with 80 mg (2 mmol) of 60% NaH/mineral oil and 0.24 mL (2 mmol) of benzyl bromide and after chromatography on silica (eluting with 33% EtOAc/hexane) there was obtained 330 mg (42%) of 2,5-dimethyl-1-(phenylmethyl)-1H-indole-3-acetic acid ethyl ester, mp, 66°–69° C.

Analyses: Calc'd for $C_{21}H_{23}NO_2$: C, 78.47; H, 7.21; N, 4.36. Found: C, 78.27; H, 7.13; N, 4.36.

C. 2,5-Dimethyl-1-(phenylmethyl)-1H-indole-3-acetic acid hydrazide. Using the method described in Example 1, Part G, 375 mg (1.2 mmol) of 2,5-dimethyl-1-(phenylmethyl)-1H-indole-3-acetic acid ethyl ester was reacted with 2.0 mL of hydrazine to give after crystallizing from MeOH 144 mg (39% yield) of 2,5-dimethyl-1-(phenylmethyl)-1H-indole-3-acetic acid hydrazide, mp, 165°–166° C.

Analyses: Calc'd for $C_{19}H_{21}N_3O$: C, 74.24; H, 6.89; N, 13.67. Found: C, 74.49; H, 6.81; N, 13.77.

Example 60

Preparation of 5-tert-Butyl-2-methyl-1-(phenylmethyl)-1H-indole-3-acetic acid hydrazide.

A. 5-tert-Butyl-2-methyl-1H-indole-3-acetic acid ethyl ester. As described in Example 14, Part A, 10 g (0.05 mol) of 4-tert-butylphenylhydrazine hydrochloride and 5.8 g (0.05 mol) of levulinic acid were treated with dry HCl in 200 mL of EtOH to give after chromatography on silica (eluted with 5% EtOAc/toluene) 5-tert-butyl-2-methyl-1H-indole-3-acetic acid ethyl ester as an oil.

Analyses: Calc'd for $C_{17}H_{23}NO_2$: C, 74.69; H, 8.48; N, 5.12. Found: C, 72.95; H, 8.36; N, 6.29.

B. 5-tert-Butyl-2-methyl-1-(phenylmethyl)-1H-indole-3-acetic acid ethyl ester. Using the procedure described in Example 1, Part F, 546 mg (2 mmol) of 5-tert-butyl-2-methyl-1H-indole-3-acetic acid ethyl ester was reacted with 80 mg (2 mmol) of 60% NaH/mineral oil and 0.24 mL (2 mmol) of benzyl bromide and after chromatography on silica (eluting with 33% EtOAc/hexane) there was obtained 448 mg(62%) of 5-tert-butyl-2-methyl-1-(2-phenylmethyl)-1H-indole-3-acetic acid ethyl ester, mp, 102°–105° C.

Analyses: Calc'd for $C_{24}H_{29}NO_2$: C, 79.30; H, 8.04; N, 3.85. Found: C, 79.40; H, 8.14; N, 4.04.

C. 5-tert-Butyl-2-methyl-1-(phenylmethyl)-1H-indole-3-acetic acid hydrazide. Using the method described in Example 1, Part G, 396 mg (1.1 mmol) of 5-tert-butyl-2-methyl-1-(phenylmethyl)-1H-indole-3-acetic acid ethyl ester was reacted with 2.0 mL of hydrazine to give after crystallizing from MeOH 89 mg (23% yield) of 5-tert-butyl-2-methyl-1-(phenylmethyl)-1H-indole-3-acetic acid hydrazide, mp, 149°–151° C.

Analyses: Calc'd for $C_{22}H_{27}N_3O$: C, 75.61; H, 7.79; N, 12.04. Found: C, 75.41; H, 7.76; N, 12.30.

Example 61

Preparation of 5-Hydroxy-2-methyl-1-(phenylmethyl)-1H-indole-3-acetic acid hydrazide.

To a solution of 165 mg (0.51 mmol) of 5-methoxy-2-methyl-1-(phenylmethyl)-1H-indole-3-acetic acid hydrazide (Example 17, Part B) in 30 mL of $CH_2Cl_2$ was added 1.0 mL of 1M $BBr_3$ in $CH_2Cl_2$ and the mixture stirred for 1.5 hours, then an addition 0.5 mL of the $BBr_3$ solution was added. After 1.5 hours, the reaction mixture was washed with $Na_2CO_3$ solution, dried ($Na_2SO_4$), and concentrated at reduce pressure. The residue was chromatographed on silica eluting with 2% MeOH/$CH_2Cl_2$→5% MeOH/$CH_2Cl_2$ to give 60 mg (39% yield) of 5-hydroxy-2-methyl-1-(phenylmethyl)-1H-indole-3-acetic acid hydrazide, mp, 216°–219° C.

Analyses: Calc'd for $C_{18}H_{19}N_3O_2$: C, 69.88; H, 6.19; N, 13.58. Found: C, 69.65; H, 6.25; N, 13.46.

Example 62

Preparation of 2-Methyl-1-(phenylmethyl)-5-[(2-quinolyl)methoxy]-1H-indole-3-acetic acid hydrazide.

A. 5-Methoxy-2-methyl-1H-indole-3-acetic acid methyl ester. A solution of 12.2 g (0.0557 mol) of 5-methoxy-2-methyl-1H-indole-3-acetic acid in 150 mL of MeOH and 1 mL of sulfuric acid was heated to maintain reflux for 15 hours. After cooling, the mixture was diluted with sodium bicarbonate solution and extracted with EtOAc. The EtOAc solution was washed with saturated NaCl solution and dried ($Na_2SO_4$). The solvent was removed at reduce pressure to give 13 g of crude 5-methoxy-2-methyl-1H-indole-3-acetic acid methyl ester.

B. 5-Methoxy-2-methyl-1-(phenylmethyl)-1H-indole-3-acetic acid. The crude 5-methoxy-2-methyl-1H-indole-3-acetic acid methyl ester from A (56 mmol) was dissolved in 250mL of DMF and approximately 10 mL of THF and 2.5 g (62 mmol) of 60% NaH/mineral oil added. After 0.5 h, 8 mL (67 mmol) of benzyl bromide was added and the mixture stirred for 0.75 hours, diluted with water and extracted with EtOAc. The product was chromatographed on silica (20% ether/hexane→50% ether/hexane) to give 10.1 g of a mixture of 5-methoxy-2-methyl-1-(phenylmethyl)-1H-indole-3-acetic acid methyl and ethyl esters. This mixture was dissolved in 200 mL of EtOH and 20 mL of 5N NaOH and heated to maintain reflux for 20.75 hours. After cooling the mixture was made acidic with 5N HCl and extracted with EtOAc. The EtOAc solution was washed with NaCl, dried ($Na_2SO_4$), and concentrated at reduced pressure to give 7.9 g (46% yield) of crude 5-methoxy-2-methyl-1-(phenylmethyl)-1H-indole-3-acetic acid.

C. 5-Hydroxy-2-methyl-1-(phenylmethyl)-1H-indole-3-acetic acid methyl ester. Three mL (30 mmol) of $BBr_3$ was added to 3.1 g (10 mmol) of 5-methoxy-2-methyl-1-(phenylmethyl)-1H-indole-3-acetic acid in 250 mL of $CH_2Cl_2$ and the mixture stirred for 17 hours. After stirring with 1N HCl, some EtOH was added, the organic layer separated, washed with saturated NaCl solution, dried and concentrated at reduced pressure to give 2.95 g(100% yield) of crude 5-hydroxy-2-methyl-1-(phenylmethyl)-1H-indole-3-acetic acid. A methanol solution of 1.7 g of the material was treated with sulfuric acid as described in Part A to give after silica gel chromatography (30% ether/hexane→60% ether/hexane) 1.5 g of 5-hydroxy-2-methyl-1-(phenylmethyl)-1H-indole-3-acetic acid methyl ester.

D. 2-Methyl-1-(phenylmethyl)-5-[(2-quinolyl)methoxy]-1H-indole-3-acetic acid methyl ester. Using the procedure described in Example 1, Part F, 750 mg (2.4 mmol) of 5-hydroxy-2-methyl-1-(phenylmethyl)-1H-indole-3-acetic acid methyl ester, 100 mg (92.5 mmol) of 60% NaH/mineral oil and 500 mg (2.8 mmol) of 2-chloromethylquinoline were reacted to give after silica chromatography (eluted with $CH_2Cl_2$→2% MeOH/$CH_2Cl_2$) 1.1 g (65% yield) of 2-methyl-1-(phenylmethyl)-5-[(2-quinolyl)methoxy]-1H-indole-3-acetic acid methyl ester, mp, 113°–114° C.

Analyses: Calc'd for $C_{29}H_{26}N_2O_3$: C, 77.31; H, 5.82; N, 6.22. Found: C, 77.41; H, 5.89; N, 6.09.

E. 2-Methyl-1-(phenylmethyl)-5-[(2-quinolyl)methoxy]-1H-indole-3-acetic acid hydrazide. The method in Example 1, Part G was used to react 700 mg (1.55 mmol) of 2-methyl-1-(phenylmethyl)-5-[(2-quinolyl)methoxy]-1H-indole-3-acetic acid methyl ester and 3 mL of hydrazine to give after cooling and filtering the reaction mixture, 450 mg (64% yield) of 2-Methyl-1-(phenylmethyl)-5-[(2-quinolyl)methoxy]-1H-indole-3-acetic acid hydrazide, mp, 195°–197° C.

Analyses: Calc'd for $C_{28}H_{26}N_4O_2$: C, 74.65; H, 5.82; N, 12.43. Found: C, 74.69; H, 5.82; N, 12.33.

Example 63

Preparation of 1-[(4-Chlorophenyl)methyl]-2-methyl-5-[(2-quinolyl)methoxy]-1H-indole-3-acetic acid hydrazide.

A. 1-[(4-Chlorophenyl)methyl]-5-methoxy-2-methyl-1H-indole-3-acetic acid. The procedure in Example 63, Part B, was used to react 1.35 g (5.5 mmol) of 5-methoxy-2-methyl-1H-indole-3-acetic acid ethyl ester with 240 mg (6 mmol) of 60% NaH/mineral oil and 970 mg (6 mmol) of p-chlorobenzyl chloride to give 1.4 g of 1-[(4-chlorophenyl)methyl]-2-methyl-5-methoxy-1H-indole-3-acetic acid ethyl ester that had been chromatographed on silica (20% ether/hexane→ 35% ether/hexane). This ester was hydrolyzed with 3 mL of 5N NaOH to give 1.23 g of crude 1-[(4-chlorophenyl)methyl]-5-methoxy-2-methyl-1H-indole-3-acetic acid.

B. 1-[(4-Chlorophenyl)methyl]-5-hydroxy-2-methyl-1H-indole-3-acetic acid methyl ester. Using the methods in Example 63, Part C, 1.2 g (3.5 mmol) of 1-[(4-chlorophenyl)methyl]-5-methoxy-2-methyl-1H-indole-3-acetic acid was treated with 15 mL of 1M $BBr_3$ in $CH_2Cl_2$ to give crude 1-[(4-chlorophenyl)-methyl]-5-hydroxy-2-methyl-1H-indole-3-acetic acid which was treated with sulfuric acid in MeOH to give 1.2 g of 1-[(4-chlorophenyl)methyl]-5-hydroxy-2-methyl-1H-indole-3-acetic acid methyl ester.

C. 1-[(4-Chlorophenyl)methyl]-2-methyl-5-[(2-quinolyl)methoxy]-1H-indole-3-acetic acid methyl ester. Using the procedure described in Example 1, Part F, 750 mg (2.1 mmol) of 1-[(4-chlorophenyl)methyl]-5-hydroxy-2-methyl-1H-indole-3-acetic acid methyl ester, 100 mg (2.5 mmol) of 60% NaH/mineral oil, and 500 mg (2.8 mmol) of 2-chloromethylquinoline were reacted to give using silica chromatography (eluted with $CH_2Cl_2 \rightarrow 2\%$ MeOH/$CH_2Cl_2$) and crystallization from ether/hexane, 565 mg (57% yield) of 1-[(4-chlorophenyl)methyl]-2-methyl-5-[(2-quinolyl)methoxy]-1H-indole-3-acetic acid methyl ester, mp, 101°–103° C.

Analyses: Calc'd for $C_{29}H_{25}ClN_2O_3$: C, 71.82; H, 5.20; N, 5.78; Cl, 7.31. Found: C, 72.03; H, 5.29; N, 5.65; Cl 7.59.

D. 1-[(4-Chlorophenyl)methyl]-2-methyl-5-[(2-quinolyl)methoxy]-1H-indole-3-acetic acid hydrazide. The method in Example 1, Part G, was used to react 680 mg (1.4 mmol) of 1-[(4-chlorophenyl)methyl]-2-methyl-5-[(2-quinolyl)methoxy]-1H-indole-3-acetic acid methyl ester and 3 mL of hydrazine to give after crystallizing from EtOH 440 mg (65% yield) of 1-[(4-chlorophenyl)methyl]-2-methyl-5-[(2-quinolyl)methoxy]-1H-indole-3-acetic acid hydrazide, mp 191°–193° C.

Analyses: Calc'd for $C_{28}H_{25}ClN_4O_2$: C, 69.34; H, 5.20; N, 11.55; Cl, 7.31. Found: C, 68.77; H, 5.20; N, 11.42; Cl, 7.87.

Example 64

Preparation of 5-Methoxy-1-(phenylmethyl)-1H-indole-3-propanoic acid hydrazide.

A. 5-Methoxy-1H-indole-3-propanoic acid methyl ester. As in Example 1, Part E, 8.83 g (0.06 mole) of 5-methoxy-1H-indole was treated with 37.5 mL (0.06 mol) of a 1.6M solution of n-butyl lithium in hexane, 60 ml (0.06 mol) of a 1M solution of $ZnCl_2$ in ether, and 6.7 mL (0.06 mol) of methyl 2-bromopropionate to give after chromatography on silica (10% EtOAc/hexane) 7.0 g (50%) of 5-methoxy-1H-indole-3-propanoic acid methyl ester as an oil.

Analyses: Calc'd for $C_{13}H_{15}NO_3$: C, 66.94; H, 6.48; N, 6.00. Found: C, 67.20; H, 6.69; N, 6.08.

B. 5-Methoxy-1-(phenylmethyl)-1H-indole-3-propanoic acid methyl ester. Using the procedure described in Example 1, Part F, 466 mg (2 mmol) of 5-methoxy-1H-indole-3-propanoic acid methyl ester was reacted with 80 mg (2 mmol) of 60% NaH/mineral oil and 0.24 mL (2 mmol) of benzyl bromide to give after silica chromatography (25% EtOAc/hexane) 469 mg (73%) of 5-methoxy-1-(phenylmethyl)-1H-indole-3-propanoic acid methyl ester as an oil.

Analyses: Calc'd for $C_{20}H_{21}NO_3$: C, 74.28; H, 6.54; N, 4.33. Found: C, 74.49; H, 6.80; N, 4.32.

C. 5-Methoxy-1-(phenylmethyl)-1H-indole-3-propanoic acid hydrazide. Using the method described in Example 1, Part G, 444 mg (1.4 mmol) of 5-methoxy-1-(phenylmethyl)-1H-indole-3-propanoic acid methyl ester was reacted with 1.4 mL of hydrazine to give after crystallizing from MeOH 279 mg (62% yield) of 5-methoxy-1-(phenylmethyl)-1H-indole-3-propanoic acid hydrazide, mp 152°–156° C).

Analyses: Calc'd for $C_{19}H_{21}N_3O_2$: C, 70.57; H, 6.55; N, 12.99. Found: C, 70.41 H, 6.62; N, 13.11.

Example 65

Preparation of 5-Methoxy-2-methyl-1-(phenylmethyl)-1H-indole-3-propanoic acid hydrazide.

A. 5-Methoxy-2-methyl-1H-indole-3-propanoic acid methyl ester. As in Example 1, Part E, 9.67 g (0.06 mole) of 5-methoxy-2-methyl-1H-indole was treated with 37.5 mL (0.06 mol) of a 1.6M solution of n-butyl lithium in hexane, 60 ml (0.06 mol) of a 1M solution of $ZnCl_2$ in ether, and 6.7 mL (0.06 mol) of methyl 2-bromopropionate to give after chromatography on silica (10% EtOAc/hexane) 8.7 g (59%) of 5-methoxy-2-methyl-1H-indole-3-propanoic acid methyl ester as an oil.

Analyses: Calc'd for $C_{14}H_{17}NO_3$: C, 68.00; H, 6.93; N, 5.60. Found: C, 67.73; H, 6.92; N, 5.72.

B. 5-Methoxy-2-methyl-1-(phenylmethyl)-1H-indole-3-propanoic acid methyl ester. A solution of 2.47 g (0.01 mol) of 5-methoxy-2-methyl-1H-indole-3-propanoic acid methyl ester in 40 mL of DMF was treated with 1.12 g (0.01 mol) of potassium t-butoxide, stirred 0.5 hour, and 1.15 mL (0.01 mol) of benzyl chloride added. After 72 hours, the reaction mixture was diluted with water, extracted with EtOAc, the EtOAc solution was washed four times with water and dried over $Na_2SO_4$. After concentrating at reduced pressure, the product was purified by chromatography on silica, eluting with a gradient, toluene$\rightarrow$10% EtOAc/toluene, to give 2.03 g (61% yield) of 5-methoxy-2-methyl-1-(phenylmethyl)-1H-indole-3-propanoic acid methyl ester as an oil.

Analyses: Calc'd for $C_{21}H_{23}NO_3$: C, 74.75; H, 6.87; N, 4.15. Found: C, 74.69; H, 7.05; N, 4.29.

C. 5-Methoxy-2-methyl-1-(phenylmethyl)-1H-indole-3-propanoic acid hydrazide. Using the method described in Example 1, Part G, 2.0 g (0.054 mol) of 5-methoxy-2-methyl-1-(phenylmethyl)-1H-indole-3-propanoic acid methyl ester was reacted with 5 mL of hydrazine to give after chromatography(eluting with ($CH_2Cl_2 \rightarrow 10\%$ MeOH/ $CH_2Cl_2$) 0.8 g (40% yield) of 5-methoxy-2-methyl-1-(phenylmethyl)-1H-indole-3-propanoic acid hydrazide as a waxy material.

Analyses: Calc'd for $C_{20}H_{23}N_3O_2$: C, 71.19; H, 6.87; N, 12.45. Found: C, 71.09; H, 7.07; N, 12.15.

Example 66

Preparation of 5-Methoxy-1-(phenylmethyl)-1H-indole-3-butanoic acid hydrazide.

A. 5-Methoxy-1H-indole-3-butanoic acid ethyl ester. As in Example 1, Part E, 8.83 g (0.06 mole) of 5-methoxy-1H-indole was treated with 37.5 mL (0.06 mol) of a 1.6M solution of n-butyl lithium in hexane, 60 ml (0.06 mol) of a 1M solution of $ZnCl_2$ in ether, and 8.86 mL (0.06 mol) of ethyl 2-bromobutyrate to give after chromatography on silica (eluted with a gradient, toluene$\rightarrow$10% EtOAc/toluene) 7.8 g (50%) of 5-methoxy-1H-indole-3-butanoic acid ethyl ester as an oil.

Analyses: Calc'd for $C_{15}H_{19}NO_3$: C, 68.94; H, 7.33; N, 5.36. Found: C, 68.84; H, 7.50; N, 5.50.

B. 5-Methoxy-1-(phenylmethyl)-1H-indole-3-butanoic acid ethyl ester. Using the procedure described in Example 1 Part F, 496 mg (1.9 mmol) of 5-methoxy-1H-indole-3-butanoic acid ethyl ester was reacted with 80 mg (2 mmol) of 60% NaH/mineral oil and 0.24 mL (2 mmol) of benzyl bromide to give after silica chromatography (25% EtOAc/hexane) 526 mg (79%) of 5-methoxy-1-(phenylmethyl)-1H-indole-3-butanoic acid ethyl ester as an oil.

Analyses: Calc'd for $C_{22}H_{25}NO_3$: C, 75.19; H, 7.17; N, 3.99. Found: C, 74.99; H, 7.13; N, 4.28.

C. 5-Methoxy-1-(phenylmethyl)-1H-indole-3-butanoic acid hydrazide. Using the method described in Example 1, Part G, 525 mg (1.4 mmol) of 5-methoxy-1-(phenylmethyl)-1H-indole-3-butanoic acid ethyl ester was reacted with 1.4 mL of hydrazine to give after crystallization from MeOH 232 mg (51% yield) of 5-methoxy-1-(phenylmethyl)-1H-indole-3-butanoic acid hydrazide, mp, 140°–141° C.

Analyses: Calc'd for $C_{20}H_{23}N_3O_2$: C, 71.19; H, 6.87; N, 12.45. Found: C, 70.95; H, 6.82; N, 12.46.

Example 67

Preparation of 5-Methoxy-2-methyl-1-(phenylmethyl)-1H-indole-3-butanoic acid hydrazide.

A. 5-Methoxy-2-methyl-1H-indole-3-butanoic acid ethyl ester. As in Example 1, Part E, 9.67 g (0.06 mole) of 5-methoxy-2-methyl-1H-indole was treated with 37.5 mL (0.06 mol) of a 1.6M solution of n-butyl lithium in hexane, 60 ml (0.06 mol) of a 1M solution of $ZnCl_2$ in ether, and 8.86 mL (0.06 mol) of ethyl 2-bromobutyrate to give after chromatography on silica (eluted with a gradient, toluene→10% EtOAc/toluene) 9.3 g (56%) of 5-methoxy-2-methyl-1H-indole-3-butanoic acid ethyl ester as an oil.

Analyses: Calc'd for $C_{16}H_{21}NO_3$: C, 69.79; H, 7.69; N, 5.09. Found: C, 69.51; H, 7.71; N, 5.39.

B. 5-Methoxy-2-methyl-1-(phenylmethyl)-1H-indole-3-butanoic acid ethyl ester. Using the procedure described in Example 1, Part F, 522 mg (1.9 mmol) of 5-methoxy-2-methyl-1H-indole-3-butanoic acid ethyl ester was reacted with 80 mg (2 mmol) of 60% NaH/mineral oil and 0.24 mL (2 mmol of benzyl bromide to give after silica chromatography (25% EtOAc/hexane) 550 mg(79%) of 5-methoxy-2-methyl-1-(phenylmethyl)-1H-indole-3-butanoic acid ethyl ester as an oil.

Analyses: Calc'd for $C_{23}H_{27}NO_3$: C, 75.59; H, 7.45; N, 3.83. Found: C, 75.72; H, 7.68; N, 3.82.

C. 5-Methoxy-2-methyl-1-(phenylmethyl)-1H-indole-3-butanoic acid hydrazide. Using the method described in Example 1, Part G, 525 mg (1.4 mmol) of 5-methoxy-2-methyl-1-(phenylmethyl)-1H-indole-3-butanoic acid ethyl ester was reacted with 1.4 mL of hydrazine to give after chromatography (eluting with (50% EtOAc/hexane, then EtOAc) 172 mg (35% yield) of 5-methoxy-2-methyl-1-(phenylmethyl)-1H-indole-3-butanoic acid hydrazide as an oil.

Analyses: Calc'd for $C_{21}H_{25}N_3O_2$: C, 71.77; H, 7.17; N, 11.96. Found C, 71.99; H, 7.44; N, 12.16.

Example 68

Preparation of 5-Carboxy-[(3-chlorophenyl)methyl]-2-methyl-1H-indole-3-acetic acid hydrazide.

A. 5-Ethoxycarbonyl-2-methyl-1H-indole-3-acetic acid ethyl ester. Dry hydrogen chloride was bubbled into a solution of 25 g (0.1643 mol) of 4-hydrazinobenzoic acid and 20.5 mL (0.2 mol) of levulenic acid for 0.5 hour and the reaction mixture heated to maintain reflux for 20 hours. After cooling, the mixture was concentrated at reduced pressure, water added, and the mixture extracted with EtOAc/ether. After drying ($Na_2SO_4$), the solution was concentrated and the residue chromatographed on silica and eluted with a solvent gradient, toluene→20% EtOAc/toluene to give in the later fractions 12 g of a mixture of 5-ethoxycarbonyl-2-methyl-1H-indole-3-acetic acid ethyl ester and the intermediate hydrazone. This mixture was treated again with dry HCl in 250 mL of EtOH and heated to maintain reflux for 16 hours. After cooling, the mixture was poured into water and extracted with EtOAc, the EtOAc solution washed with $Na_2CO_3$ solution and dried ($Na_2SO_4$). Silica chromatography (toluene→20% EtOAc/toluene) gave 3.6 g (7.6% yield) of 5-ethoxycarbonyl-2-methyl-1H-indole-3-acetic acid ethyl ester, mp, 74°–76° C.

Analyses: Calc'd for $C_{16}H_{19}NO_4$: C, 66.42; H, 6.62; N, 4.84. Found: C, 66.54; H, 5.00; N, 10.39.

B. 1-[(3-Chlorophenyl)methyl]-5-ethoxycarbonyl-2-methyl-1H-indole-3-acetic acid ethyl ester. Using the procedure described in Example 3 Part E, 1.1 g (0.0038 mol) of 5-ethoxycarbonyl-2-methyl-1H-indole-3-acetic acid ethyl ester was reacted with 0.43 g (0.0038 mol) of potassium t-butoxide and 0.482 mL (0.0038 mol) of 3-chlorobenzyl chloride to give after silica chromatography (gradient, toluene→20% EtOAc/toluene), 0.54 g (34%) of 1-[(3-chlorophenyl)methyl]-5-ethoxycarbonyl-2-methyl-1H-indole-3-acetic acid ethyl ester, mp, 100°–102° C.

Analyses: Calc'd for $C_{23}H_{24}ClNO_4$: C, 66.74; H, 5.85; N, 3.38. Found: C, 66.68; H, 5.93; N, 3.20.

C. 5-Carboxy-1-[(3-chlorophenyl)methyl]-2-methyl-1H-indole-3-acetic acid methyl ester. A solution of 0.27 g (0.65 mmol) of 1-[(3-chlorophenyl)methyl]-5-ethoxycarbonyl-2-methyl-1H-indole-3-acetic acid ethyl ester and 2 mL of 5N NaOH in 40 mL of EtOH was heated to maintain reflux for 4 hours. After cooling, the mixture was diluted with water and extracted with EtOAc. The EtOAc solution which contained some precipitate was concentrated at reduced pressure and the residue was crystallized from MeOH to give 100 mg (43% yield) of 5-carboxy-1-[(3-chlorophenyl)methyl]-2-methyl-1H-indole-3-acetic acid methyl ester, mp, 216°–217° C.

Analyses: Calc'd for $C_{20}H_{18}ClNO_4$: C, 64.60; H, 4.88; N, 3.77. Found: C, 64.49; H, 5.00; N, 3.10.

D. 5-Carboxy-1-[(3-chlorophenyl)methyl]-2-methyl-1H-indole-3-acetic acid hydrazide. Using the method described in Example 1, Part G, 660 mg (1.6 mmol) of 5-carboxy-1-[(3-chlorophenyl)methyl]-2-methyl-1H-indole-3-acetic acid methyl ester was reacted with 1.0 mL of hydrazine to give after crystallization from EtOH, 10 mg (10% yield) of 5-carboxy-1-[(3-chlorophenyl)methyl]-2-methyl-1H-indole-3-acetic acid hydrazide, mp, 216°–217° C.

Analyses: Calc'd for $C_{19}H_{18}ClN_3O_3$: C, 61.37; H, 4.88; N, 11.30. Found: C, 61.16; H, 5.07; N, 11.54.

Example 69

Preparation of 1-[(3-Chlorophenyl)methyl]-5-hydrazinocarbonyl-2-methyl-1H-indole-3-acetic acid hydrazide. Using the method described in Example 1, Part G, 270 mg (0.65 mmol) of 1-[(3-chlorophenyl)methyl]-5-ethoxycarbonyl-2-methyl-1H-indole-3-acetic acid ethyl ester (Example 71, Part B) was reacted with 2 mL of hydrazine to give after crystallization from EtOH 130 mg (52% yield) of 1-[(3-chlorophenyl)methyl]-5-hydrazinocarbonyl-2-methyl-1H-indole-3-acetic acid hydrazide, mp, 245°–246° C.

Analyses: Calc'd for $C_{19}H_{20}ClN_5O_2$: C, 59.14; H, 5.23; N, 18.15. Found: C, 59.13; H, 5.30; N, 17.93.

Example 70

Preparation of 5-Hydrazinocarbonyl-2-methyl-1-(phenylmethyl)-1H-indole-3-acetic acid hydrazide.

A. 5-Ethoxycarbonyl-2-methyl-1-(phenylmethyl)-1H-indole-3-acetic acid ethyl ester. Using the procedure described in Example 1, Part F, 2.18 g (7.5 mmol) of 5-ethoxycarbonyl-2-methyl-1H-indole-3-acetic acid ethyl ester was reacted with 320 mg (8 mmol) of 60% NaH/mineral oil and 1.0 mL (8.4 mmol) of benzyl bromide to give after silica chromatography (25% ether/hexane→50% ether/hexane) 1.6 g (56%) of 5-ethoxycarbonyl-2-methyl-1-(phenylmethyl)-1H-indole-3-acetic acid ethyl ester.

B. 5-Carboxy-2-methyl-1-(phenylmethyl)-1H-indole-3-acetic acid ethyl ester. A solution of 1.6 g (4.2 mmol) of 5-ethoxycarbonyl-2-methyl-1-(phenylmethyl)-1H-indole-3-acetic acid ethyl ester and 4.2 mL of 1N NaOH in 75 mL of EtOH was stirred 2.25 hours, 10 mL of 1N NaOH added, and stirred an additional 18.5 hours. The reaction mixture was acidified with 1N HCl, extracted with EtOAc, the EtOAc solution washed with saturated NaCl solution, dried(Na$_2$SO$_4$), and concentrated at reduced pressure. The residue was heated in 150 mL of EtOH for 4.5 hours, and left at room temperature for 96 hours. After concentrating at reduced pressure, the residue was chromatographed on silica (25% ether/hexane→50% ether/hexane) to give 110 mg (7.5% yield) of 5-carboxy-2-methyl-1-(phenylmethyl)-1H-indole-3-acetic acid ethyl ester.

C. 5-Hydrazinocarbonyl-2-methyl-1-(phenylmethyl)-1H-indole-3-acetic acid hydrazide. Using the method described in Example 1, Part G, 110 mg (0.31 mmol) of 5-carboxy-2-methyl-1-(phenylmethyl)-1H-indole-3-acetic acid ethyl ester was reacted with 3 mL of hydrazine (total reflux time, 78r) to give on cooling of the reaction mixture 40 mg (38% yield) of 5-hydrazinocarbonyl-2-methyl-1-(phenylmethyl)-1H-indole-3-acetic acid hydrazide, mp, >255° C.

Analyses: Calc'd for C$_{19}$H$_{21}$N$_5$O$_2$: C, 64.94; H, 6.02; N, 19.93. Found: C, 65.15; H, 6.14; N, 19.82.

Example 71

Preparation of 4-[[3-(2-Hydrazino-2-oxoethyl)-2-methyl-1-(phenylmethyl)-1H-indol-5-yl]oxy]butanoic acid.

A solution of 310 mg (1 mmol) of 5-hydroxy-2-methyl-1-(phenylmethyl)-1H-indole-3-acetic acid hydrazide (Example 62) in 25 mL of DMSO was treated with 45 mg (1.1 mmol) of 60% NaH/mineral oil and after 0.25 hour, 0.16 mL (1.1 mmol) of ethyl 4-bromobutyrate was added. The mixture was stirred for 4 hours, diluted with water and extracted with EtOAc. The EtOAc solution was washed with NaCl solution, dried (Na2SO4), and concentrated at reduced pressure. The residue was chromatographed on silica eluting with CH$_2$Cl$_2$→4% MeOH/CH$_2$C$_2$, to give 290 mg (68% yield) of 4-[[3-(2-hydrazino-2-oxoethyl)-2-methyl-1-(phenylmethyl)-1H-indole-5-yl]oxy]butanoic acid ethyl ester. This ester (0.685 mmol) and 2 mL of 2N NaOH in 25 mL of EtOH and 5 mL of THF was stirred for 22.5 hours. The mixture was diluted with water, made acidic to pH 6 with 1N HCl and extracted with EtOAc, the EtOAc dried (Na2SO4), and concentrated at reduced pressure. The residue was dissolved in EtOH and precipitated with ether to give 50 mg (47% yield) of 4-[[3-(2-hydrazino-2-oxoethyl)-2-methyl-1-(phenylmethyl)-1H-indole-5-yl]oxy]butanoic acid, mp, 160° C. (decomposition).

Analysis: Calc'd for C22H25N3O4: C, 66.82; H, 6.37; N, 10.63. Found: C, 66.19; H, 6.23; N, 9.32.

Therapeutic use of 1H-indole-3-acetic acid hydrazides

Tests of the 1H-indole-3-acetic acid hydrazides described herein have shown they achieve their beneficial therapeutic action principally by direct inhibition of human sPLA$_2$, and not by acting as antagonists for arachidonic acid, nor other active agents below arachidonic acid in the arachidonic acid cascade, such as 5-lipoxygenases, cyclooxygenases, and etc.

The method of the invention for inhibiting sPLA$_2$ mediated release of arachidonic acid comprises contacting sPLA$_2$ with an therapeutically effective amount of 1H-indole-3-acetic acid hydrazide and pharmaceutically acceptable salts thereof.

A preferred method of inhibiting sPLA$_2$ mediated release of fatty acids comprises contacting sPLA$_2$ with a therapeutically effective amount of 1H-3-acetic acid hydrazide, where said hydrazide is substituted at the 1 position with a benzyl or substituted benzyl group, and pharmaceutically acceptable salts thereof.

More generally, sPLA$_2$ mediated release of arachidonic acid may be inhibited by a process which comprises contacting sPLA$_2$ with an therapeutically effective amount of 1H-indole-3-acetic acid hydrazide and pharmaceutically acceptable salts thereof, represented by the formula(VI):

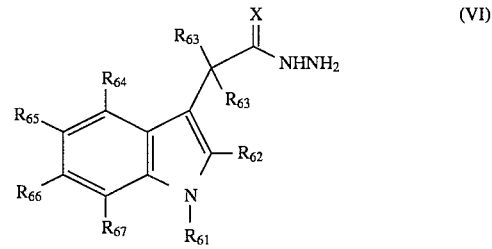

X is oxygen or sulfur;

$R_{61}$ is selected from groups (i), (ii) and (iii) where;
(i) is $C_4$–$C_{20}$ alkyl, $C_4$–$C_{20}$ alkenyl, $C_4$–$C_{20}$ alkynyl, $C_4$–$C_{20}$ haloalkyl, $C_4$–$C_{12}$ cycloalkyl, or
(ii) is aryl or aryl substituted by halo, —CN, —CHO, —OH, —SH, $C_1$–$C_{10}$ alkylthio, $C_1$–$C_{10}$ alkoxylthio, carboxyl, amino, or hydroxyamino;
(iii) is

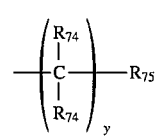

where y is from 1 to 8, $R_{74}$ is, independently, hydrogen or $C_1$–$C_{10}$ alkyl, and $R_{75}$ is aryl or aryl substituted by halo, —CN, —CHO, —OH, nitro, phenyl, —SH, $C_1$–$C_{10}$ alkylthio, $C_1$–$C_{10}$ alkoxyl, $C_1$–$C_{10}$ alkyl, amino, hydroxyamino or a substituted or unsubstituted 5 to 8 membered heterocyclic ring, or both $R_{74}$ taken together are =O;

$R_{62}$ is hydrogen, halo, $C_1$–$C_3$ alkyl, ethenyl, $C_1$–$C_2$ alkylthio, $C_1$–$C_2$ alkoxy, —CHO, —CN;

each R63 is independently hydrogen, or halo;

$R_{64}$, $R_{65}$, $R_{66}$, and $R_{67}$ are each independently hydrogen, $C_1$–$C_{10}$ alkyl, $C_1$–$C_{10}$ alkenyl, $C_1$–$C_{10}$ alkynyl, $C_3$–$C_8$ cycloalkyl, aryl, aralkyl, or any two adjacent hydrocarbyl groups in the set $R_{64}$, $R_{65}$, $R_{66}$, and $R_{67}$ combined with the ring carbon atoms to which they are attached to form a 5 or 6 membered substituted or unsubstituted carbocyclic ring; or $C_1$–$C_{10}$ haloalkyl, $C_1$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazide, hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$–$C_{10}$ alkyl, $C_1$–$C_{10}$ hydroxyalkyl, or taken together with N, $R_{82}$ and $R_{83}$ form a 5 to 8 membered heterocyclic ring; or a group having the formula;

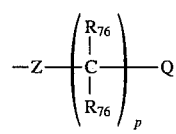

where,
each $R_{76}$ is independently selected from hydrogen, $C_1$–$C_{10}$ alkyl, hydroxy, or both $R_{76}$ taken together are =O;

p is 1 to 5,

Z is a bond, —O—, —N($C_1$–$C_{10}$ alkyl)—, —NH, or —S—;

and

Q is —CON($R_{82}R_{83}$), -5-tetrazolyl, —SO$_3$H,

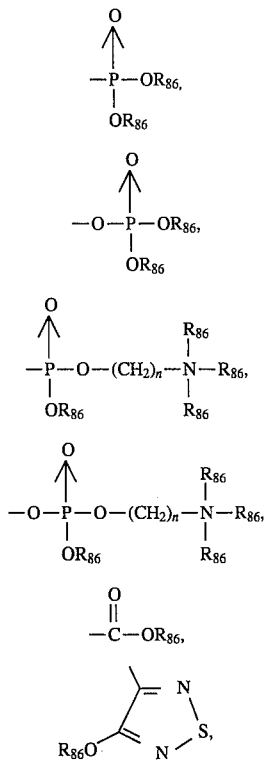

where $R_{86}$ is hydrogen a metal, or $C_1$–$C_{10}$ alkyl.

The method of this invention for inhibiting sPLA$_2$ mediated release of arachidonic acid finds specific application in treatment of septic shock in humans. Thus, according to the method of this invention septic shock is treated by administering to a human a therapeutically effective dose of 1H-indole-3-acetic acid hydrazide and pharmaceutically acceptable salts thereof. A preferred treatment for septic shock comprises administering to a human a therapeutically effective dose of a 1H-indole-3-acetic acid hydrazide substituted at the 1 position with a benzyl or substituted benzyl group and pharmaceutically acceptable salts thereof. Still another preferred treatment for septic shock comprises administering to a human a therapeutically effective dose of a 1H-indole-3-acetic acid hydrazide substituted at the 2 position with a group containing halogen, oxygen, nitrogen or sulfur, and pharmaceutically acceptable salts thereof.

Pharmaceutical Formulations

As previously noted the compounds of this invention are useful for inhibiting sPLA$_2$ mediated release of fatty acids such as arachidonic acid. By the term, "inhibiting" is meant the prevention or therapeutically significant reduction in release of sPLA$_2$ initiated fatty acids by the compounds of the invention.

The specific dose of a compound administered according to this invention to obtain therapeutic or prophylactic effects will, of course, be determined by the particular circumstances surrounding the case, including, for example, the compound administered, the route of administration and the condition being treated. Typical daily doses will contain a non-toxic dosage level of from about 0.01 mg/kg to about 50 mg/kg of body weight of an active compound of this invention.

The compound can be administered by a variety of routes including oral, aerosol, rectal, transdermal, subcutaneous, intravenous, intramuscular, and intranasal. Pharmaceutical formulations of the invention are prepared by combining (e.g., mixing) a therapeutically effective amount of the 1H-indole-3-acetic acid hydrazides of the invention together with a pharmaceutically acceptable carrier or diluent therefor. The compounds of the present invention are preferably formulated prior to administration.

The active ingredient in such formulations comprises from 0.1% to 99.9% by weight of the formulation. By "pharmaceutically acceptable" it is meant the carrier, diluent or excipient must be compatible with the other ingredients of the formulation and not deleterious to the recipient thereof.

The present pharmaceutical formulations are prepared by known procedures using well known and readily available ingredients. In making the compositions of the present invention, the active ingredient will usually be admixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, or can be in the form of tablets, pills, powders, lozenges, elixirs, suspensions, imulsions, solutions, syrups, aerosols (as a solid or in a liquid medium), or ointment, containing, for example, up to 10% by weight of the active compound.

Tablets for oral administration may contain suitable excipients such as calcium carbonate, sodium carbonate, lactose, calcium phosphate, together with disintegrating agents, such as maize, starch, or alginic acid, and/or binding agents, for example, gelatin or acacia, and lubricating agents such as magnesium stearate, stearic acid, or talc.

The following formulation examples are illustrative only and are not intended to limit the scope of the invention in any way. The term, "Active Ingredient", means a 1H-indole-3-acetic acid hydrazide compound of the invention or a pharmaceutically acceptable salt thereof.

Formulation 1

A tablet is prepared using the ingredients below:

|  | Quantity - (mg/capsule) |
|---|---|
| Active Ingredient | 250 |
| Cellulose, microcrystalline | 400 |
| Silicon dioxide, fumed | 10 |
| Stearic acid | 5 |

The components are blended and compressed to form tablets. each weighing 665 mg.

Formulation 2

An aerosol solution is prepared containing the following components:

|  | Weight |
|---|---|
| Active Ingredient | 0.25 |
| Ethanol | 25.75 |
| Chlorodifluoromethane propellant | 70.00 |

The Active Ingredient is mixed with ethanol and the mixture added to a portion of the propellant, cooled to −30° C. and transferred to a filling device. The required amount is then fed to a stainless steel container and diluted with the remainder of the propellant. The valve units are then fitted to the container.

Assay Experiments

Assay Example 1

The following chromogenic assay procedure was used to identify and evaluate inhibitors of recombinant human secreted phospholipase $A_2$. The assay described herein has been adapted for high volume screening using 96 well microtiter plates. A general description of this assay method is found in the article, "Analysis of Human Synovial Fluid Phospholipase $A_2$ on Short Chain Phosphatidylcholine-Mixed Micelles: Development of a Spectrophotometric Assay Suitable for a Microtiterplate Reader", by Laure J. Reynolds, Lori L. Hughes, and Edward A Dennis, *Analytical Biochemistry*, 204, pp. 190–197, 1992:

Reagents, the disclosure of which is incorporated herein by reference.

REACTION BUFFER

CaCl2.2H20 (1.47 g/L)

KCl (7.455 g/L)

Bovine Serum Albumin (fatty acid free) (1 g/L) (Sigma A-7030, product of Sigma Chemical Co. St. Louis Mo., USA)

TRIS HCl (3.94 g/L)

pH 7.5 (adjust with NaOH)

ENZYME BUFFER 0.05 NaOAc.3H20, pH 4.5

0.2 NaCl

Adjust pH to 4.5 with acetic acid

DTNB 5,5"-dithiobis-2-nitrobenzoic acid

RACEMIC DIHEPTANOYL THIO - PC racemic 1,2-bis(heptanoylthio)-1,2-dideoxy-sn-glycero-3-phosphorylcholine TRITON X-100™ prepare at 6.249 mg/ml in reaction buffer to equal 10 uM.

REACTION MIXTURE

A measured volume of racemic dipheptanoyl thio PC supplied in chloroform at a concentration of 100 mg/ml is taken to dryness and redissolved in 10 millimolar TRITON X-100™ nonionic detergent aqueous solution. Reaction Buffer is added to the solution, then DTNB to give the Reaction Mixture.

The reaction mixture thus obtained contains 1 mM diheptanoly thio-PC substrate, 0.29 mM Triton X-100™ detergent, and 0.12 mM DTMB in a buffered aqueous solution at pH 7.5.

Assay Procedure:
1. Add 0.2 ml reaction mixture to all wells;
2. Add 10 ul test compound (or solvent blank) to appropriate wells, mix 20 seconds;
3. Add 50 nanograms of $sPLA_2$ (10 microliters) to appropriate wells;
4. Incubate plate at 40° C. for 30 minutes;
5. Read absorbance of wells at 405 nanometers with an automatic plate reader.

All compounds were tested in triplicate. Typically, compounds were tested at a final concentration of 5 ug/ml. Compounds were considered active when they exhibited 40% inhibition or greater compared to uninhibited control reactions when measured at 405 nanometers. Lack of color development at 405 nanometers evidenced inhibition. Compounds initially found to be active were reassayed to confirm their activity and, if sufficiently active, $IC_{50}$ values were determined. Typically, the IC50 values were determined by diluting test compound serially two-fold such that the final concentration in the reaction ranged from 45 ug/mL to 0.35 ug/ml. More potent inhibitors required significantly greater dilution. In all cases, % inhibition measured at 405 nanometers generated by enzyme reactions containing inhibitors relative to the uninhibited control reactions was determined. Each sample was titrated in triplicate and result values were averaged for plotting and calculation of $IC_{50}$ values. $IC_{50}$ values were determined by plotting log concentration versus log of inhibition values in the range from 10–90% inhibition. $IC_{50}$ values were determined at least three times for each compound tested. The mean value of these determinations is listed in the following Table.

| Results of Human Secreted Phospholipase $A_2$ Inhibition Tests | |
|---|---|
| Example | Inhibition of human secreted $PLA_2$ $IC_{50}$ ± mean deviation (3–5 tests) |
| 1 | 0.80 ± 0.25 uM |
| 2 | 0.47 ± 0.15 uM |
| 3 | 0.42 ± 0.19 uM |
| 4 | 5.17 ± 6.71 uM |
| 5 | 70.52 ± 2.89 uM |
| 6 | 0.67 ± 0.24 uM |
| 7 | 1.52 ± 0.56 uM |
| 8 | 1.14 ± 0.44 uM |
| 9 | 2.31 ± 0.65 uM |
| 10 | 2.36 ± 0.50 uM |
| 11 | 11.05 ± 1.80 uM |
| 12 | 5.49 ± 4.29 uM |
| 13 | 9.88 ± 3.41 uM |
| 14 | 7.08 ± 1.61 uM |
| 15 | >100 uM |
| 16 | 0.86 ± 0.12 uM |
| 17 | 1.71 ± 0.24 uM |
| 18 | 1.02 ± 0.18 uM |
| 19 | 9.28 ± 2.06 uM |
| 20 | 9.39 ± 2.30 uM |
| 21 | 0.64 ± 0.19 uM |
| 22 | 1.54 ± 0.67 uM |
| 23 | 0.89 ± 0.52 uM |
| 24 | 0.26 ± 0.08 uM |
| 25 | 0.94 ± 0.33 uM |
| 26 | 3.26 ± 1.74 uM |
| 27 | 2.18 ± 0.51 uM |
| 28 | 11.67 ± 4.04 uM |
| 29 | 0.84 ± 0.31 uM |
| 30 | 0.61 ± 0.22 uM |
| 31 | 3.00 ± 1.40 uM |

Results of Human Secreted Phospholipase $A_2$ Inhibition Tests

| Example | Inhibition of human secreted $PLA_2$ $IC_{50}$ ± mean deviation (3–5 tests) |
|---|---|
| 32 | 2.28 ± 0.57 uM |
| 33 | 5.96 ± 2.03 uM |
| 34 | 15.22 ± 0.77 uM |
| 35 | 7.12 ± 4.89 uM |
| 36 | 5.32 ± 1.93 uM |
| 37 | 27.18 ± 7.89 uM |
| 38 | 84.19 ± 19.35 uM |
| 39 | 45.85 ± 13.05 uM |
| 40 | 8.15 ± 3.27 uM |
| 41 | 16.76 ± 2.89 uM |
| 42 | 16.49 ± 3.58 uM |
| 43 | 0.39 ± 0.03 uM |
| 44 | 0.43 ± 0.03 uM |
| 45 | 0.60 ± 0.13 uM |
| 46 | 46.05 ± 24.68 uM |
| 47 | 1.49 ± 0.34 uM |
| 48 | 0.74 ± 0.15 uM |
| 49 | 1.63 ± 0.74 uM |
| 50 | 1.02 ± 0.43 uM |
| 51 | 1.34 ± 0.44 uM |
| 52 | 0.71 ± 0.34 uM |
| 53 | 2.06 ± 0.94 uM |
| 54 | 1.02 ± 0.26 uM |
| 55 | 2.06 ± 0.94 uM |
| 56 | 0.86 ± 0.20 uM |
| 57 | 0.93 ± 0.55 uM |
| 58 | 2.21 ± 1.16 uM |
| 59 | 0.76 ± 0.35 uM |
| 60 | 1.02 ± 0.35 uM |
| 61 | 1.39 ± 0.69 uM |
| 62 | 0.36 ± 0.17 uM |
| 63 | 8.46 ± 5.45 uM |
| 64 | 5.90 ± 2.99 uM |
| 65 | 32.64 uM |
| 66 | 9.96 ± 5.61 uM |
| 67 | 24.25 ± 10.71 uM |
| 68 | 0.36 ± 0.03 uM |
| 69 | 2.70 ± 0.38 uM |
| 70 | 2.47 ± 0.64 uM |
| 71 | 0.86 uM |

Assay Example 2

Method:

Male Hartley strain guinea pigs (500–700 g) were killed by cervical dislocation and their heart and lungs removed intact and placed in aerated (95% $O_2$:5% $CO_2$) Krebs buffer. Dorsal pleural strips (4×1×25 mm) were dissected from intact parenchymal segments (8×4×25 mm) cut parallel to the outer edge of the lower lung lobes. Two adjacent pleural strips, obtained from a single lobe and representing a single tissue sample, were tied at either end and independently attached to a metal support rod. One rod was attached to a Grass force-displacement transducer (Model FTO3C, product of Grass Medical Instruments Co., Quincy, Mass., USA). Changes in isometric tension were displayed on a monitor and thermal recorder (product of Modular Instruments, Malvern, Pa.). All tissues were placed in 10 ml jacketed tissue baths maintained at 37° C. The tissue baths were continuously aerated and contained a modified Krebs solution of the following composition (millimolar) NaCl, 118.2; KCl, 4.6; $CaCl_2.2H_2O$, 2.5; $MgSO_4.7H_2O$, 1.2; $NaHCO_3$, 24.8; $KH_2PO_4$, 1.0; and dextrose, 10.0. Pleural strips from the opposite lobes of the lung were used for paired experiments. Preliminary data generated from tension/response curves demonstrated that resting tension of 800 mg was optimal. The tissues were allowed to equilibrate for 45 min. as the bath fluid was changed periodically.

Cumulative concentration-response curves:

Initially tissues were challenged 3 times with KCl (40 mM) to test tissue viability and to obtain a consistent response. After recording the maximal response to KCl the tissues were washed and allowed to return to baseline before the next challenge. Cumulative concentration-response curves were obtained from pleural strips by increasing the agonist concentration ($sPLA_2$) in the tissue bath by half-$log_{10}$ increments while the previous concentration remained in contact with the tissues (Ref.1, supra.) Agonist concentration was increased after reaching the plateau of the contraction elicited by the preceding concentration. One concentration-response curve was obtained from each tissue. To minimize variability between tissues obtained from different animals, contractile responses were expressed as a percentage of the maximal response obtained with the final KCl challenge. When studying the effects of various drugs on the contractile effects of $sPLA_2$, the compounds and their respective vehicles were added to the tissues 30 min. prior to starting the $sPLA_2$ concentration-response curves.

statistical analysis:

Data from different experiments were pooled and presented as a percentage of the maximal KCl responses (mean±S.E.). To estimate the drug induced rightward shifts in the concentration response curves, the curves were analyzed simultaneously using statistical nonlinear modeling methods similar to those described by Waud (1976), Equation 26, p. 163, (Ref.2). The model includes four parameters: the maximum tissue response which was assumed the same for each curve, the $ED_{50}$ for the control curve, the steepness of the curves, and the $PA_2$, the concentration of antagonist that requires a two-fold increase in agonist to achieve an equivalent response. The Schild slope was determined to be 1, using statistical nonlinear modeling methods similar to those described by Waud (1976), Equation 27, p. 164 (Ref. 2). The Schild slope equal to 1 indicates the model is consistent with the assumptions of a competitive antagonist; therefore, the pA2 may be interpreted as the apparent $K_B$, the dissociation constant of the inhibitor.

To estimate the drug-induced suppression of the maximal responses, $sPLA_2$ responses (10 ug/ml) were determined in the absence and presence of drug, and percent suppression was calculated for each pair of tissues. Representative examples of inhibitory activities are presented in Table 2, below.

Ref. 1—van Rossum, J. M.: Cumulative dose-response curves. II. Technique for the making of dose-response curves in isolated organs and the evaluation of drug parameters. Arch. Int. Pharmacodyn. Ther. 143: 299–330, 1963.

Ref. 2—Waud, D.: Analysis of dose-response relationships. in *Advances in General and Cellular Pharmacology* eds Narahashi, Bianchi 1:145–178, 1976.

TABLE 2

| Compound of Example No. | Tissue Test ($sPLA_2$) | |
|---|---|---|
| | Apparent $K_B$ (uM) | % Supp(30 uM)[3] (10 uM^)[4] |
| 2 | 3.21 ± 0.44 | 60.5 ± 12.8 |
| 3 | 2.04 ± 0.25* | 77.9 ± 4.2 |
| 4 | 30.10 ± 4.71 | 11.0 ± 10.3 |

TABLE 2-continued

| Compound of Example No. | Tissue Test (sPLA$_2$) | |
|---|---|---|
| | Apparent K$_B$ (uM) | % Supp(30 uM)[3] (10 uM^)[4] |
| 5 | 27.13 ± 7.04 | 21.2 ± 12.5 |
| 16 | 1.57 ± 0.23 | 83.9 ± 3.2 |
| | | 55.2 ± 6.6^ |
| 18 | 1.13 ± 0.25* | 98.0 ± 1.5 |
| | | 70.7 ± 6.4^ |
| 24 | 130.85 ± 238 | −4.2 ± 6.2 |
| 25 | 22.62 ± 5.43 | 7.3 ± 9.9 |
| 30 | 3.86 ± 0.35 | 60.9 ± 9.7 |
| | | 21.4 17.5^ |
| 31 | 5.96 ± 0.91 | 47.5 ± 13.4 |
| 43 | 0.85 ± 0.26 | 91.3 ± 6.0^ |
| 44 | 0.76 ± 0.18 | 87.4 ± 9.3 |
| 52 | 2.81 ± 0.30 | 29.1 ± 7.0 |
| | | 37.8 ± 15.5^ |
| 57 | 2.54 ± 0.22 | 66.3 ± 5.9 |
| 61 | 2.39 ± 0.80 | 72.3 ± 4.5 |
| 68 | 1.39 ± 0.21 | 48.0 ± 7.0^ |
| | | 41.2 ± 3.8^ |
| 70 | 5.94 ± 0.83 | 45.1 ± 6.8 |

Notes:
[3] % supression of sPLA$_2$ contraction at compound concentration of 30 uM.
[4] % suppression of sPLA$_2$ contraction at compound concentration of 10 uM.
*indicates transient contraction of tissue during test.

While the present invention has been illustrated above by certain specific embodiments, it is not intended that these specific examples should limit the scope of the invention as described in the appended claims.

We claim:

1. A 1H-indole-3-acetic acid hydrazide represented by the formula (III), and pharmaceutically acceptable salts thereof;

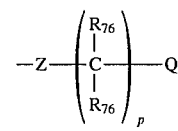

(III)

wherein;

X is oxygen or sulfur;

$R_{21}$ is selected from groups (i), (ii) and (iii) where;
(i) is $C_4$–$C_{20}$ alkyl, $C_4$–$C_{20}$ alkenyl, $C_4$–$C_{20}$ alkynyl, $C_4$–$C_{20}$ haloalkyl, $C_4$–$C_{12}$ cycloalkyl, or
(ii) is aryl or aryl substituted by halo, —CN, —CHO, —OH, —SH, $C_1$–$C_{10}$ alkylthio, $C_1$–$C_{10}$ alkoxy, $C_1$–$C_{10}$ alkyl, carboxyl, amino, or hydroxyamino;
(iii) is

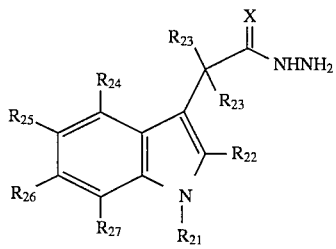

where y is from 1 to 8, $R_{74}$ is, independently, hydrogen or $C_1$–$C_{10}$ alkyl, and $R_{75}$ is aryl or aryl substituted by halo, —CN, —CHO, —OH, nitro, phenyl, —SH, $C_1$–$C_{10}$ alkylthio, $C_1$–$C_{10}$ alkoxy, $C_1$–$C_{10}$ alkyl, amino, hydroxyamino, benzyloxy, or pyridyl;

$R_{22}$ is halo, $C_1$–$C_3$ alkyl, ethenyl, $C_1$–$C_2$ alkylthio, $C_1$–$C_2$ alkoxy, —CHO, —CN;

each $R_{23}$ is independently hydrogen, $C_1$–$C_3$ alkyl, or halo;

$R_{24}$, $R_{25}$, $R_{26}$, and $R_{27}$ are each independently hydrogen, $C_1$–$C_{10}$ alkyl, $C_2$–$C_{10}$ alkenyl, $C_2$–$C_{10}$ alkynyl, $C_3$–$C_8$ cycloalkyl, aryl, aralkyl, $C_1$–$C_{10}$ haloalkyl, $C_2$–$C_{10}$ alkoxy, $C_1$–$C_{10}$ haloalkoxy, $C_4$–$C_8$ cycloalkoxy, phenoxy, halo, hydroxy, carboxyl, —SH, —CN, —S($C_1$–$C_{10}$ alkyl), arylthio, thioacetal, —C(O)O($C_1$–$C_{10}$ alkyl), hydrazino, hydrazido, —NH$_2$, —NO$_2$, —NR$_{82}$R$_{83}$, and —C(O)NR$_{82}$R$_{83}$, where, $R_{82}$ and $R_{83}$ are independently hydrogen, $C_1$–$C_{10}$ alkyl, or $C_1$–$C_{10}$ hydroxyalkyl; or a group having the formula;

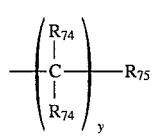

where, each $R_{76}$ is independently selected from hydrogen, $C_1$–$C_{10}$ alkyl, hydroxy, or both $R_{76}$ taken together are =O;

p is 1 to 8,

Z is a bond, —O—, —N($C_1$–$C_{10}$ alkyl)—, —NH, or —S—; and

Q is —CON(R$_{82}$R$_{83}$), -5-tetrazolyl, —SO$_3$H,

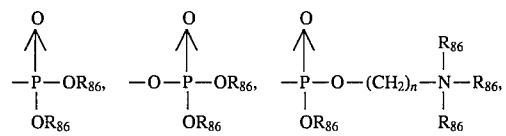

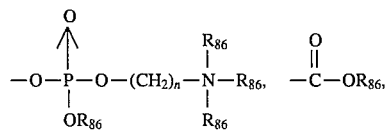

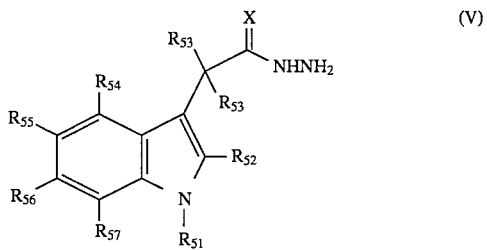

where $R_{86}$ is, independently, hydrogen, a metal, or $C_1$–$C_{10}$ alkyl, and n is a number from 1 to 8.

2. A 1H-indole-3-acetic acid hydrazide represented by the formula (V), and pharmaceutically acceptable salts thereof;

(V)

wherein;

X is oxygen;

$R_{51}$ is

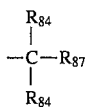

where, $R_{84}$ is hydrogen or $C_1$-$C_{10}$ alkyl, and $R_{87}$ is, aryl or aryl substituted by halo, —CN, —CHO, —OH, nitro, phenyl, —SH, $C_1$-$C_{10}$ alkylthio, $C_1$-$C_{10}$ alkyl, $C_1$-$C_{10}$ alkoxy, carboxyl, amino, hydroxyamino, benzyloxy or pyridyl;

$R_{52}$ is halo, methylthio, or $C_1$-$C_3$ alkyl;

each $R_{53}$ is hydrogen or halo;

$R_{54}$, $R_{55}$, $R_{56}$, and $R_{57}$ are each independently hydrogen, $C_1$-$C_{10}$ alkyl, $C_2$-$C_{10}$ alkenyl, $C_2$-$C_{10}$ alkynyl, $C_3$-$C_8$ cycloalkyl, aryl, aralkyl, or $C_1$-$C_{10}$ haloalkyl, $C_2$-$C_{10}$ alkoxy, $C_1$-$C_{10}$ haloalkoxy, $C_4$-$C_8$ cycloalkoxy, phenoxy, halo, hydroxy, carboxyl, —SH, —CN, —S($C_1$-$C_{10}$ alkyl), arylthio, thioacetal, —C(O)O($C_1$-$C_{10}$ alkyl), hydrazino, hydrazido, —NH$_2$, —NO$_2$, —NR$_{82}$R$_{83}$, and —C(O)NR$_{82}$R83, where, $R_{82}$ and $R_{83}$ are independently hydrogen, $C_1$-$C_{10}$ alkyl, $C_1$-$C_{10}$ hydroxyalkyl; or a group having the formula;

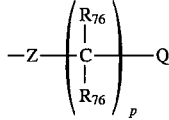

where, each $R_{76}$ is independently selected from hydrogen, $C_1$-$C_{10}$ alkyl, hydroxy, or both $R_{76}$ taken together are =O;

p is 1to 8,

Z is a bond, —O—, —N($C_1$-$C_{10}$ alkyl)—, —NH, or —S—; and

Q is —CON(R$_{82}$R$_{83}$), -5-tetrazolyl, —SO$_3$H,

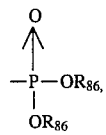

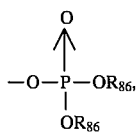

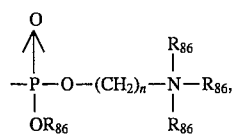

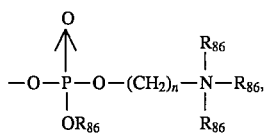

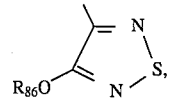

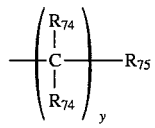

where $R_{86}$ is, independently, hydrogen, a metal, or $C_1$-$C_{10}$ alkyl, and n is a number from 1 to 8.

3. The compound of claim 1 wherein $R_{21}$ is selected from groups (i), (ii) and (iii) where;

(i) is $C_4$-$C_{20}$ alkyl, $C_4$-$C_{20}$ alkenyl, $C_4$-$C_{20}$ alkynyl, $C_4$-$C_{20}$ haloalkyl, $C_4$-$C_{12}$ cycloalkyl, or (ii) is aryl or aryl substituted by halo, —CN, —CHO, —OH, —SH, $C_1$-$C_{10}$ alkylthio, $C_1$-$C_{10}$ alkoxy, $C_1$-$C_{10}$ alkyl, carboxyl, amino, or hydroxyamino;

(iii) is $$-\left(\begin{array}{c}R_{74}\\|\\C\\|\\R_{74}\end{array}\right)_y - R_{75}$$

where y is from 1 to 8, $R_{74}$ is, independently, hydrogen or $C_1$-$C_{10}$ alkyl, and $R_{75}$ is naphthyl, or biphenyl.

4. A compound selected from the group consisting of:

5-cyclopentoxy-2-ethyl-1-(phenylmethyl)-1H-indole-3-acetic acid hydrazide, 2-ethyl-5-methoxy-1-(phenylmethyl)-1H-indole-3-acetic acid hydrazide, 2-ethyl-5-methyl-1-(phenylmethyl)-1H-indole-3-acetic acid hydrazide, 5-methoxy-2-methyl-1-(phenylmethyl)-1H-indole-3-acetic acid hydrazide, 1-[(3-chlorophenyl)methyl]-5-methoxy-2-methyl-1H-indole-3-acetic acid hydrazide, 2-chloro-5-methoxy-1-(phenylmethyl)-1H-indole-3-acetic acid hydrazide, 2-bromo-5-methoxy-1-(phenylmethyl)-1H-indole-3-acetic acid hydrazide, 5-methoxy-2-(methylthio)-1-(phenylmethyl)-1H-indole-3-acetic acid hydrazide, 5-chloro-2-methyl-1-(phenylmethyl)-1H-indole-3-acetic acid hydrazide, 5-carboxy-1-[(3-chlorophenyl)methyl]-2-methyl-1H-indole-3-acetic acid hydrazide, and mixtures thereof.

5. A pharmaceutical formulation comprising a compound as claimed in claim 1 together with a pharmaceutically acceptable carrier or diluent therefor.

6. A pharmaceutical formulation comprising a compound as claimed in claim 2 together with a pharmaceutically acceptable carrier or diluent therefor.

7. A pharmaceutical formulation comprising a compound as claimed in claim 4 together with a pharmaceutically acceptable carrier or diluent therefor.

8. A method of inhibiting sPLA$_2$ mediated release of fatty acids which comprises contacting sPLA$_2$ with an therapeutically effective amount of 1H-indole-3-acetic acid hydrazide and pharmaceutically acceptable salts thereof as claimed in claim 1.

9. A method of inhibiting sPLA$_2$ mediated release of fatty acids which comprises contacting sPLA$_2$ with an therapeutically effective amount of 1H-indole-3-acetic acid hydrazide and pharmaceutically acceptable salts thereof as claimed in claim 4.

10. A method of treating a human to alleviate the pathological effects of septic shock, adult respiratory distress syndrome, pancreatitis, trauma, bronchial asthma, allergic rhinitis, and rheumatoid arthritis; wherein the method comprises administration to said human of at least one 1H-indole-3-acetic acid hydrazide as claimed in claim 1 in an amount sufficient to inhibit $sPLA_2$ mediated release of fatty acid and to thereby inhibit or prevent the arachidonic acid cascade and its deleterious products.

* * * * *